US009608228B2

(12) United States Patent
Kuroki

(10) Patent No.: US 9,608,228 B2
(45) Date of Patent: Mar. 28, 2017

(54) ORGANIC LIGHT-EMITTING DEVICE WITH TRANSPARENT ELECTRODE HAVING BOTH CONDUCTIVITY AND OPTICAL TRANSPARENCY

(71) Applicant: Konica Minolta, Inc., Chiyoda-ku, Tokyo (JP)

(72) Inventor: Takaaki Kuroki, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 14/652,676

(22) PCT Filed: Dec. 6, 2013

(86) PCT No.: PCT/JP2013/082806
§ 371 (c)(1),
(2) Date: Jun. 16, 2015

(87) PCT Pub. No.: WO2014/097901
PCT Pub. Date: Jun. 26, 2014

(65) Prior Publication Data

US 2015/0340641 A1 Nov. 26, 2015

(30) Foreign Application Priority Data

Dec. 18, 2012 (JP) ................................ 2012-275296

(51) Int. Cl.
*H01L 51/52* (2006.01)
*H01L 51/00* (2006.01)
(Continued)

(52) U.S. Cl.
CPC ........ *H01L 51/5215* (2013.01); *C07D 405/14* (2013.01); *C07F 5/069* (2013.01);
(Continued)

(58) Field of Classification Search
CPC ............. H01L 51/5215; H01L 51/5268; H01L 51/0067; H01L 51/0073; H01L 51/0072;
(Continued)

(56) References Cited

U.S. PATENT DOCUMENTS

2013/0114269 A1* 5/2013 Domercq ............ H01L 51/5215
362/311.05

FOREIGN PATENT DOCUMENTS

JP 2002015623 A 1/2002
JP 2006164961 A 6/2006
(Continued)

OTHER PUBLICATIONS

International Search Report corresponding to International Application No. PCT/JP2013/082806; Date of Mailing: Mar. 11, 2014, with English translation.
(Continued)

*Primary Examiner* — Mamadou Diallo
(74) *Attorney, Agent, or Firm* — Cantor Colburn LLP

(57) ABSTRACT

An organic light-emitting device includes an internal light extraction layer including a scattering layer and a smooth layer; and a transparent electrode including an underlying layer and an electrode layer, wherein the transparent electrode is provided on the smooth layer side of the internal light extraction layer, the internal light extraction layer has a refractive index in the range of 1.7 to less than 2.5, and the electrode layer includes silver or an alloy including silver as a main component.

12 Claims, 9 Drawing Sheets

(51) Int. Cl.

| | |
|---|---|
| ***C07D 405/14*** | (2006.01) |
| ***C07F 9/50*** | (2006.01) |
| ***C07F 15/00*** | (2006.01) |
| ***C07F 5/06*** | (2006.01) |
| ***C07F 7/08*** | (2006.01) |

(52) U.S. Cl.
CPC .......... *C07F 7/0814* (2013.01); *C07F 9/5045* (2013.01); *C07F 15/0033* (2013.01); *H01L 51/0058* (2013.01); *H01L 51/0065* (2013.01); *H01L 51/0067* (2013.01); *H01L 51/0069* (2013.01); *H01L 51/0071* (2013.01); *H01L 51/0072* (2013.01); *H01L 51/0073* (2013.01); *H01L 51/0074* (2013.01); *H01L 51/0094* (2013.01); *H01L 51/5268* (2013.01)

(58) Field of Classification Search
CPC ............. H01L 51/0074; H01L 51/0094; H01L 51/0058
See application file for complete search history.

(56) References Cited

FOREIGN PATENT DOCUMENTS

| | | | |
|---|---|---|---|
| JP | 2008251217 | A | 10/2008 |
| JP | 2009151963 | A | 7/2009 |
| JP | 2010251675 | A | 11/2010 |
| JP | 2011077028 | A | 4/2011 |
| WO | 2012007575 | A1 | 1/2012 |

OTHER PUBLICATIONS

Written Opinion of the International Searching Authority corresponding to International Application No. PCT/JP2013/082806; Date of Mailing: Mar. 11, 2014, with English translation.

* cited by examiner

| | |
|---|---|
| AVERAGE SURFACE ROUGHNESS (Ra) | :1.398E+00 nm |
| MAXIMUM PEAK-TO-VALLEY HEIGHT (P-V) | :1.669E+01 nm |
| MAXIMUM PEAK (Rp) | :7.200E+00 nm |
| MAXIMUM VALLEY (Rv) | :−9.494E+00 nm |
| ROOT MEAN SQUARE SURFACE ROUGHNESS (RMS) | :1.788E+00 nm |
| n POINTS MEAN ROUGHNESS (Rz) | :1.023E+01 nm (10 Points) |
| SURFACE AREA (S) | :9.972E+07 $nm^2$ |
| SURFACE AREA RATIO (S ratio) | :1.001E+00 |

ORGANIC LIGHT-EMITTING DEVICE WITH TRANSPARENT ELECTRODE HAVING BOTH CONDUCTIVITY AND OPTICAL TRANSPARENCY

CROSS REFERENCE TO RELATED APPLICATIONS

This is the U.S. national stage of application No. PCT/JP2013/082806, filed on Dec. 6, 2013. Priority under 35 U.S.C. §119(a) and 35 U.S.C. §365(b) is claimed from Japanese Application No. 2012-275296, filed Dec. 18, 2012, the disclosure of which is also incorporated herein by reference.

TECHNICAL FIELD

The present invention relates to an organic light-emitting device and more specifically to an organic light-emitting device containing a transparent electrode having both conductivity and optical transparency.

BACKGROUND ART

Organic light-emitting devices that operate by electroluminescence (hereinafter abbreviated as EL) from organic materials, (what are called organic EL devices), are completely solid devices of a thin film type capable of emitting light at a low voltage ranging from several V to several 10 V and have many good characteristics such as high luminance, high luminous efficiency, small thickness, and lightweight. In recent years, therefore, they have attracted attention as backlights for a variety of displays, display boards for signboards, emergency lights, and the like, and surface emitting devices for illumination light sources and the like.

Such organic light-emitting devices have a structure including two electrodes and a light-emitting layer including an organic material disposed between the electrodes, in which light produced by the light-emitting layer is extracted outside through the electrode. Therefore, at least one of the two electrodes is formed as a transparent electrode.

Transparent electrodes generally used include oxide semiconductor materials such as indium tin oxide ($SnO_2$—$In_2O_3$, ITO). A stack of ITO and silver layers is also studied to provide lower resistance (e.g., refer to Patent Literatures 1 and 2). Unfortunately, ITO, which contains a rare metal, indium, is a high-cost material and needs to be annealed at about 300° C. for resistance reduction after it is deposited as a film. In addition, when ITO is deposited on a film substrate, a decrease in deposition temperature can occur to degrade the crystallinity, so that a problem can occur, such as failing to obtain an appropriate electrode resistance.

In contrast, a silver electrode film with very high conductivity can be formed even on a film substrate. Although has been previously studied widely, such a silver electrode trades off transparency for conductivity, and no transparent electrode has been practically achieved using a thin silver film.

To solve this problem, Patent Literature 3 shows the use of a silver-aluminum alloy. The alloy has improved transparency and conductivity as compared with a conventional one. Unfortunately, such improved transparency and conductivity are still at an unsatisfactory level.

On the other hand, Japanese Patent Application 2011-252003 by the present applicant discloses a thin silver transparent electrode that has significantly improved transparency and conductivity as compared with a conventional one. Such a thin silver transparent electrode is a very preferred mode.

However, a thin silver electrode has a problem with light distribution characteristics due to the effect of its unique optical properties. When a thin silver electrode is used, a method of simply providing a light extraction film or the like on the outside of the substrate (the interface between the substrate and the air) has limitations in improving luminous efficiency.

CITATION LIST

Patent Literatures

Patent Literature 1: JP 2002-15623 A
Patent Literature 2: JP 2006-164961 A
Patent Literature 3: JP 2009-151963 A

SUMMARY OF INVENTION

Technical Problem

It is therefore a principal object of the present invention to provide an organic light-emitting device possessing high luminous efficiency and containing a transparent electrode having both conductivity and optical transparency.

Solution to Problem

The object of the present invention is achieved using the following features.

1. An organic light-emitting device including: an internal light extraction layer including a scattering layer and a smooth layer; and a transparent electrode including an underlying layer and an electrode layer, wherein the transparent electrode is provided on a smooth layer side of the internal light extraction layer, the internal light extraction layer has a refractive index in the range of 1.7 to less than 2.5, and the electrode layer includes silver or an alloy including silver as a main component.

2. The organic light-emitting device according to the above 1, wherein the scattering layer contains particles with an average particle size of 0.2 μm to less than 1 μm and a refractive index of 1.7 to less than 3.0.

3. The organic light-emitting device according to the above 1, wherein the scattering layer has a smooth layer-side surface formed to have a dip-and-bump structure.

4. The organic light-emitting device according to any one of the above 1 to 3, wherein the underlying layer includes a nitrogen atom-containing compound.

5. The organic light-emitting device according to the above 4, wherein the nitrogen atom-containing compound has a heterocyclic ring containing a nitrogen atom as a heteroatom.

6. The organic light-emitting device according to the above 4 or 5, wherein the nitrogen atom-containing compound has a pyridine group.

7. The organic light-emitting device according to any one of the above 4 to 6, wherein the nitrogen atom-containing compound is a compound represented by formula (1):

[Chemical formula 1]

$(Ar1)_{n1}$-Y1 Formula (1)

wherein n1 represents an integer of 1 or more,

Y1 represents a substituent when n1 is 1 or Y1 represents a simple bond or a n1-valent linking group when n1 is 2 or more, Ar1 represents a group represented by formula (A):

[Chemical formula 2]

Formula (A)

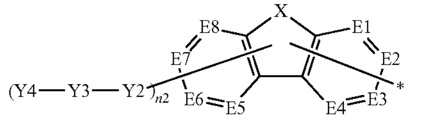

wherein X represents —N(R)—, —O—, —S—, or —Si(R)(R')—, E1 to E8 each independently represent —C(R1)= or N=, R, R', and R1 each independently represent a hydrogen atom, a substituent, or a linking site to Y1, * represents a linking site to Y1, Y2 represents a simple bond or a divalent linking group, Y3 and Y4 each represent a group derived from a five- or six-membered aromatic ring, at least one of Y3 and Y4 represents a group derived from an aromatic heterocyclic ring containing a nitrogen atom as a ring-constituting atom, and n2 represents an integer of 1 to 4, when n1 is 2 or more, a plurality of occurrences of Ar1 may be the same or different, and the compound represented by formula (1) has, in its molecule, at least two condensed aromatic heterocyclic rings each formed by condensation of three or more rings.

Advantageous Effects of Invention

The present invention makes it possible to provide an organic light-emitting device possessing high luminous efficiency and containing a transparent electrode having both conductivity and optical transparency.

Although the mechanism for developing and achieving the advantageous effects of the present invention is not clear, the following speculation is possible.

The present invention has been made in view of the unique optical properties of an organic light-emitting device containing a transparent electrode including silver with a relatively low refractive index. Specifically, it is intended that an electrode of silver, with a relatively low refractive index, having both conductivity and transparency should be formed as thin as possible so that light leakage (evanescent effect) can be produced to reduce the quantity of light confined in a light-emitting layer.

To achieve such performance of a thin silver electrode, a specific material is used to form an underlying layer for the electrode, and the underlying layer is formed so as to have a high refractive index similarly to the light-emitting layer, so that electrode characteristics and optical loss can be reduced.

In addition, an internal light extraction layer is also formed to have a high refractive index similarly to the light-emitting layer and the underlying layer, so that light can be smoothly introduced with reduced optical loss, and scattering particles forming a specific structure are used to produce a scattering effect, so that light distribution characteristics significantly disturbed by the thin silver electrode (a large quantity of light at a deep angle) can be made close to Lambert characteristics (the forward emission component can be increased), which makes it possible to reduce optical loss at the refractive index interface with the substrate and to increase primary light extraction.

It is also conceivable that the transparency of each layer can be made significantly higher than that in conventional techniques and the efficiency reduction during multiple scattering can be minimized, so that the extraction efficiency can be increased.

DESCRIPTION OF EMBODIMENTS

Hereinafter, the present invention, the elements of the present invention, and embodiments and modes for carrying out the present invention will be described in detail.

As used herein, the term "to" means to include the values before and after it as the lower and upper limits.

First Embodiment

<Structure of Organic Light-Emitting Device>

Figure 1:
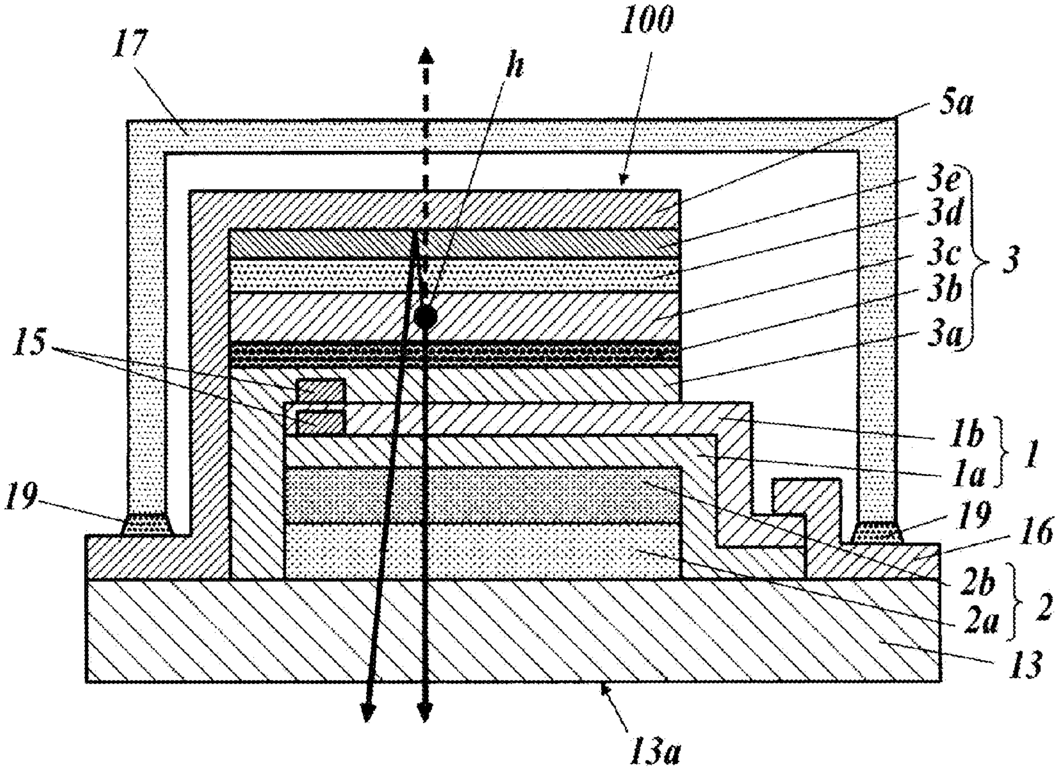
FIG. 1 is a schematic cross-sectional view showing the structure of an organic light-emitting device according to a first embodiment.

As shown in FIG. 1, an organic light-emitting device 100 according to the present invention is provided on a transparent substrate 13 and includes an internal light extraction layer 2, a transparent electrode 1, a light-emitting functional layer 3 including an organic material and other materials, and a counter electrode 5*a*, which are stacked in this order from the transparent substrate 13 side. An extraction electrode 16 is provided at the end of the transparent electrode 1 (electrode layer 1*b*). The transparent electrode 1 and an external power source (not shown) are electrically connected through the extraction electrode 16. The organic light-emitting device 100 is so configured that generated light (emitted light h) is extracted from at least the transparent substrate 13 side.

The layer structure of the organic light-emitting device 100 is not restricted and may be any common layer structure. In this embodiment, the transparent electrode 1 functions as an anode (or a positive pole), and the counter electrode 5*a* functions as a cathode (or a negative pole). In this case, for example, the light-emitting functional layer 3 has an illustrative layer structure including a hole injection layer 3*a*, a hole transport layer 3*b*, a light-emitting layer 3*c*, an electron transport layer 3*d*, and an electron injection layer 3*e*, stacked in this order from the transparent electrode 1 (anode) side, in which the light-emitting layer 3*c* including at least an organic material is an essential component. The hole injection layer 3*a* and the hole transport layer 3*b* may be provided as a hole transport/injection layer. The electron transport layer 3*d* and the electron injection layer 3*e* may be provided as an electron transport/injection layer. Among these components of the light-emitting functional layer 3, for example, the electron injection layer 3*e* may be made of an inorganic material.

Besides these layers, the light-emitting functional layer 3 may have an optional layer, such as a hole-blocking layer or an electron-blocking layer, disposed at a necessary position. The light-emitting layer 3*c* may have different luminescent layers capable of emitting light indifferent wavelength regions, in which the different luminescent layers may be stacked with a non-light-emitting intermediate layer interposed therebetween. The intermediate layer may function as a hole-blocking layer or an electron-blocking layer. The counter electrode 5*a* as a cathode may also have a multilayer structure as needed. In such a structure, only the part where the light-emitting functional layer 3 is sandwiched between the transparent electrode 1 and the counter electrode 5*a* serves as a light-emitting region in the organic light-emitting device 100.

In order to reduce the resistance of the transparent electrode 1, the layer structure shown above may also include an auxiliary electrode 15 in contact with the electrode layer 1*b* of the transparent electrode 1.

The organic light-emitting device 100 configured as describe above on the transparent substrate 13 is sealed with a sealant 17 for preventing the degradation of the light-emitting functional layer 3 including an organic material and other materials. The sealant 17 is fixed with an adhesive 19 on the transparent substrate 13 side. It should be noted that the terminal part of the transparent electrode 1 (extraction electrode 16) and the terminal part of the counter electrode 5*a* are exposed from the sealant 17, being insulated from each other by the light-emitting functional layer 3 on the transparent substrate 13.

Hereinafter, the details of each principal layer used to form the organic light-emitting device 100 and methods for the production thereof will be described.

<Transparent Electrode>

As shown in FIG. 1, the transparent electrode 1 has a two-layer structure including an underlying layer 1*a* and an electrode layer 1*b* deposited thereon, which are stacked in order from the transparent substrate 13 side. In this structure, the electrode layer 1*b* includes silver or an alloy including silver as a main component, and the underlying layer 1*a* includes, for example, a nitrogen atom-containing compound.

Regarding the transparent electrode 1, the term "transparent" means that it has a light transmittance of 50% or more at a wavelength of 550 nm. In the present invention, the main component of the electrode layer 1*b* refers to a component of which the content in the electrode layer 1*b* is the highest.

(1) Underlying Layer

The underlying layer 1*a* is provided on the transparent substrate 13 side of the electrode layer 1*b*. The material used to form the underlying layer 1*a* is not restricted. The underlying layer 1*a* may include any material capable of suppressing the aggregation of silver in the process of forming the electrode layer 1*b* including silver or an alloy including silver as a main component. Such a material may be, for example, a nitrogen atom-containing compound or the like.

When the underlying layer 1*a* includes a low-refractive-index material (less than 1.7 in refractive index), the upper limit of its thickness should be less than 50 nm, preferably less than 30 nm, more preferably less than 10 nm, even more preferably less than 5 nm. When its thickness is less than 50 nm, optical loss can be kept to a minimum. On the other hand, the lower limit of its thickness should be 0.05 nm or more, preferably 0.1 nm or more, more preferably 0.3 nm or more. The underlying layer 1*a* with a thickness of 0.05 nm or more can be uniformly formed and uniformly effective (in suppressing the aggregation of silver).

When the underlying layer 1*a* includes a high-refractive-index material (1.7 or more in refractive index), the upper limit of its thickness is not restricted, and its thickness may have the same lower limit as in the case where the layer includes a low-refractive-index material.

It should be noted that in order for the underlying layer 1*a* to simply work, it is enough to form the layer 1*a* with a thickness required for uniform deposition.

In a preferred mode, the underlying layer 1*a* may also serve as the smooth layer 2*b* described below. In this case, the underlying layer 1*a* is required both to be designed to have a reliable surface smoothness necessary as the smooth layer 2*b* and to function as part of the electrode member.

In this case, the internal light extraction layer 2 and the transparent electrode 1 may be composed of a scattering layer 2*a* (with no smooth layer 2*b*), the underlying layer 1*a*, and the electrode layer 1*b*, arranged in order from the transparent substrate 13 side, or composed of a scattering layer 2*a*, a smooth layer 2*b*, the underlying layer 1*a*, and the electrode layer 1*b*, arranged in order from the transparent substrate 13 side (not shown).

When the underlying layer 1*a* is a single layer capable of functioning as a smooth layer 2*b*, its thickness should preferably be set as if it was the smooth layer 2*b*.

The underlying layer 1*a* can be deposited by a method using a wet process such as application, ink-jetting, coating, or dipping or by a method using a dry process such as vapor deposition (such as resistive heating or electron beam deposition), sputtering, or CVD. In particular, vapor deposition is preferably used.

Any compound containing a nitrogen atom or atoms in the molecule may be used to form the underlying layer 1*a*. Preferably, a compound having a heterocyclic ring containing a nitrogen atom as a heteroatom is used to form the underlying layer 1*a*. The heterocyclic ring containing a nitrogen atom as a heteroatom may be aziridine, azirine, azetidine, azete, azolidine, azole, azinane, pyridine, azepane, azepine, imidazole, pyrazole, oxazole, thiazole, imidazoline, pyrazine, morpholine, thiazine, indole, isoindole, benzimidazole, purine, quinoline, isoquinoline, quinoxaline, cinnoline, pteridine, acridine, carbazole, benzo-C-cinnoline, porphyrin, chlorin, choline, or the like.

In particular, the compound having a heterocyclic ring containing a nitrogen atom as a heteroatom is preferably a compound represented by formula (1) below.

(1.1) Compound Represented by Formula (1)

The underlying layer 1*a* preferably includes a compound represented by formula (1) below.

[Chemical formula 3]

(Ar1)*n*1-Y1 Formula (1)

In formula (1), n1 represents an integer of 1 or more. When n1 is 1, Y1 represents a substituent, and when n1 is 2 or more, Y1 represents a simple bond or an n1-valent linking group. Ar1 represents a group represented by formula (A) shown below, and when n1 is 2 or more, two or more occurrences of Ar1 may be the same or different. The compound represented by formula (1) has, in its molecule, at least two condensed aromatic heterocyclic rings each formed by condensation of three or more rings.

In formula (1), the substituent represented by Y1 may be alkyl (e.g., methyl, ethyl, propyl, isopropyl, tert-butyl, pentyl, hexyl, octyl, dodecyl, tridecyl, tetradecyl, or pentadecyl), cycloalkyl (e.g., cyclopentyl or cyclohexyl), alkenyl (e.g., vinyl or allyl), alkynyl (e.g., ethynyl or propargyl), an aromatic hydrocarbon group (also referred to as an aromatic carbon ring group, aryl group, or the like, e.g., phenyl, p-chlorophenyl, mesityl, tolyl, xylyl, naphthyl, anthryl, azulenyl, acenaphthenyl, fluorenyl, phenanthryl, indenyl, pyrenyl, or biphenylyl), an aromatic heterocyclic group (e.g., furyl, thienyl, pyridyl, pyridazinyl, pyrimidinyl, pyrazinyl, triazinyl, imidazolyl, pyrazolyl, thiazolyl, quinazolinyl, carbazolyl, carbolinyl, diazacarbazolyl (referring to a moiety derived from a carbolinyl group by replacing any one of carbon atoms in the carboline ring with a nitrogen atom), or phthalazinyl), a heterocyclic group (e.g., pyrrolidyl, imidazolidyl, morpholyl, or oxazolidyl), alkoxy (e.g., methoxy, ethoxy, propyloxy, pentyloxy, hexyloxy, octyloxy, or dodecyloxy), cycloalkoxy (e.g., cyclopentyloxy or cyclohexyloxy), aryloxy (e.g., phenoxy or naphthyloxy), alkylthio (e.g., methylthio, ethylthio, propylthio, pentylthio, hexylthio, octylthio, or dodecylthio), cycloalkylthio (e.g., cyclopentylthio or cyclohexylthio), arylthio (e.g., phenylthio or naphthylthio), alkoxycarbonyl (e.g., methyloxycarbonyl, ethyloxycarbonyl, butyloxycarbonyl, octyloxycarbonyl, or dodecyloxycarbonyl), aryloxycarbonyl (e.g., phenyloxycarbonyl or naphthyloxycarbonyl), sulfamoyl (e.g., aminosulfonyl, methylaminosulfonyl, dimethylaminosulfonyl, butylaminosulfonyl, hexylaminosulfonyl, cyclohexylaminosulfonyl, octylaminosulfonyl, dodecylaminosulfonyl, phenylaminosulfonyl, naphthylaminosulfonyl, or 2-pyridylaminosulfonyl), acyl (e.g., acetyl, ethylcarbonyl, propylcarbonyl, pentylcarbonyl, cyclohexylcarbonyl, octylcarbonyl, 2-ethylhexylcarbonyl, dodecylcarbonyl, phenylcarbonyl, naphthylcarbonyl, or pyridylcarbonyl), acyloxy (e.g., acetyloxy, ethylcarbonyloxy, butylcarbonyloxy, octylcarbonyloxy, dodecylcarbonyloxy, or phenylcarbonyloxy), amido (e.g., methylcarbonylamino, ethylcarbonylamino, dimethylcarbonylamino, propylcarbonylamino, pentylcarbonylamino, cyclohexylcarbonylamino, 2-ethylhexylcarbonylamino, octylcarbonylamino, dodecylcarbonylamino, phenylcarbonylamino, or naphthylcarbonylamino), carbamoyl (e.g., aminocarbonyl, methylaminocarbonyl, dimethylaminocarbonyl, propylaminocarbonyl, pentylaminocarbonyl, cyclohexylaminocarbonyl, octylaminocarbonyl, 2-ethylhexylaminocarbonyl, dodecylaminocarbonyl, phenylaminocarbonyl, naphthylaminocarbonyl, or 2-pyridylaminocarbonyl), ureido (e.g., methylureido, ethylureido, pentylureido, cyclohexylureido, octylureido, dodecylureido, phenylureido, naphthylureido, or 2-pyridylaminoureido), sulfinyl (e.g., methylsulfinyl, ethylsulfinyl, butylsulfinyl, cyclohexylsulfinyl, 2-ethylhexylsulfinyl, dodecylsulfinyl, phenylsulfinyl, naphthylsulfinyl, or 2-pyridylsulfinyl), alkylsulfonyl (e.g., methylsulfonyl, ethylsulfonyl, butylsulfonyl, cyclohexylsulfonyl, 2-ethylhexylsulfonyl, or dodecylsulfonyl), arylsulfonyl or heteroarylsulfonyl (e.g., phenylsulfonyl, naphthylsulfonyl, or 2-pyridylsulfonyl), amino (e.g., amino, ethylamino, dimethylamino, butylamino, cyclopentylamino, 2-ethylhexylamino, dodecylamino, anilino, naphthylamino, 2-pyridylamino, piperidyl (also referred to as piperidinyl), or 2,2,6,6-tetramethylpiperidinyl), a halogen atom (e.g., fluorine atom, chlorine atom, or bromine atom), a fluorinated hydrocarbon group (e.g., fluoromethyl, trifluoromethyl, pentafluoroethyl, or pentafluorophenyl), cyano, nitro, hydroxy, mercapto, silyl (e.g., trimethylsilyl, triisopropylsilyl, triphenylsilyl, or phenyldiethylsilyl), a phosphate group (e.g., dihexylphosphoryl), a phosphite group (e.g., diphenylphosphinyl), phosphono, or the like.

These substituents may be further substituted with any of these substituents. Two or more occurrences of any of these substituents may also be linked together to form a ring.

In formula (1), the n1-valent linking group represented by Y1 may be specifically a divalent linking group, a trivalent linking group, a tetravalent linking group, or the like.

In formula (1), the divalent linking group represented by Y1 may be alkylene (e.g., ethylene, trimethylene, tetramethylene, propylene, ethylethylene, pentamethylene, hexamethylene, 2,2,4-trimethylhexamethylene, heptamethylene, octamethylene, nonamethylene, decamethylene, undecamethylene, dodecamethylene, cyclohexylene (e.g., 1,6-cyclohexanediyl), or cyclopentylene (e.g., 1,5-cyclopentanediyl)), alkenylene (e.g., vinylene, propenylene, butenylene, pentenylene, 1-methylvinylene, 1-methylpropenylene, 2-methylpropenylene, 1-methylpentenylene, 3-methylpentenylene, 1-ethylvinylene, 1-ethylpropenylene, 1-ethylbutenylene, or 3-ethylbutenylene), alkynylene (e.g., ethynylene, 1-propynylene, 1-butynylene, 1-pentynylene, 1-hexynylene, 2-butynylene, 2-pentynylene, 1-methylethynylene, 3-methyl-1-propynylene, or 3-methyl-1-butynylene), arylene (e.g., o-phenylene, p-phenylene, naphthalenediyl, anthracenediyl, naphthacenediyl, pyrenediyl, naphthylnaphthalenediyl, biphenyldiyl (e.g., [1,1'-biphenyl]-4,4'-diyl, 3,3'-biphenyldiyl, or 3,6-biphenyldiyl), terphenyldiyl, quaterphenyldiyl, quinquephenyldiyl, sexiphenyldiyl, septiphenyldiyl, octiphenyldiyl, noviphenyldiyl, or deciphenyldiyl), heteroarylene (e.g., a divalent group derived from at least one selected from the group consisting of a carbazole ring, a carboline ring, a diazacarbazole ring (also referred to as a monoazacarboline ring, which is a ring structure derived from a carboline ring by replacing a carbon atom in the carboline ring with a nitrogen atom), a triazole ring, a pyrrole ring, a pyridine ring, a pyrazine ring, a quinoxaline ring, a thiophene ring, an oxadiazole ring, a dibenzofuran ring, a dibenzothiophene ring, and an indole ring), a chalcogen atom such as oxygen or sulfur, or a group derived from a condensed aromatic heterocyclic ring formed by condensation of three or more rings, wherein the condensed aromatic heterocyclic ring formed by condensation of three or more rings preferably has a heteroatom selected from N, O, and S as an element in the condensed ring and may be specifically an acridine ring, a benzoquinoline ring, a carbazole ring, a phenazine ring, a phenanthridine ring, a phenanthroline ring, a carboline ring, a cyclazine ring, a quindoline ring, a terpenidine ring, a quinindoline ring, a triphenodithiazine ring, a triphenodioxazine ring, a phenantrazine ring, an anthrazine ring, a perimidine ring, a diazacarbazole ring (referring to a ring derived from a carboline ring by replacing any one carbon atom in the carboline ring with a nitrogen atom), a phenanthroline ring, a dibenzofuran ring, a dibenzothiophene ring, a naphthofuran ring, a naphthothiophene ring, a benzodifuran ring, a benzodithiophene ring, a naphthodifuran ring, a naphthodithiophene ring, an anthrafuran ring, an anthradifuran ring, an anthrathiophene ring, an anthradithiophene ring, a thianthrene ring, a phenoxathiin ring, or a thiophanthrene ring (naphthothiophene ring).

In formula (1), the trivalent linking group represented by Y1 may be, for example, ethanetriyl, propanetriyl, butanetriyl, pentanetriyl, hexanetriyl, heptanetriyl, octanetriyl, nonanetriyl, decanetriyl, undecanetriyl, dodecanetriyl, cyclohexanetriyl, cyclopentanetriyl, benzenetriyl, naphthalenetriyl, pyridinetriyl, carbazoletriyl, or the like.

In formula (1), the tetravalent linking group represented by Y1 may be a group derived from the trivalent group by adding one linking group, which may be, for example, propanediylidene, 1,3-propanediyl-2-ylidene, butanediylidene, pentanediylidene, hexanediylidene, heptanediylidene, octanediylidene, nonanediylidene, decanediylidene, undecanediylidene, dodecanediylidene, cyclohexanediylidene, cyclopentanediylidene, benzenetetrayl, naphthalenetetrayl, pyridinetetrayl, or carbazoletetrayl.

In formula (1), the divalent, trivalent, and tetravalent linking groups may each further have a substituent represented by Y1.

In the compound represented by formula (1), Y1 preferably represents a group derived from a condensed aromatic heterocyclic ring formed by condensation of three or more rings. The condensed aromatic heterocyclic ring formed by condensation of three or more rings is preferably a dibenzofuran ring or a dibenzothiophene ring.

In formula (1), n1 is preferably 2 or more.

In addition, the compound represented by formula (1) has, in its molecule, at least two condensed aromatic heterocyclic rings each formed by condensation of three or more rings.

When Y1 represents the n1-valent linking group, Y1 is preferably non-conjugated so that the compound represented by formula (1) can have high triplet excitation energy. In addition, the Y1 group preferably includes an aromatic ring (an aromatic hydrocarbon ring+an aromatic heterocyclic ring) so that the Tg (also referred to as the glass transition point or temperature) of the compound can be increased.

As used herein, the term "non-conjugated" means a case where the linking group does not have alternate single and double bonds or a case where the conjugation is three-dimensionally interrupted between aromatic rings in the linking group.

(Group Represented by Formula (A))

In formula (1), Ar1 represents a group represented by formula (A) below.

[Chemical formula 4]

Formula (A)

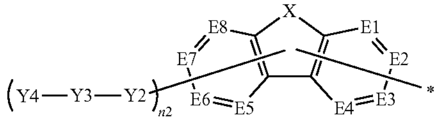

In formula (A), X represents —N(R)—, —O—, —S—, or —Si(R)(R')—. E1 to E8 each independently represent —C(R1)= or —N=. R, R', and R1 each independently represent a hydrogen atom, a substituent, or a linking site to Y1. The symbol * represents a linking site to Y1. Y2 represents a simple bond or a divalent linking group. Y3 and Y4 each represent a group derived from a five- or six-membered aromatic ring, and at least one of Y3 and Y4 represents a group derived from an aromatic heterocyclic ring containing a nitrogen atom as a ring-constituting atom, and n2 represents an integer of 1 to 4.

In formula (A), the substituent represented by each of R, R', and R1 has the same meaning as the substituent represented by Y1 in formula (1).

In formula (A), the divalent linking group represented by Y2 has the same meaning as the divalent linking group represented by Y1 in formula (1).

The five- or six-membered aromatic ring, from which the group represented by each of Y3 and Y4 is derived, may be a benzene ring, an oxazole ring, a thiophene ring, a furan ring, a pyrrole ring, a pyridine ring, a pyridazine ring, a pyrimidine ring, a pyrazine ring, a diazine ring, a triazine ring, an imidazole ring, an isoxazole ring, a pyrazole ring, a triazole ring, or the like.

While Y3 and Y4 each represent a group derived from a five- or six-membered aromatic ring, at least one of Y3 and Y4 represents a group derived from an aromatic heterocyclic ring containing a nitrogen atom as a ring-constituting atom. The aromatic heterocyclic ring containing a nitrogen atom as a ring-constituting atom may be an oxazole ring, a pyrrole ring, a pyridine ring, a pyridazine ring, a pyrimidine ring, a pyrazine ring, a diazine ring, a triazine ring, an imidazole ring, an isoxazole ring, a pyrazole ring, a triazole ring, or the like.

In formula (A), Y3 preferably represents a group derived from the six-membered aromatic ring, more preferably a group derived from a benzene ring.

In formula (A), Y4 preferably represents a group derived from the six-membered aromatic ring, more preferably a group derived from an aromatic heterocyclic ring containing a nitrogen atom as a ring-constituting atom. Even more preferably, Y4 represents a group derived from a pyridine ring.

(Groups Represented by Formulae (A-1) to (A-4))

The group represented by formula (A) is preferably a group represented by any one of formulae (A-1), (A-2), (A-3), or (A-4) below.

[Chemical formula 5]

Formula (A-1)

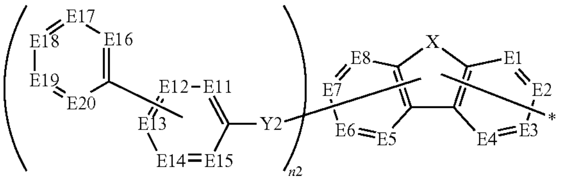

In formula (A-1), X represents —N(R)—, —O—, —S—, or —Si(R)(R')—. E1 to E8 each independently represent —C(R1)= or —N=. R, R', and R1 each independently represent a hydrogen atom, a substituent, or a linking site to Y1. Y2 represents a simple bond or a divalent linking group. E11 to E20 each independently represent —C(R2)= or —N═, and at least one of E11 to E20 represents —N═. R2 represents a hydrogen atom, a substituent, or a linking site, provided that at least one of E11 and E12 represents —C(R2)=, wherein R2 represents a linking site, and n2 represents an integer of 1 to 4. The symbol * represents a linking site to Y1 in formula (1).

[Chemical formula 6]

Formula (A-2)

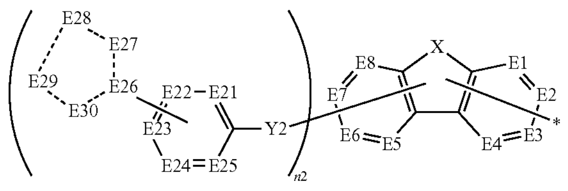

In formula (A-2), X represents —N(R)—, —O—, —S—, or —Si(R)(R')—. E1 to E8 each independently represent —C(R1)= or —N═. R, R', and R1 each independently represent a hydrogen atom, a substituent, or a linking site to Y1. Y2 represents a simple bond or a divalent linking group. E21 to E25 each independently represent —C(R2)= or —N═, E26 to E30 each independently represent —C(R2)=, —N═, —O—, —S—, or —Si(R3) (R4)-, and at least one of E21 to E30 represent —N═. R2 represents a hydrogen atom, a substituent, or a linking site, R3 and R4 each independently represent a hydrogen atom or a substituent, provided that at least one of E21 and E22 represents —C(R2)=, wherein R2 represents a linking site, and n2 represents an integer of 1 to 4. The symbol * represents a linking site to Y1 in formula (1).

[Chemical formula 7]

Formula (A-3)

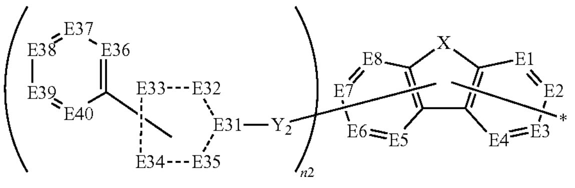

In formula (A-3), X represents —N(R)—, —O—, —S—, or —Si(R)(R')—. E1 to E8 each independently represent —C(R1)= or —N═. R, R', and R1 each independently represent a hydrogen atom, a substituent, or a linking site to Y1. Y2 represents a simple bond or a divalent linking group. E31 to E35 each independently represent —C(R2)=, —N═, —O—, —S—, or —Si(R3) (R4)-, E36 to E40 each independently represent —C(R2)= or —N═, and at least one of E31 to E40 represent —N═. R2 represents a hydrogen atom, a substituent, or a linking site, R3 and R4 each independently represent a hydrogen atom or a substituent, provided that at least one of E32 and E33 represents —C(R2)=, wherein R2 represents a linking site, and n2 represents an integer of 1 to 4. The symbol * represents a linking site to Y1 in formula (1).

[Chemical formula 8]

Formula (A-4)

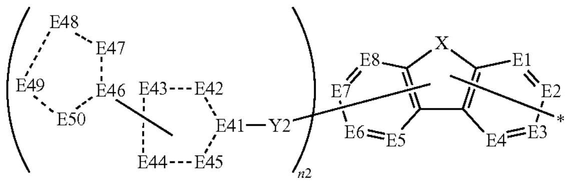

In formula (A-4), X represents —N(R)—, —O—, —S—, or —Si(R)(R')—. E1 to E8 each independently represent —C(R1)= or —N═. R, R', and R1 each independently represent a hydrogen atom, a substituent, or a linking site to Y1. Y2 represents a simple bond or a divalent linking group. E41 to E50 each independently represent —C(R2)=, —N═, —O—, —S—, or —Si(R3) (R4)-, and at least one of E41 to E50 represent —N═. R2 represents a hydrogen atom, a substituent, or a linking site, R3 and R4 each independently represent a hydrogen atom or a substituent, provided that at least one of E42 and E43 represents —C(R2)=, wherein R2 represents a linking site, and n2 represents an integer of 1 to 4. The symbol * represents a linking site to Y1 in formula (1).

In the groups represented by formulae (A-1) to (A-4), the substituent represented by each of R, R', and R1 has the same meaning as the substituent represented by Y1 in formula (1).

In the groups represented by formulae (A-1) to (A-4), the divalent linking group represented by Y2 has the same meaning as the divalent linking group represented by Y1 in formula (1).

In the groups represented by formulae (A-1) to (A-4), the substituent represented by R2 has the same meaning as the substituent represented by Y1 in formula (1).

In the groups represented by formulae (A-2) to (A-4), the substituent represented by each of R3 and R4 has the same meaning as the substituent represented by Y1 in formula (1).

(1.2) Compound Represented by Formula (2)

The compound represented by formula (1) is preferably a compound represented by formula (2) below.

[Chemical formula 9]

Formula (2)

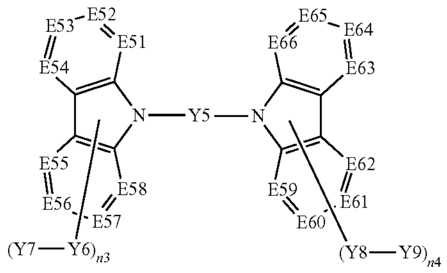

In formula (2), Y5 represents an arylene group, a heteroarylene group, or a divalent linking group including a combination thereof. E51 to E66 each represent —C(R3)= or —N═, wherein R3 represents a hydrogen atom or a substituent. Y6 to Y9 each represent a group derived from an aromatic hydrocarbon ring or a group derived from an aromatic heterocyclic ring, at least one of Y6 or Y7 and at least one of Y8 or Y9 each represent a group derived from an aromatic heterocyclic ring containing a N atom, and n3 and n4 each represent an integer of 0 to 4, provided that n3+n4 is an integer of 2 or more.

In formula (2), the arylene or heteroarylene group represented by Y5 has the same meaning as the arylene or heteroarylene group listed as an example of the divalent linking group represented by Y1 in formula (1).

Y5 represents an arylene group, a heteroarylene group, or a divalent linking group including a combination thereof. The heteroarylene group preferably includes a group derived from a condensed aromatic heterocyclic ring formed by condensation of three or more rings. The group derived from a condensed aromatic heterocyclic ring formed by condensation of three or more rings is preferably a group derived from a dibenzofuran ring or a group derived from a dibenzothiophene ring.

In formula (2), the substituent represented by R3 has the same meaning as the substituent represented by Y1 in formula (1).

Regarding the group represented by each of E51 to E66 in formula (2), six or more of E51 to E58 and six or more of E59 to E66 each preferably represent —C(R3)=.

In formula (2), E53 preferably represents —C(R3)=, wherein R3 preferably represents a linking site, and at the same time, E61 preferably represents —C(R3)=, wherein R3 preferably represents a linking site.

In formula (2), Y6 to Y9 may each represent a group derived from an aromatic hydrocarbon ring. In this case, the aromatic hydrocarbon ring may be, for example, a benzene ring, a biphenyl ring, a naphthalene ring, an azulene ring, an anthracene ring, a phenanthrene ring, a pyrene ring, a chrysene ring, a naphthacene ring, a triphenylene ring, an o-terphenyl ring, a m-terphenyl ring, a p-terphenyl ring, an acenaphthene ring, a coronene ring, a fluorene ring, a fluoranthrene ring, a naphthacene ring, a pentacene ring, a perylene ring, a pentaphene ring, a picene ring, a pyrene ring, a pyranthrene ring, an anthanthrene ring, or the like.

The aromatic hydrocarbon ring may further have a substituent such as that represented by Y1 in formula (1).

In formula (2), Y6 to Y9 may each represent a group derived from an aromatic heterocyclic ring. In this case, the aromatic heterocyclic ring may be, for example, a furan ring, a thiophene ring, an oxazole ring, a pyrrole ring, a pyridine ring, a pyridazine ring, a pyrimidine ring, a pyrazine ring, a triazine ring, a benzimidazole ring, an oxadiazole ring, a triazole ring, an imidazole ring, a pyrazole ring, a thiazole ring, an indole ring, an indazole ring, a benzimidazole ring, a benzothiazole ring, a benzoxazole ring, a quinoxaline ring, a quinazoline ring, a cinnoline ring, a quinoline ring, an isoquinoline ring, a phthalazine ring, a naphthyridine ring, a carbazole ring, a carboline ring, a diazacarbazole ring (referring to a ring derived from a carboline ring by replacing a carbon atom in the carboline ring with a nitrogen atom), or the like.

The aromatic heterocyclic ring may further have a substituent such as that represented by Y1 in formula (1).

In formula (2), at least one of Y6 or Y7 and at least one of Y8 or Y9 may each represent a group derived from an aromatic heterocyclic ring containing a N atom. In this case, the aromatic heterocyclic ring containing a N atom may be, for example, an oxazole ring, a pyrrole ring, a pyridine ring, a pyridazine ring, a pyrimidine ring, a pyrazine ring, a triazine ring, a benzimidazole ring, an oxadiazole ring, a triazole ring, an imidazole ring, a pyrazole ring, a thiazole ring, an indole ring, an indazole ring, a benzimidazole ring, a benzothiazole ring, a benzoxazole ring, a quinoxaline ring, a quinazoline ring, a cinnoline ring, a quinoline ring, an isoquinoline ring, a phthalazine ring, a naphthyridine ring, a carbazole ring, a carboline ring, a diazacarbazole ring (referring to a ring derived from a carboline ring by replacing a carbon atom in the carboline ring with a nitrogen atom), or the like.

In formula (2), Y7 and Y9 each preferably represent a group derived from a pyridine ring.

In formula (2), Y6 and Y8 each preferably represent a group derived from a benzene ring.

(1.3) Compound Represented by Formula (3)

The compound represented by formula (2) is preferably a compound represented by formula (3) below.

[Chemical formula 10]

Formula (3)

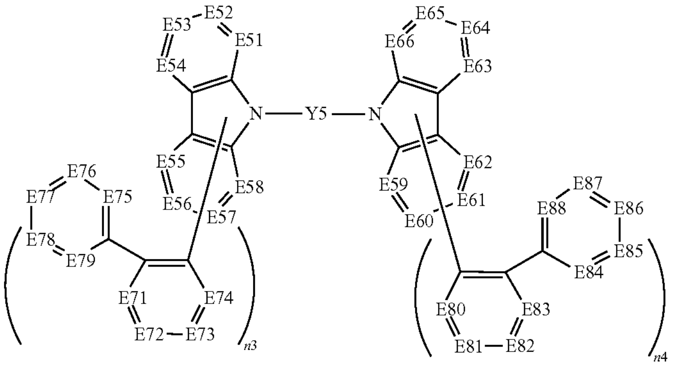

In formula (3), Y5 represents an arylene group, a heteroarylene group, or a divalent linking group including a combination thereof. E51 to E66 and E71 to E88 each represent —C(R3)= or —N=, wherein R3 represents a hydrogen atom or a substituent, provided that at least one of E71 to E79 and at least one of E80 to E88 each represent —N=, and n3 and n4 each represent an integer of 0 to 4, provided that n3+n4 is an integer of 2 or more.

In formula (3), the arylene or heteroarylene group represented by Y5 has the same meaning as the arylene or heteroarylene group listed as an example of the divalent linking group represented by Y1 in formula (1).

Y5 represents an arylene group, a heteroarylene group, or a divalent linking group including a combination thereof.

The heteroarylene group preferably includes a group derived from a condensed aromatic heterocyclic ring formed by condensation of three or more rings. The group derived from a condensed aromatic heterocyclic ring formed by condensation of three or more rings is preferably a group derived from a dibenzofuran ring or a group derived from a dibenzothiophene ring.

In formula (3), the substituent represented by R3 has the same meaning as the substituent represented by Y1 in formula (1).

In formula (3), six or more of E51 to E58 and six or more of E59 to E66 each preferably represent —C(R3)=.

In formula (3), at least one of E75 to E79 and at least one of E84 to E88 each preferably represent —N=.

In formula (3), E71 to E74 and E80 to E83 each preferably represent —C(R3)=.

In formula (3), E53 preferably represents —C(R3), wherein R3 preferably represents a linking site, and at the same time, E61 preferably represents —C(R3)=, wherein R3 preferably represents a linking site.

E75 and E84 each preferably represent —N=, and E71 to E74 and E80 to E83 each preferably represent —C(R3)=.

(1.4) Specific Examples of Compound

Hereinafter, non-limiting specific examples of the compound represented by formula (1), (2), or (3) (illustrative compounds 1 to 112) for use in the present invention will be shown.

[Chemical formula 11]

1

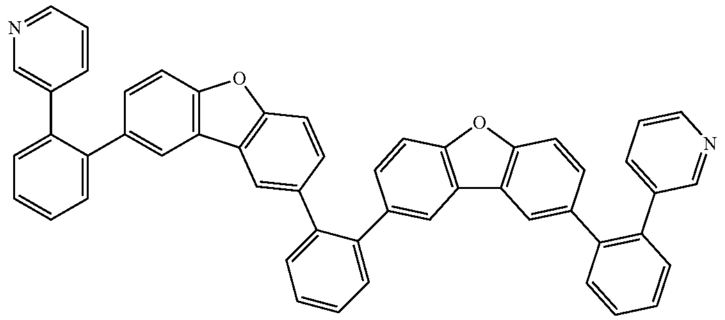

2

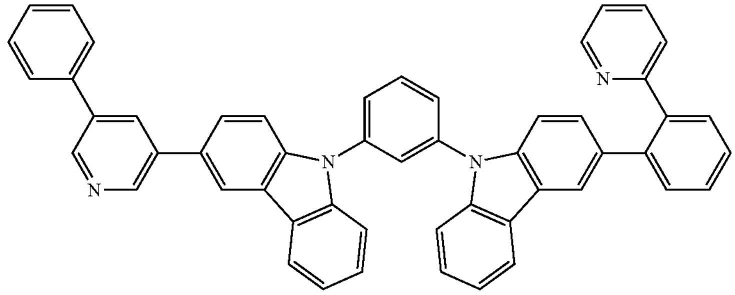

3

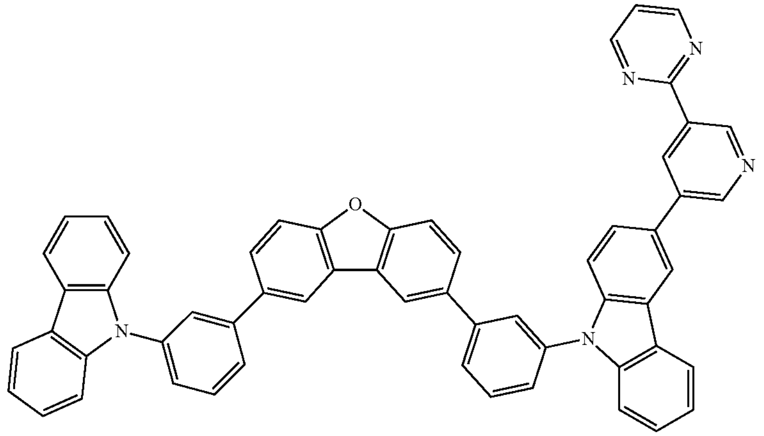

-continued
4
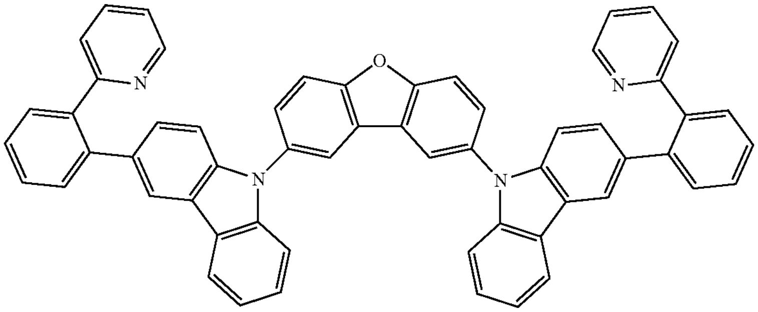
5
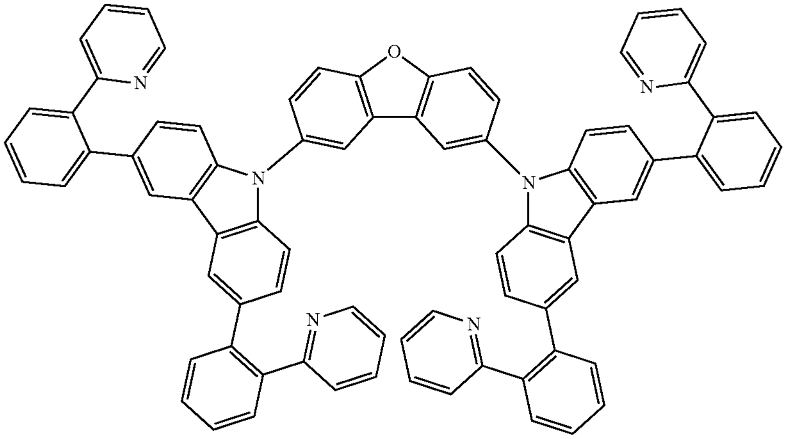
[Chemical formula 12]
6
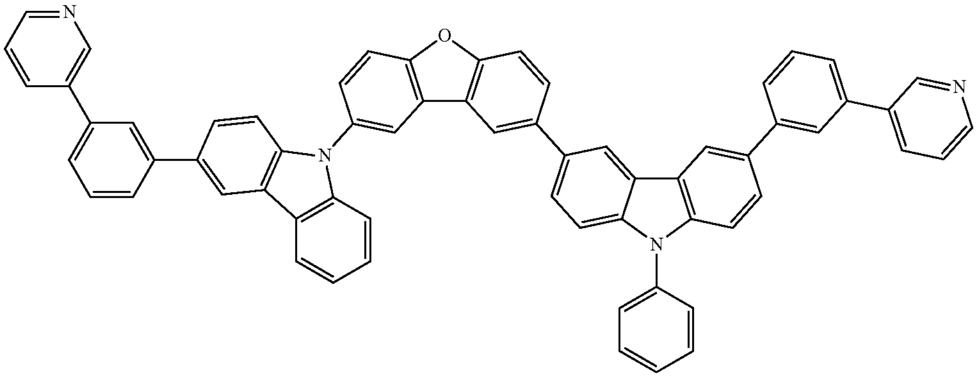
7
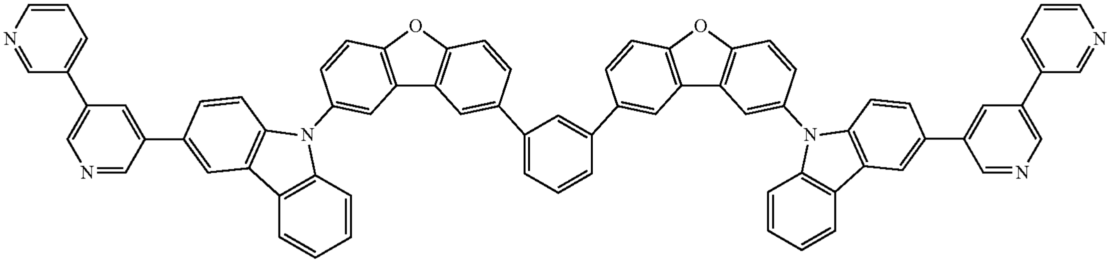

-continued
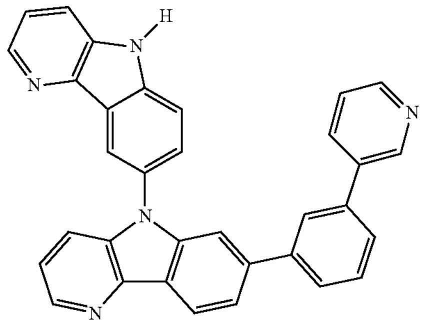
8
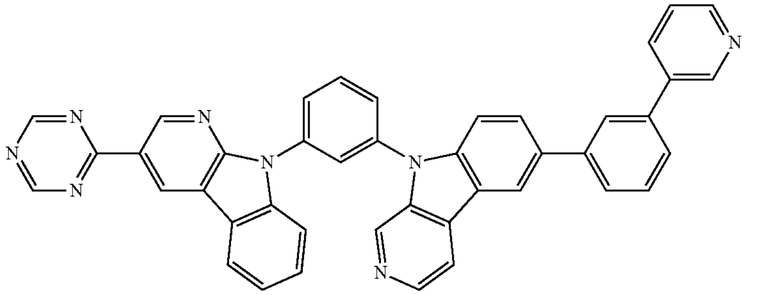
9
[Chemical formula 13]
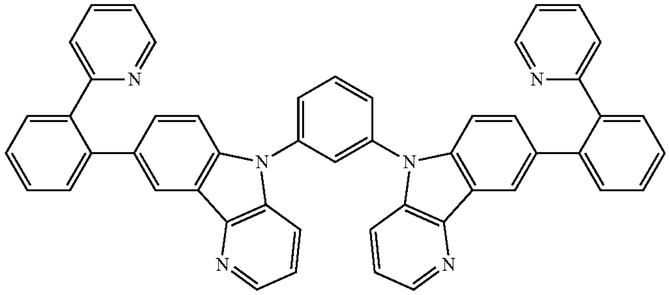
10
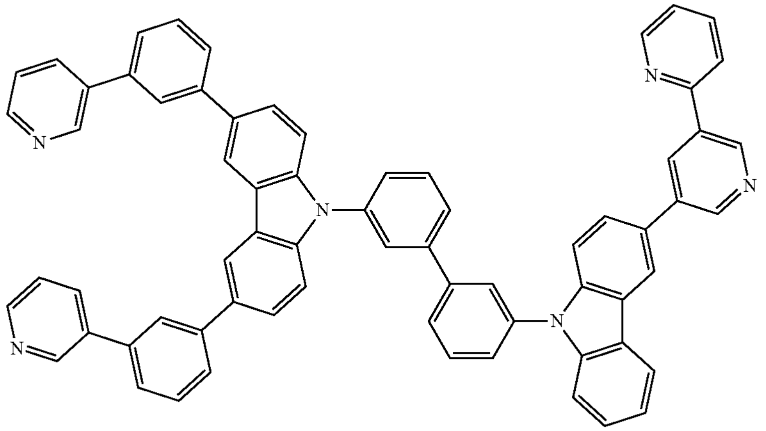
11
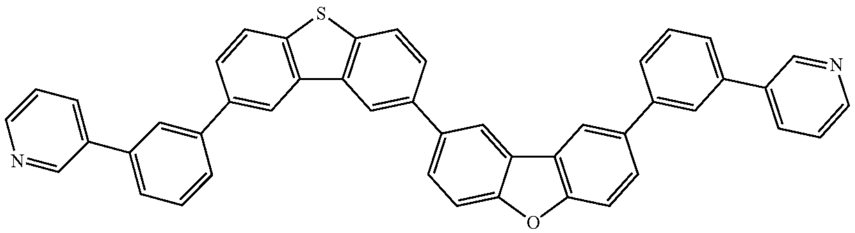
12

-continued
13
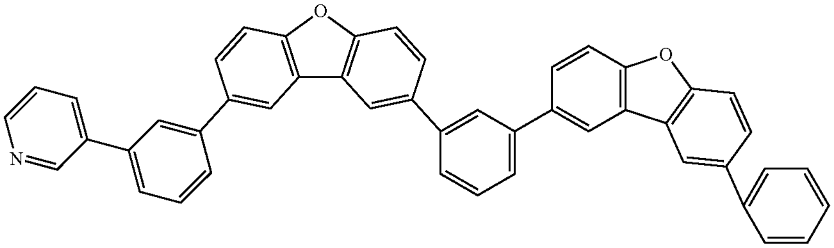
14
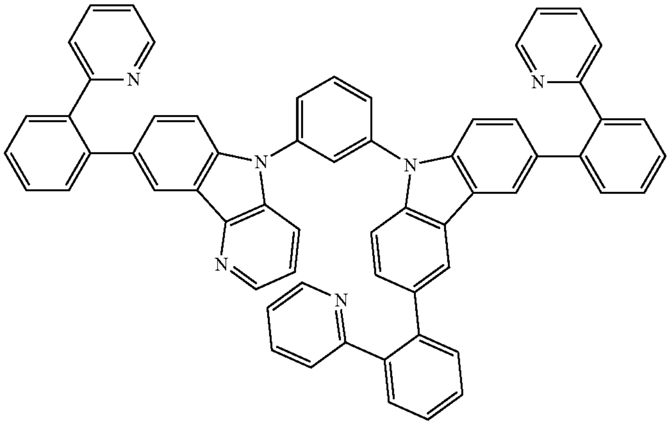
15
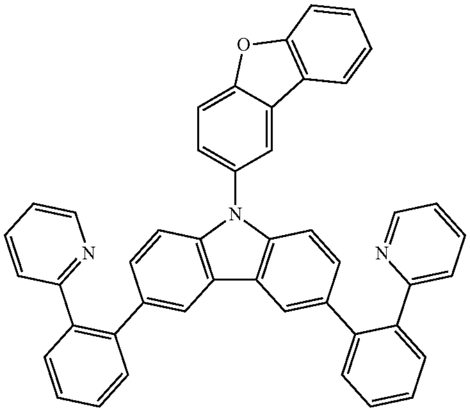
[Chemical formula 14]
16
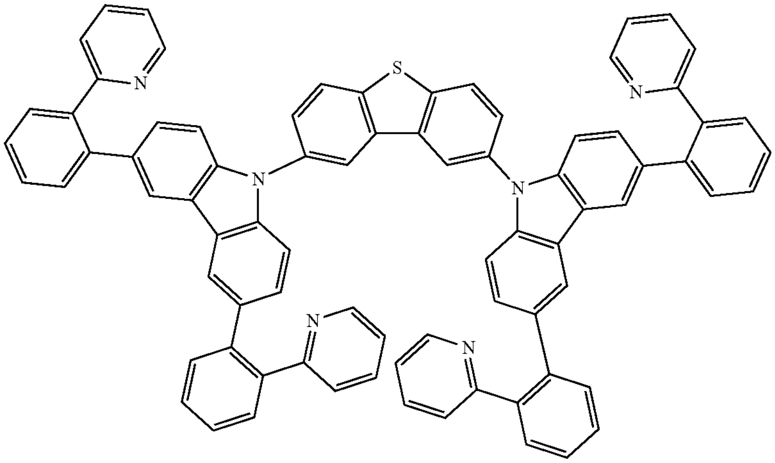

-continued
17
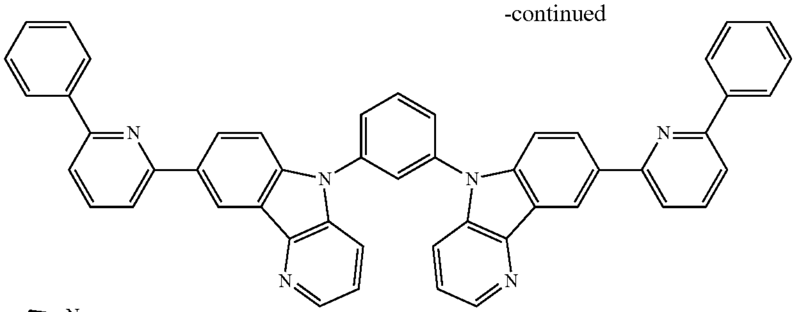
18
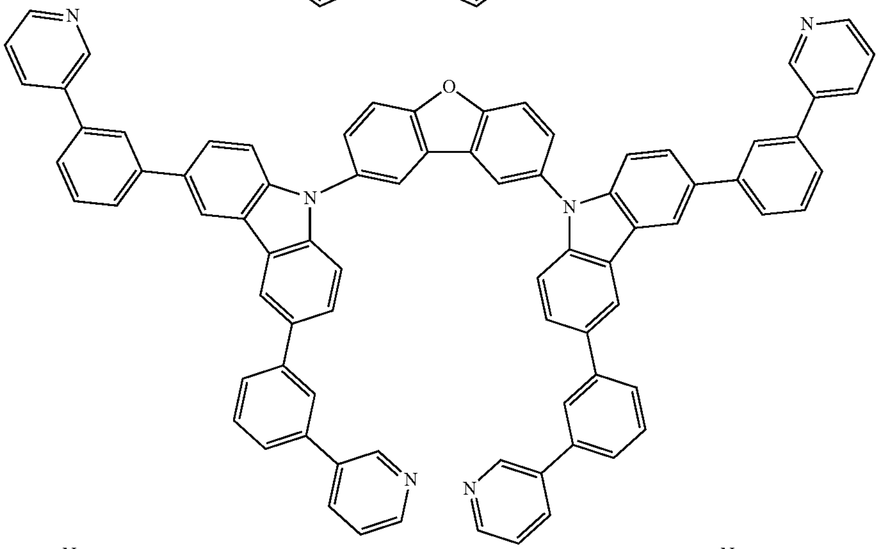
19
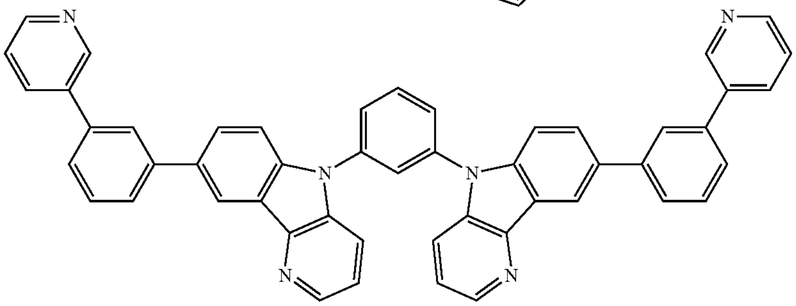
[Chemical formula 15]
20
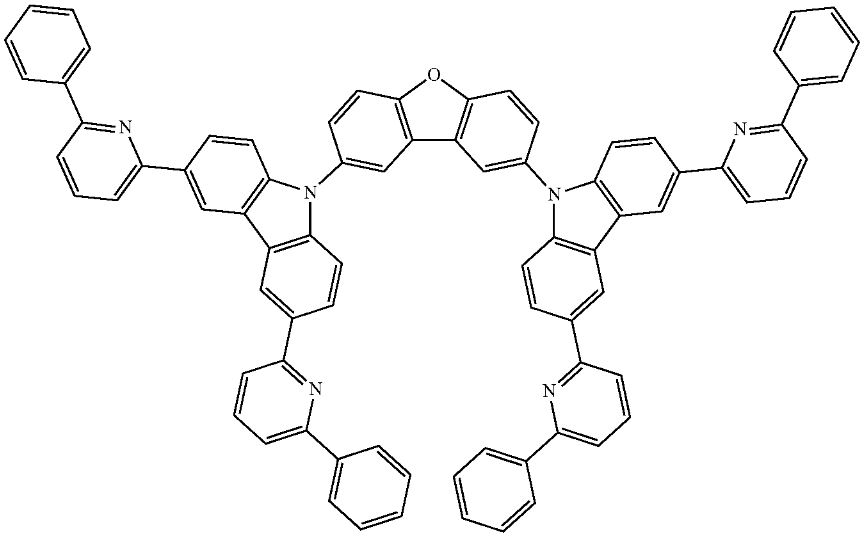

-continued
21
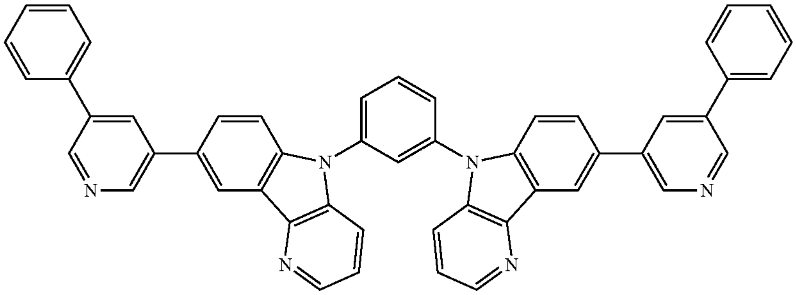
22
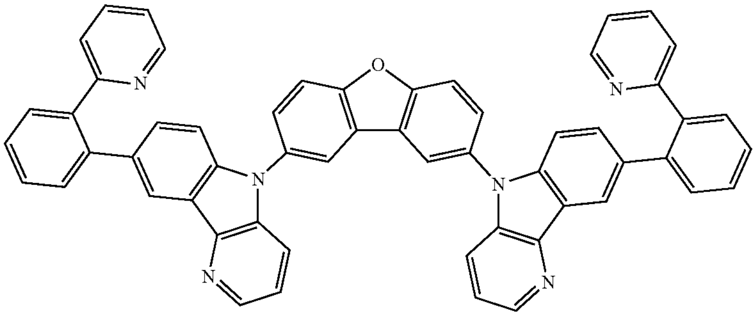
23
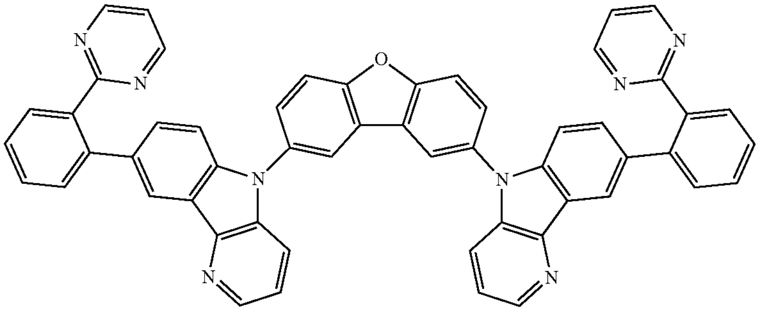
[Chemical formula 16]
24
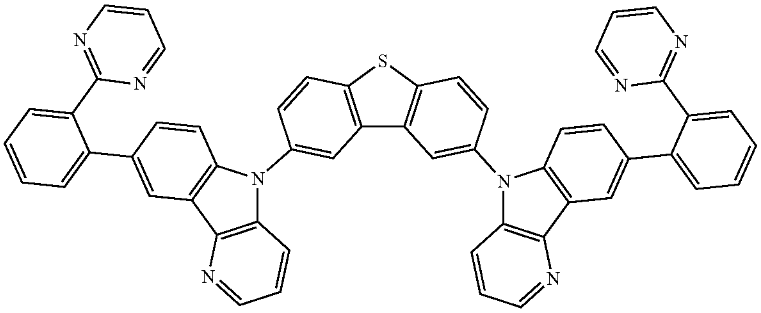
25
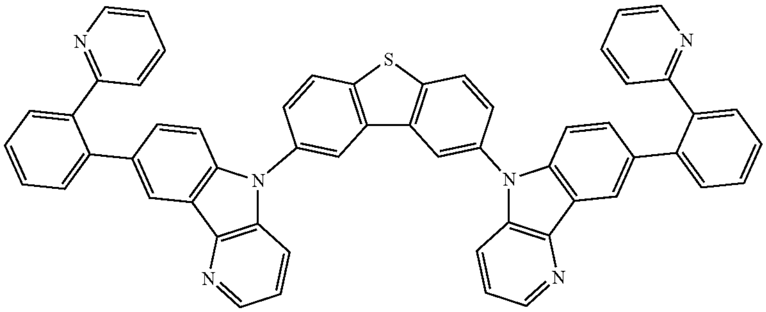

-continued
26
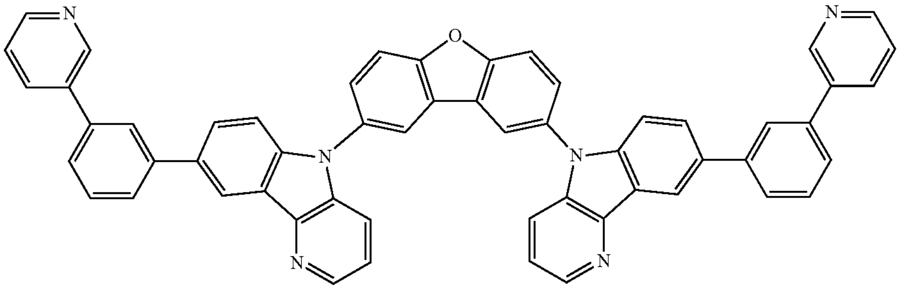
27
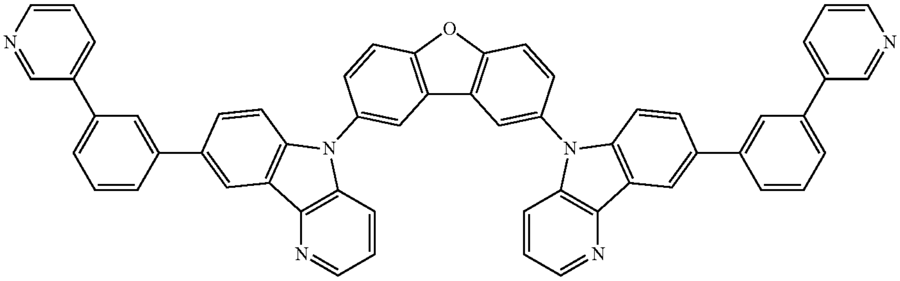
28
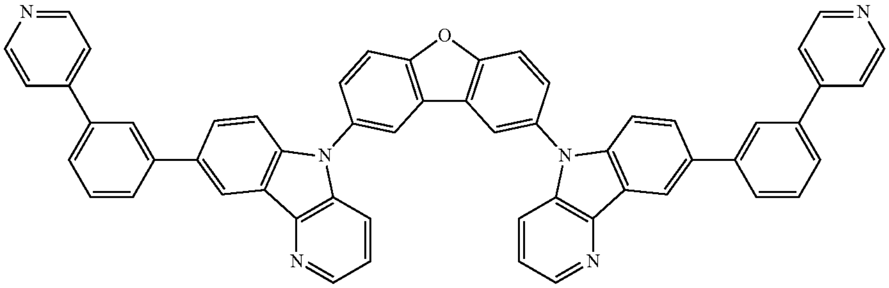
29
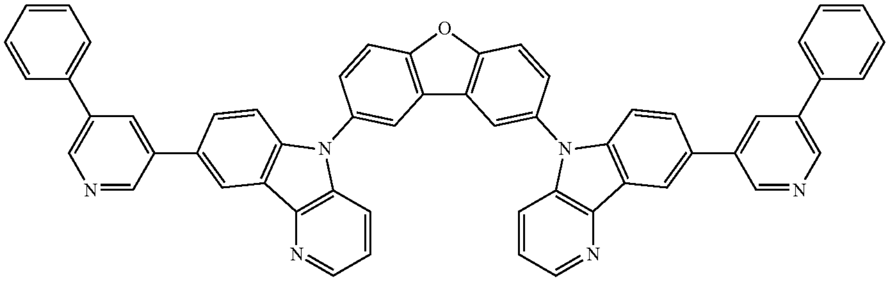
[Chemical formula 17]
30
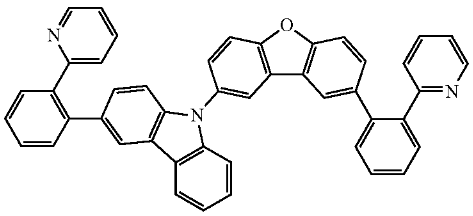
31
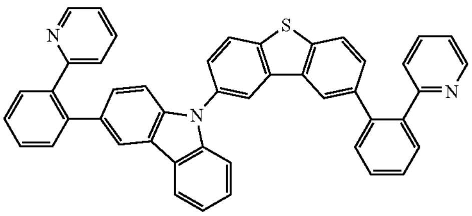

-continued
32
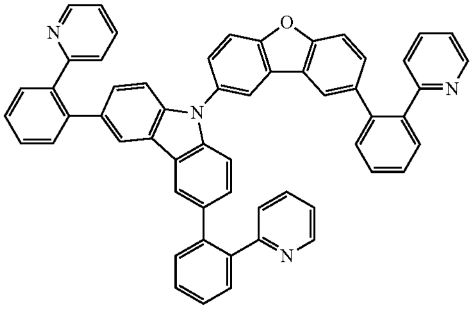
33
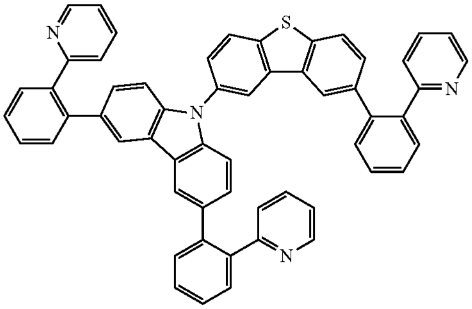
34
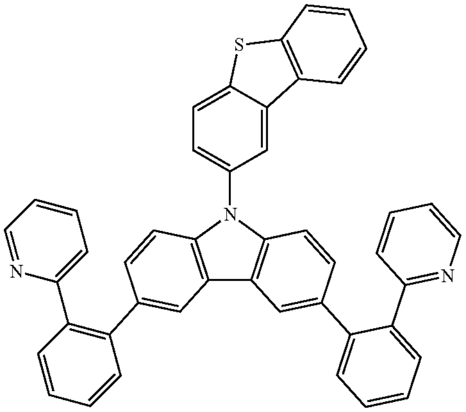
35
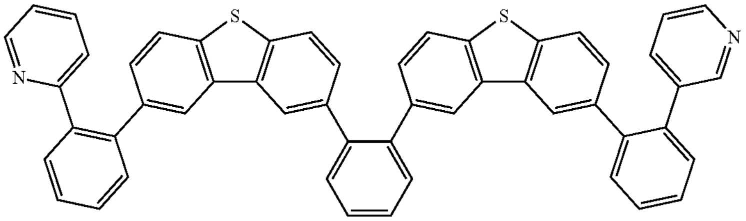
36
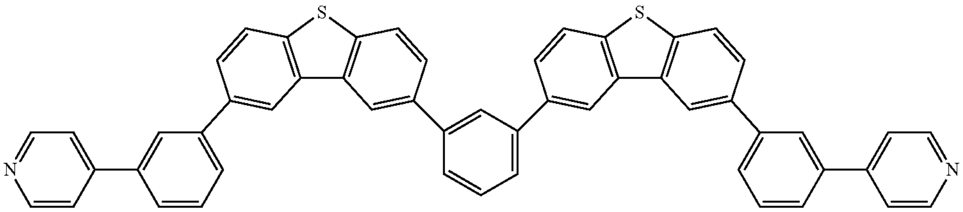
[Chemical formula 18]
37
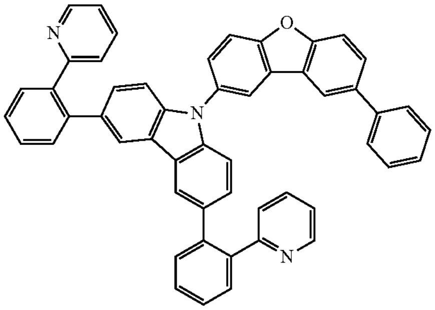
38
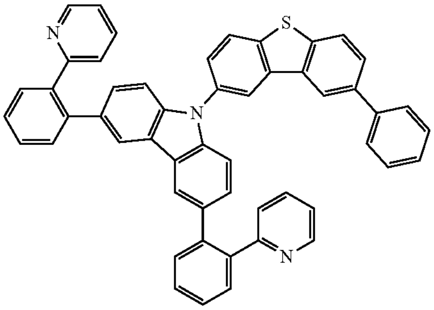

-continued
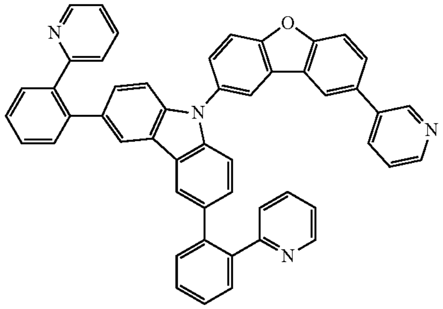
39
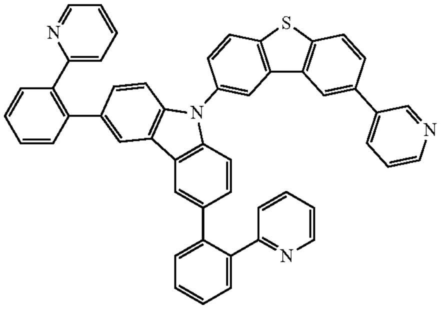
40
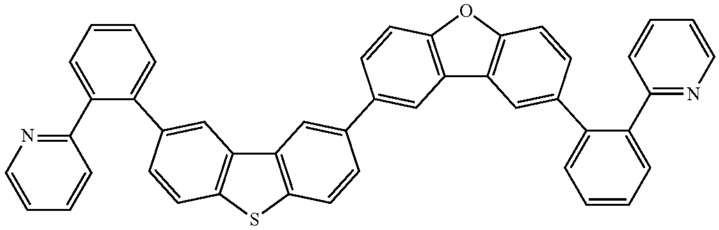
41
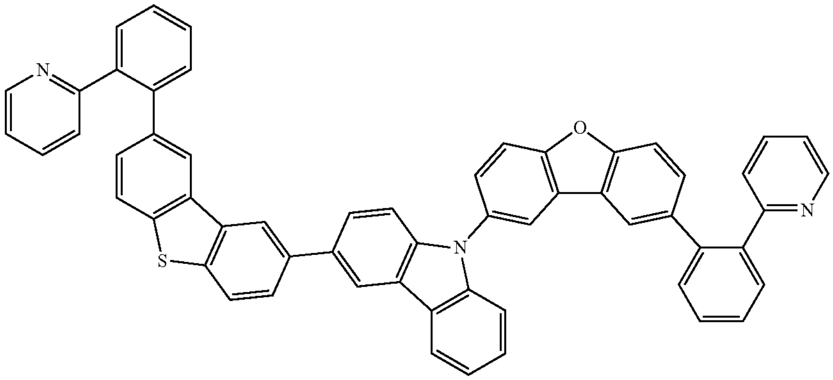
42
[Chemical formula 19]
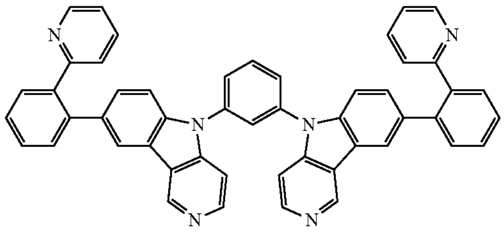
43
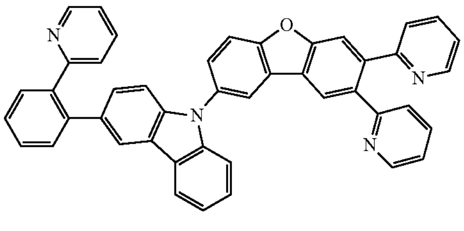
44
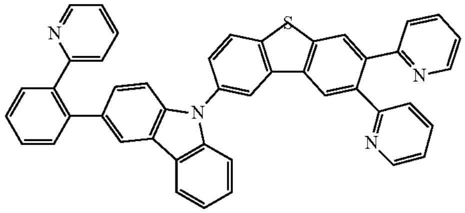
45
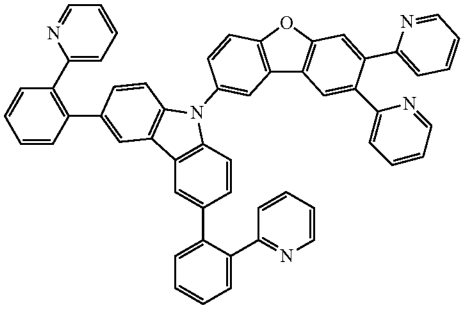
46

-continued
47
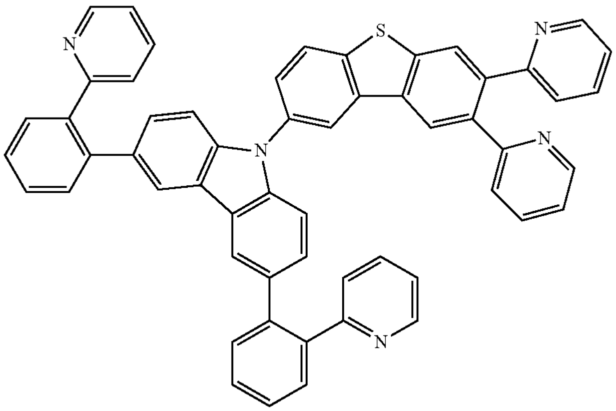
[Chemical formula 20]
48
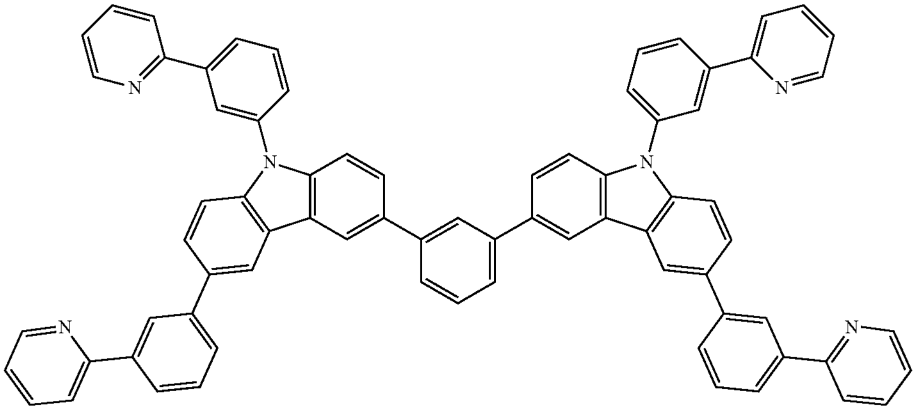
49
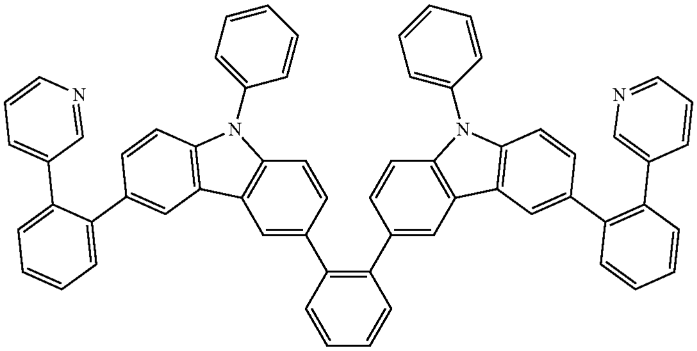
50
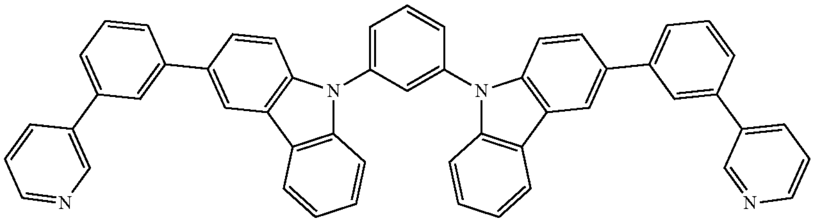

-continued
51
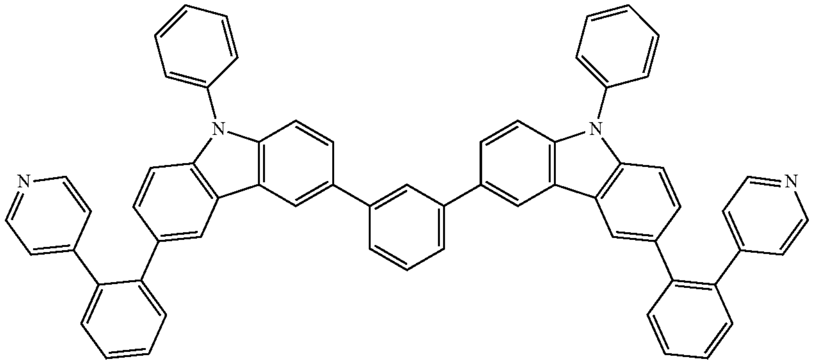
52
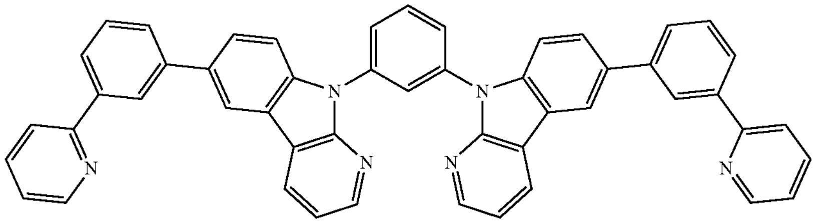
[Chemical formula 21]
53
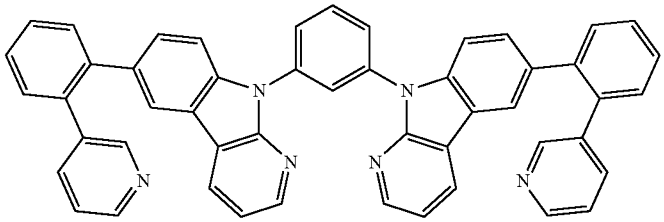
54
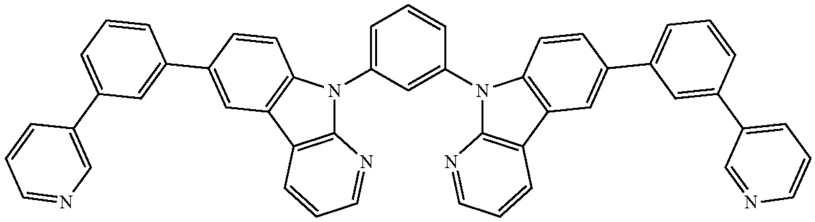
55
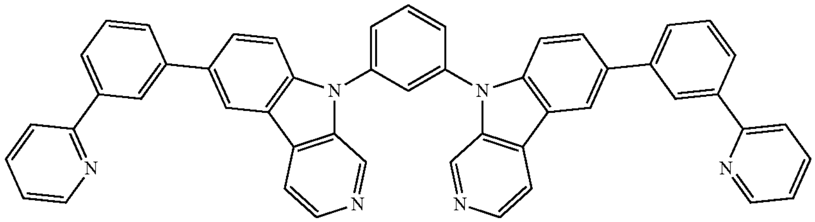
56
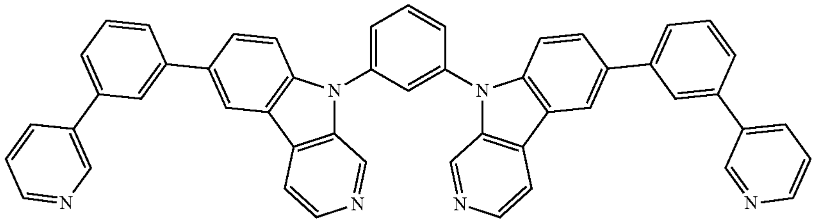

-continued
57
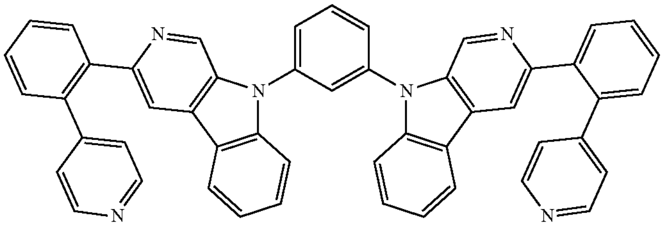
58
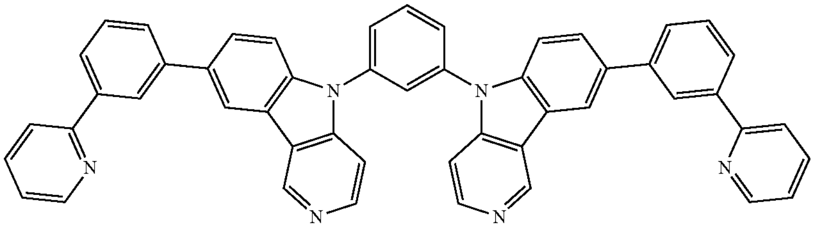
[Chemical formula 22]
59
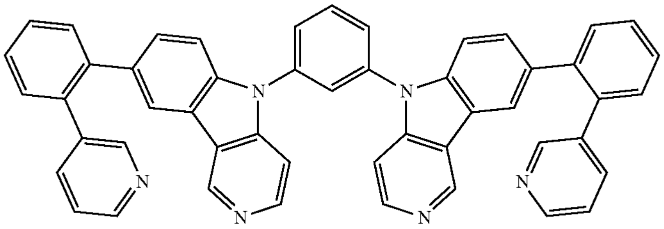
60
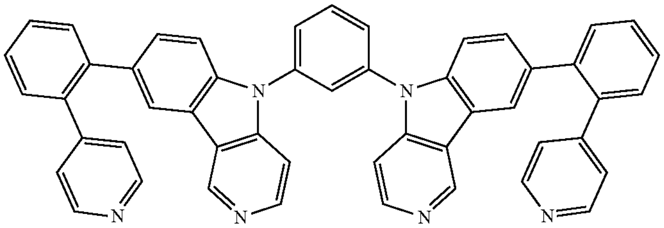
61
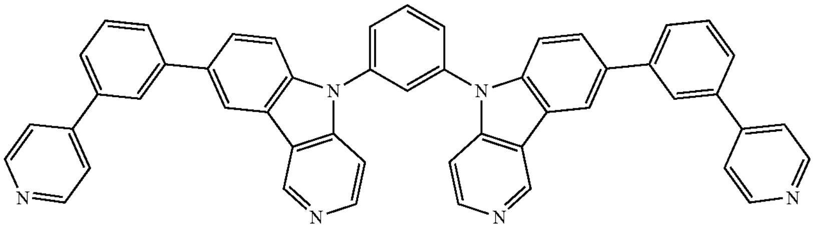
62
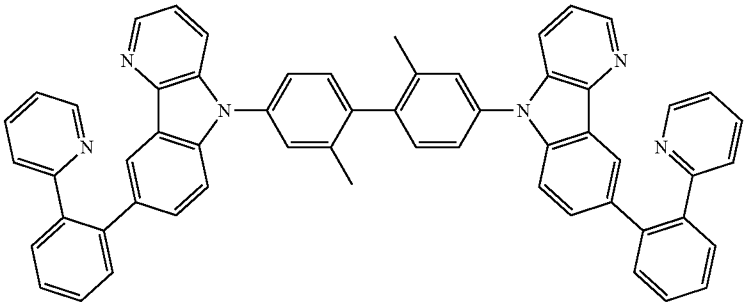

-continued
63
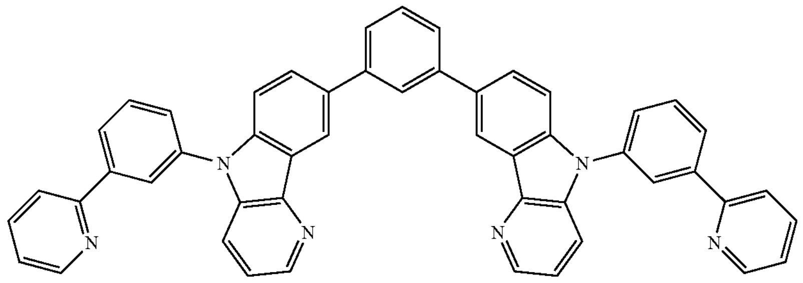
64
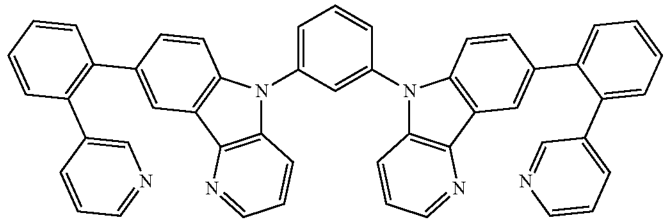
[Chemical formula 23]
65
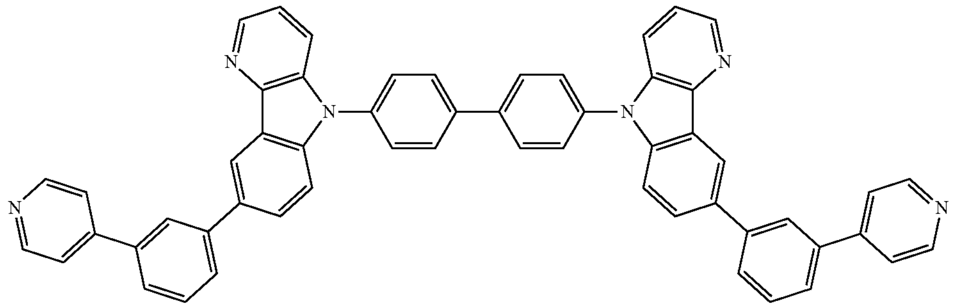
66
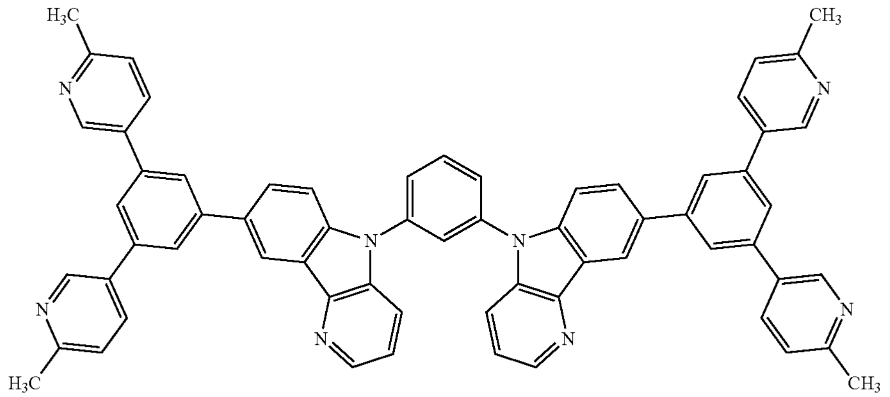

-continued
67
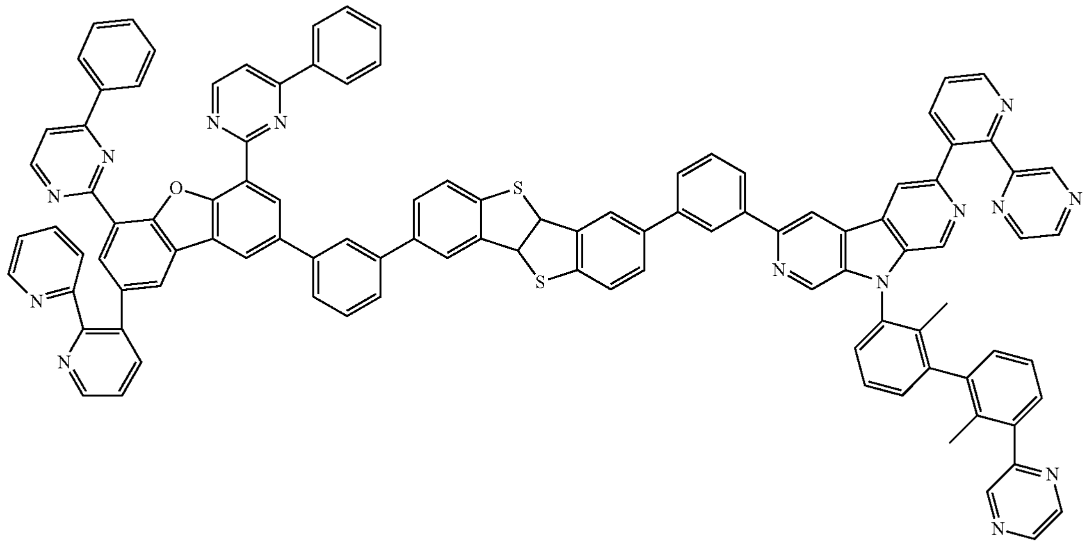
[Chemical formula 24]
68
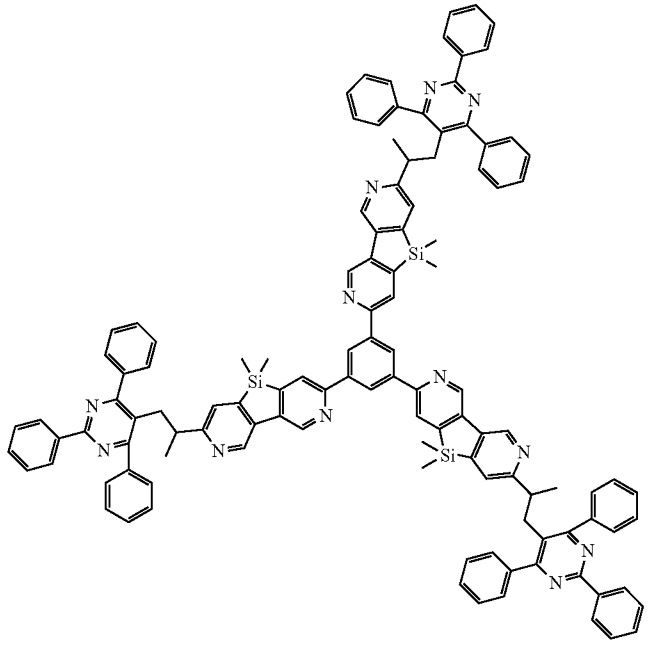

-continued
69
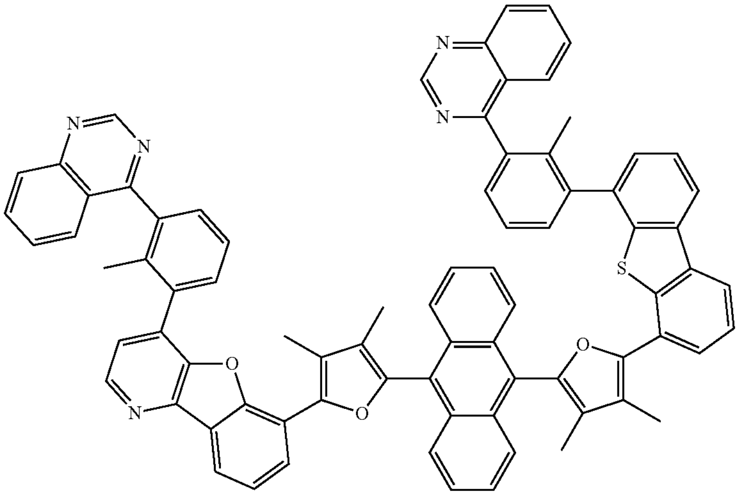
[Chemical formula 25]
70
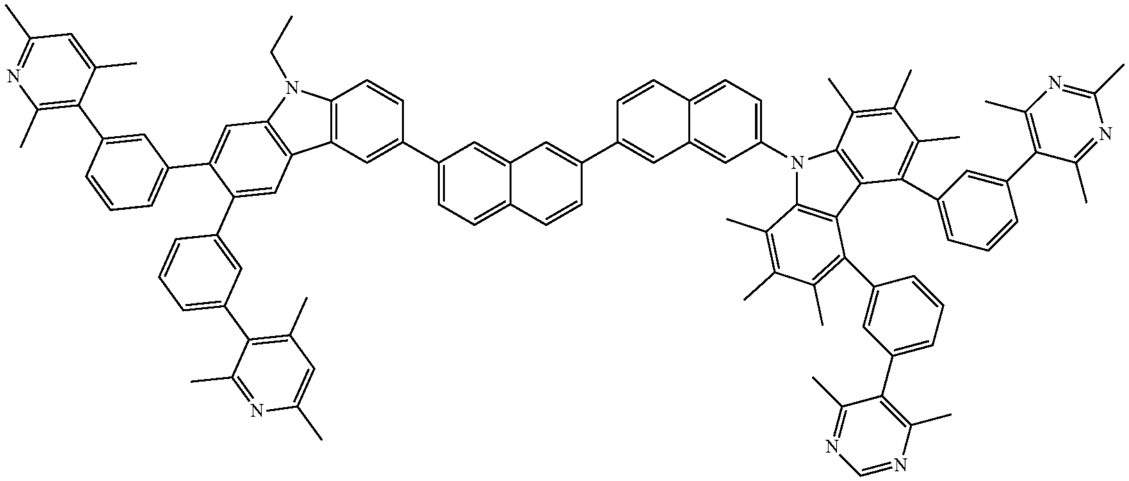
71
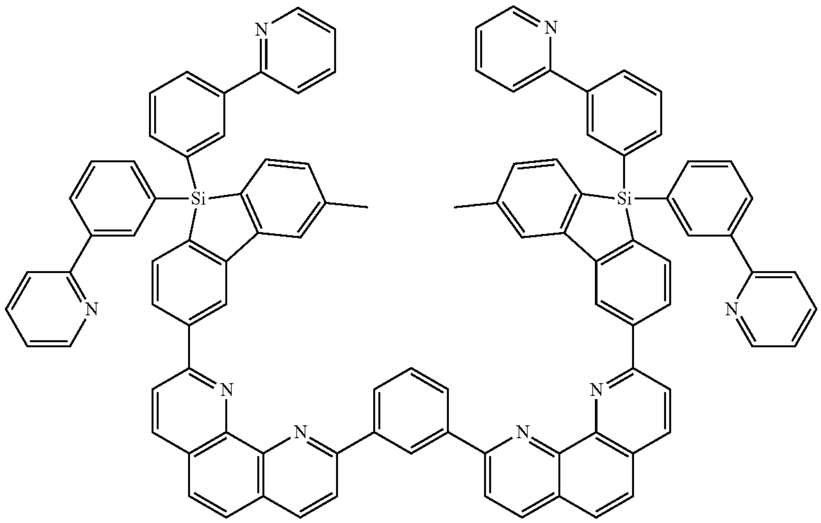

-continued
72
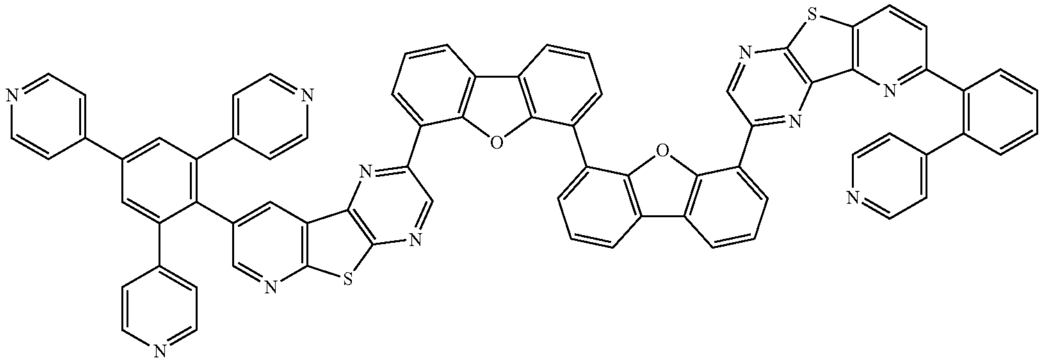
[Chemical formula 26]
73
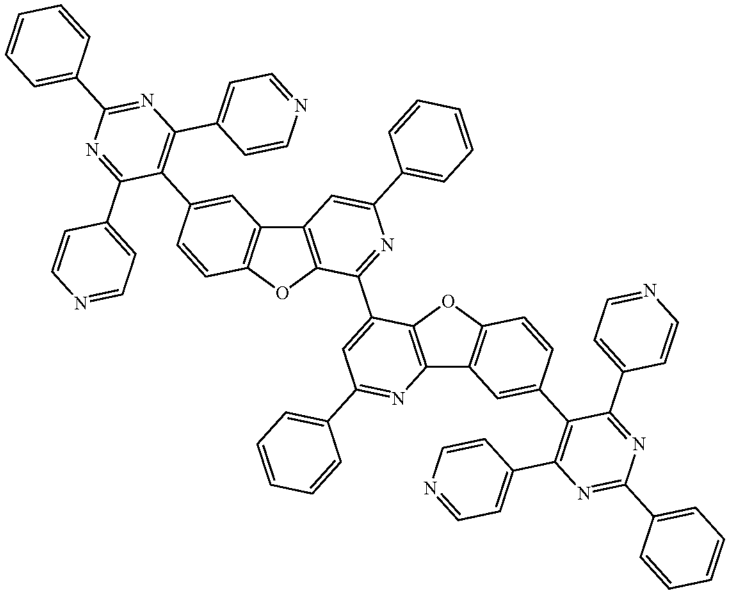
74
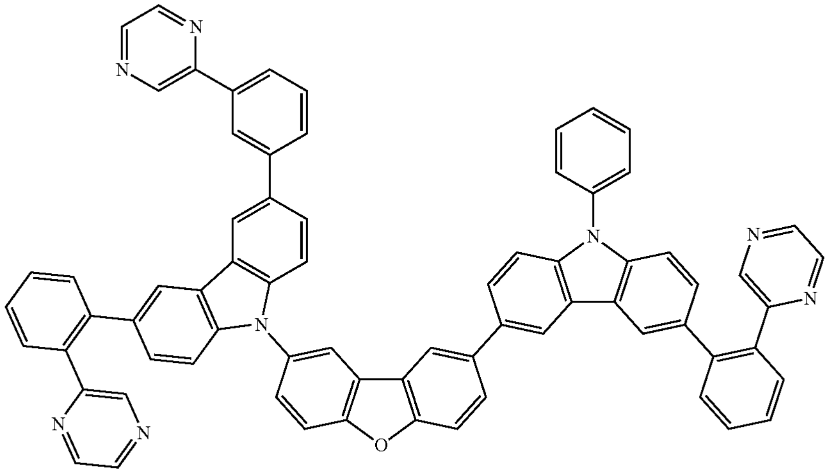

-continued
75
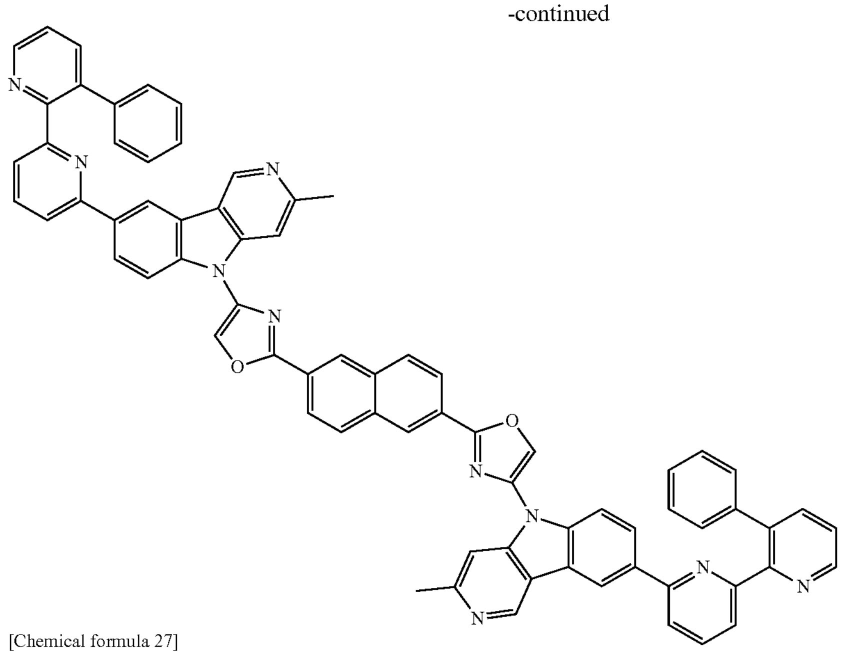
[Chemical formula 27]
76
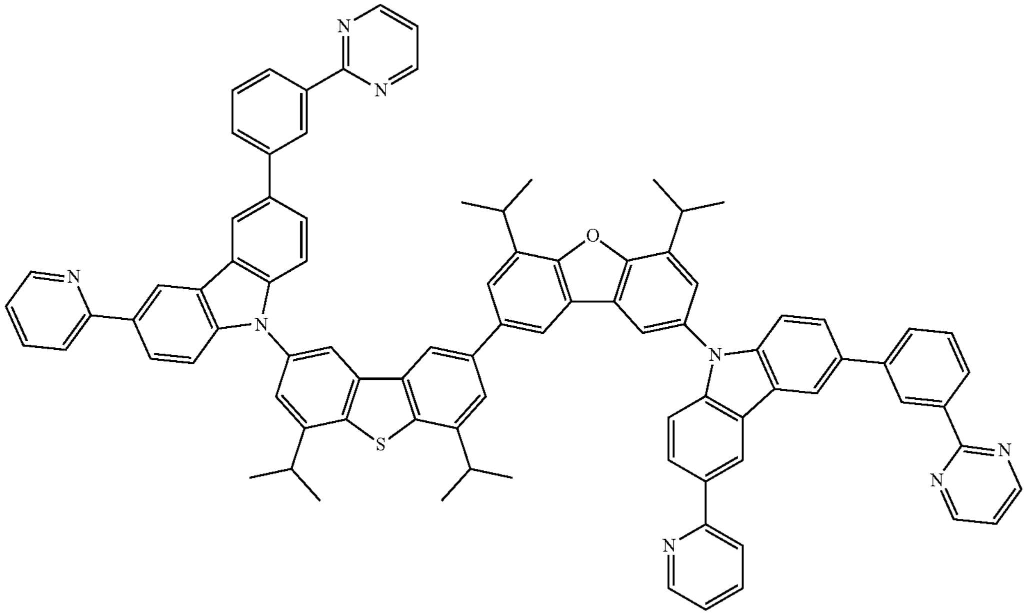
77
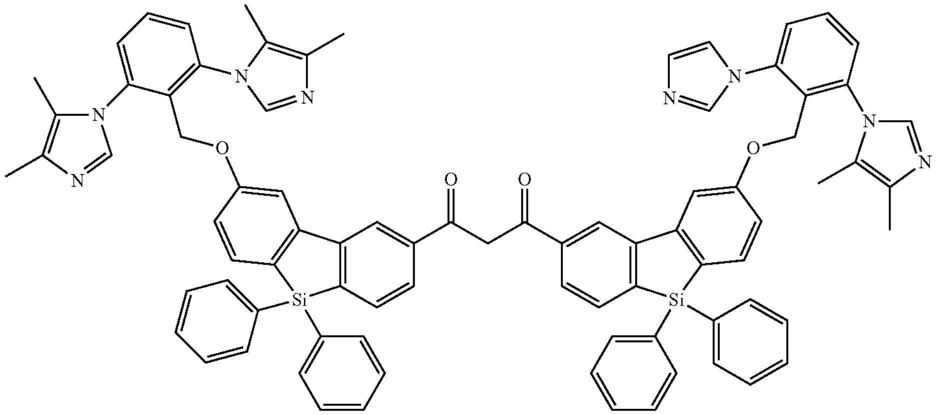

-continued
78
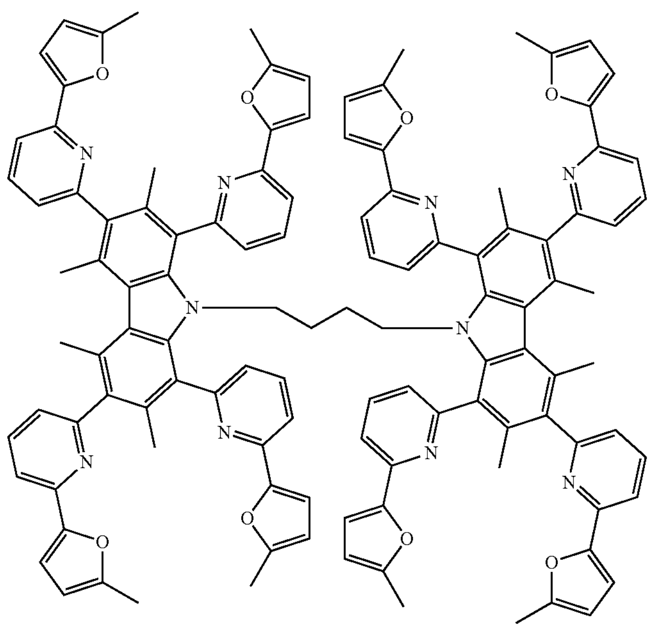
[Chemical formula 28]
79
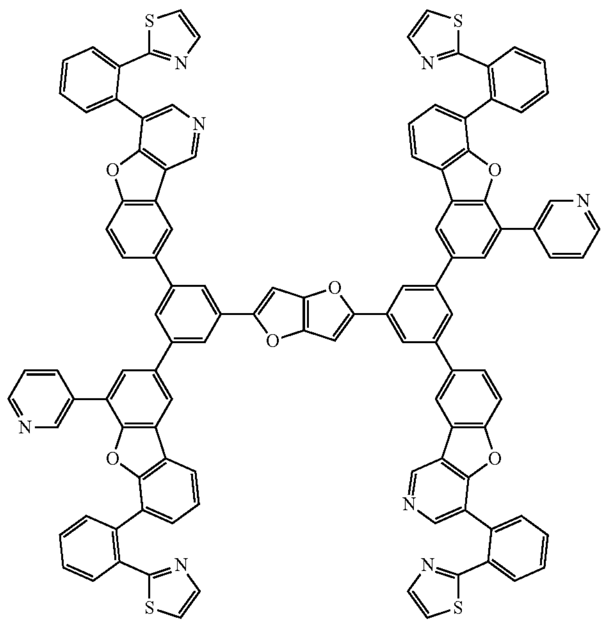

-continued
80
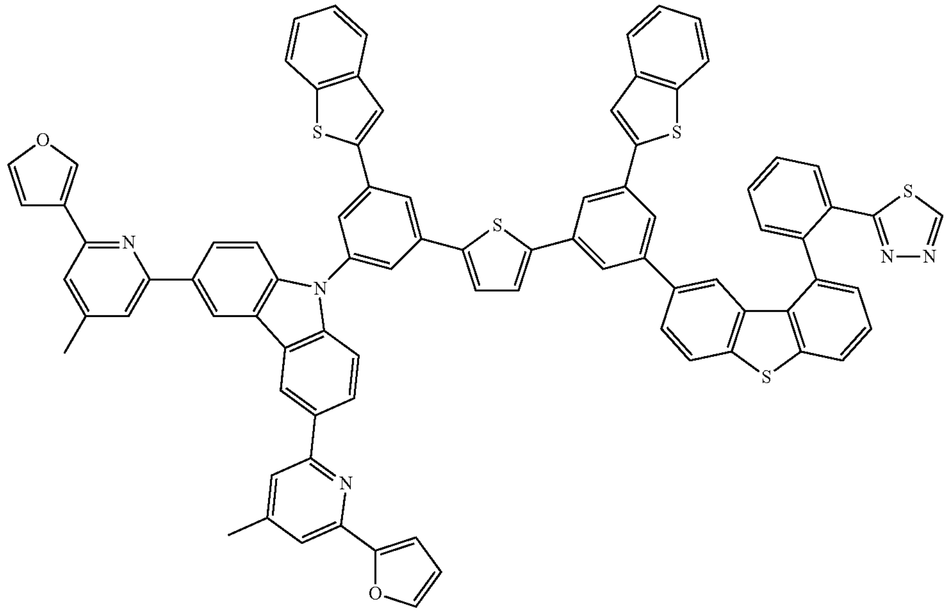
[Cehmical formula 29]
81
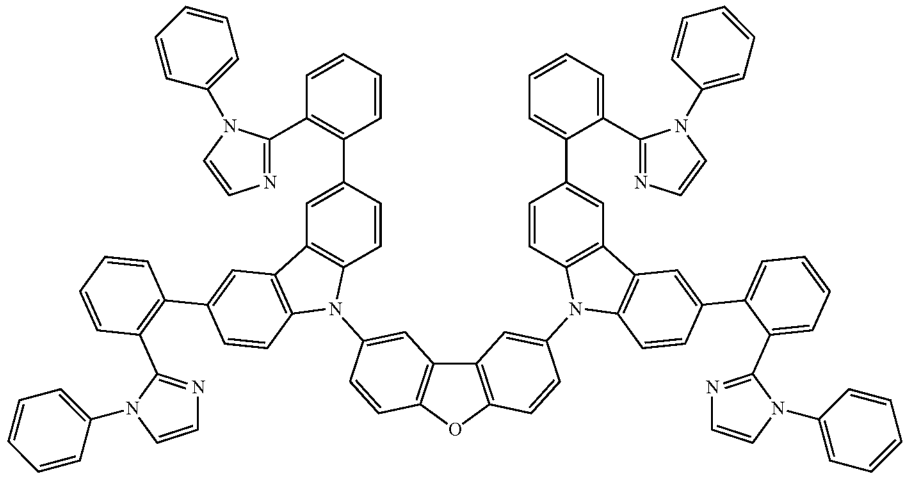
82
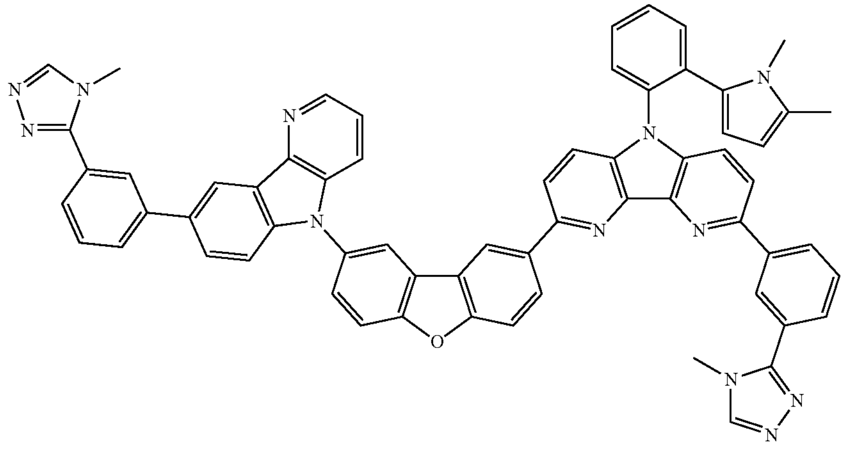

-continued
83
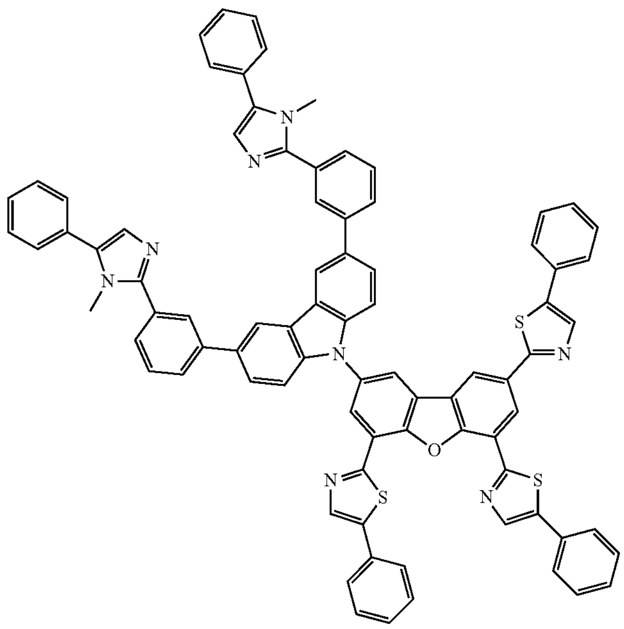
[Chemical formula 30]
84
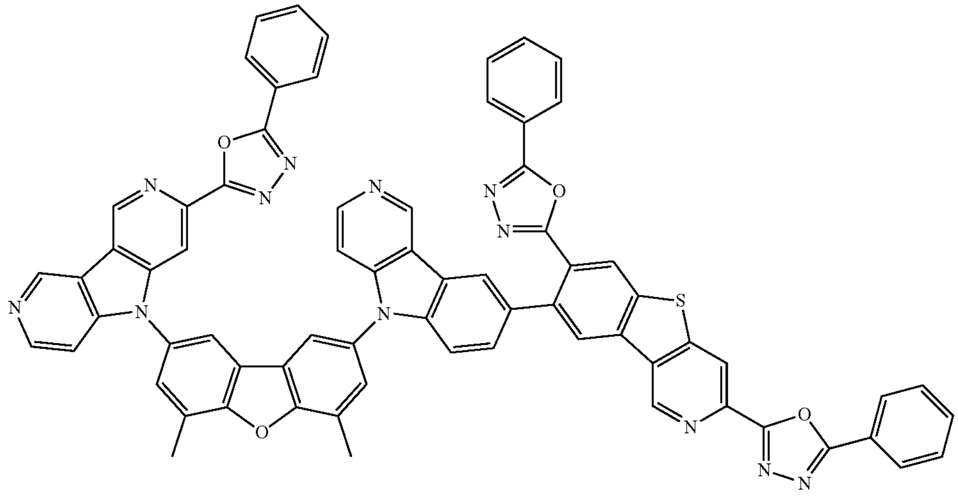

-continued
85
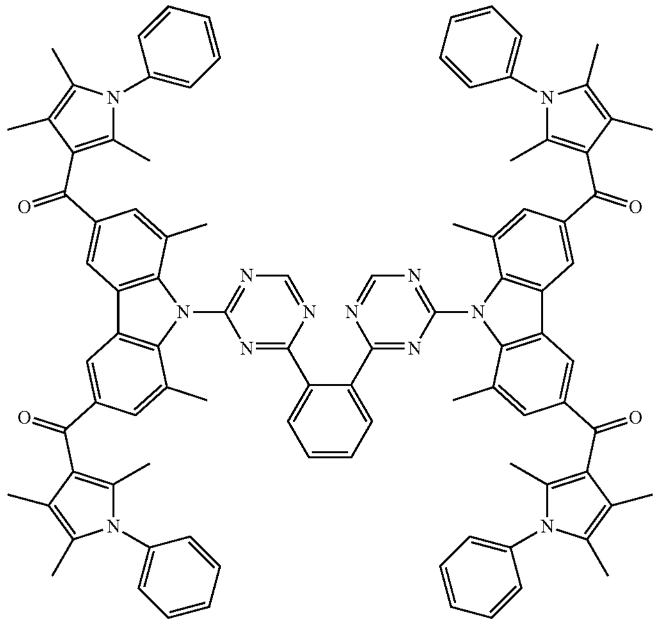
[Chemical formula 31]
86
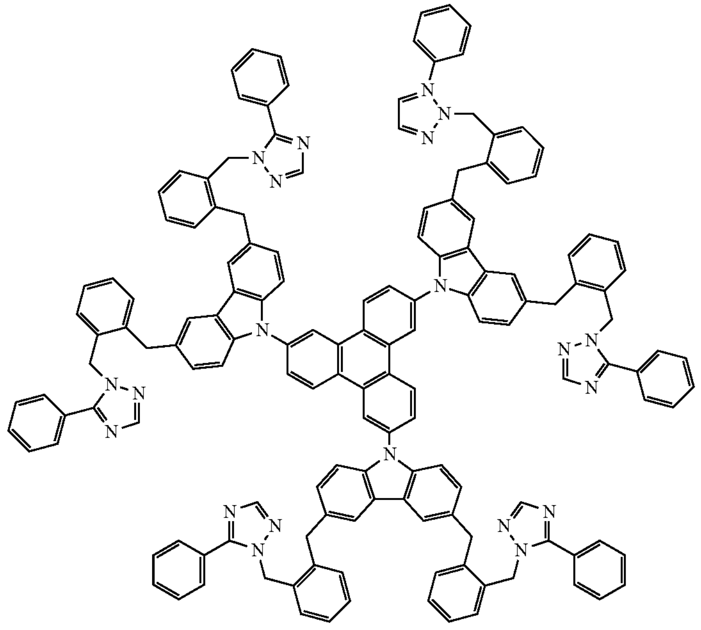

-continued
87
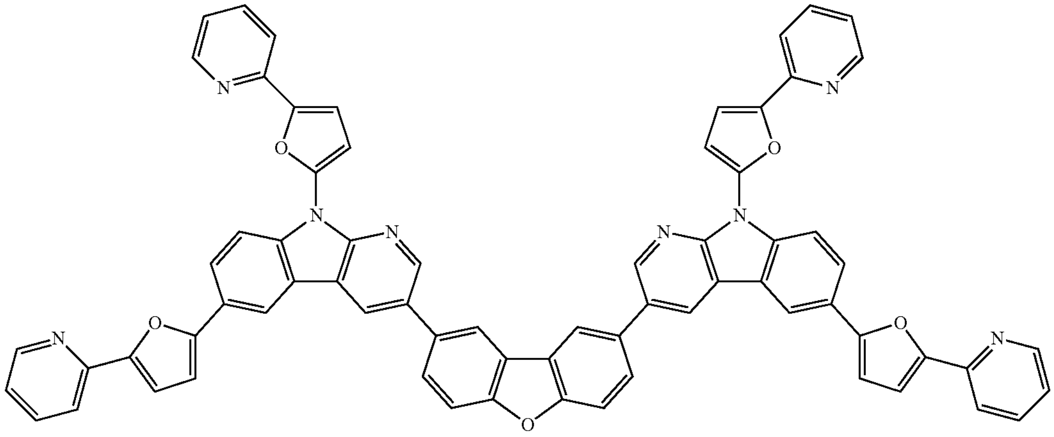
88
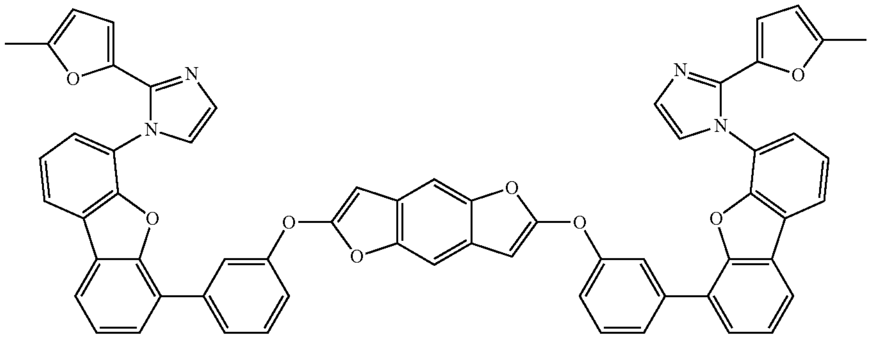
[Chemical formula 32]
89
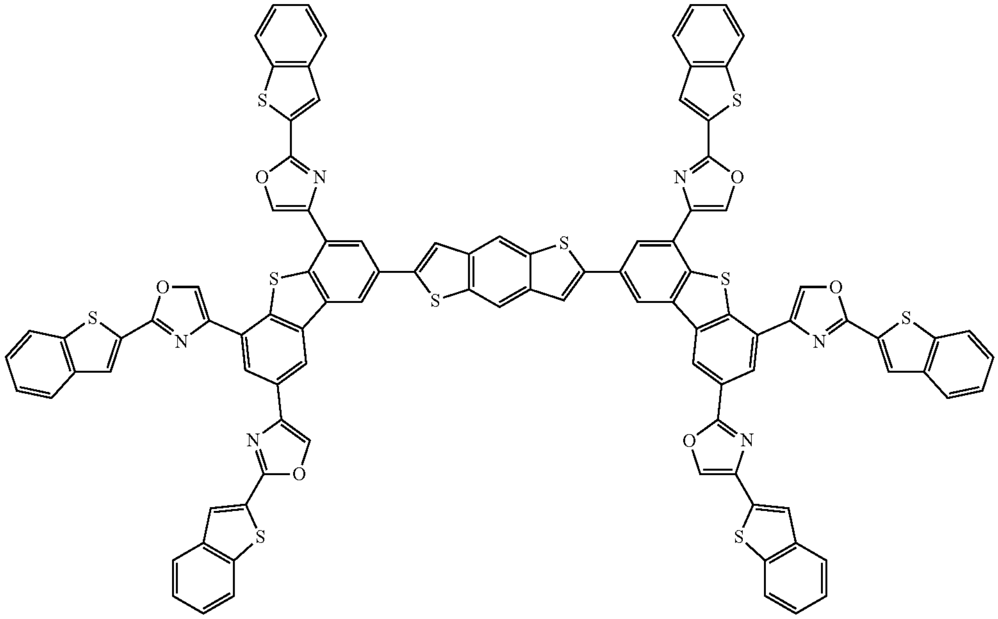

-continued
90
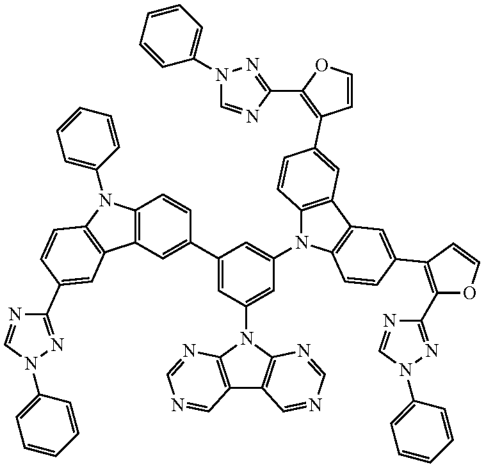
91
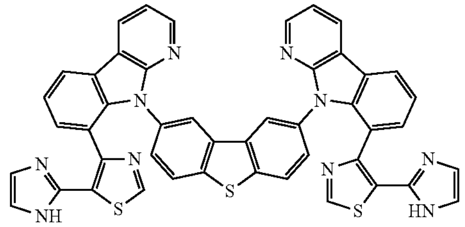
[Chemical formula 33]
92
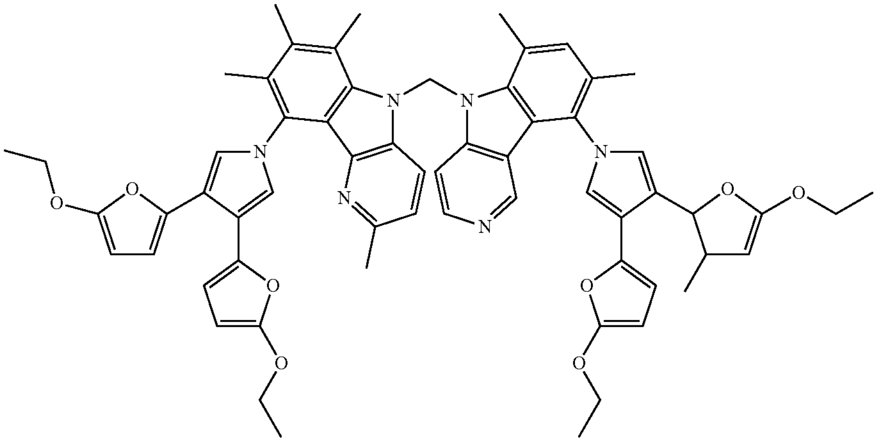
93
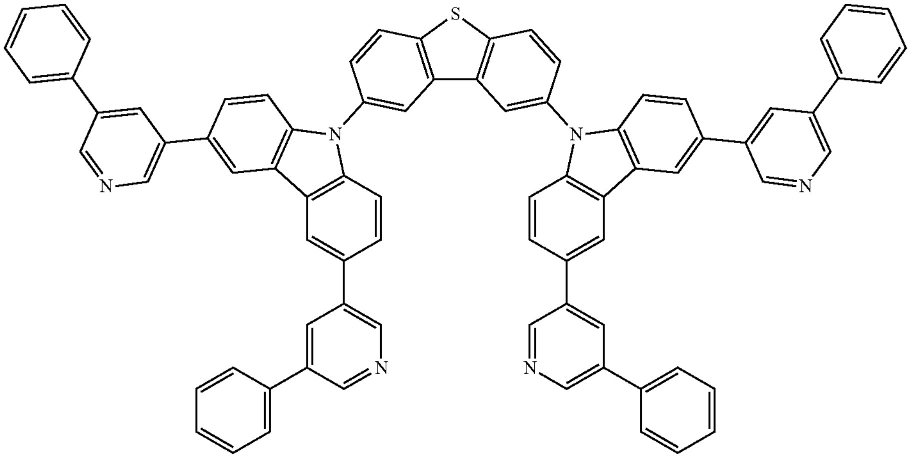

-continued
94
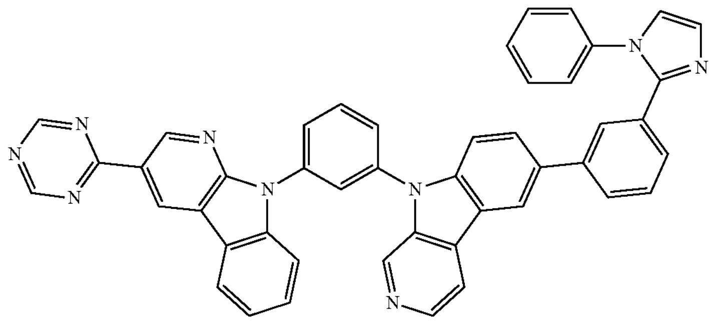
95
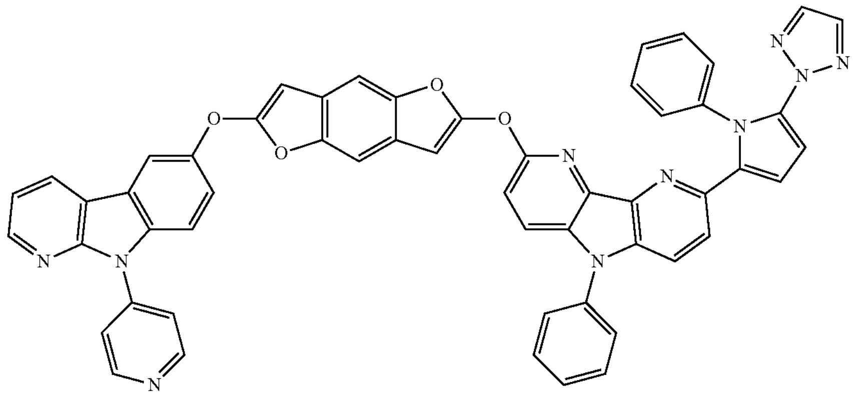
[Chemical formula 34]
96
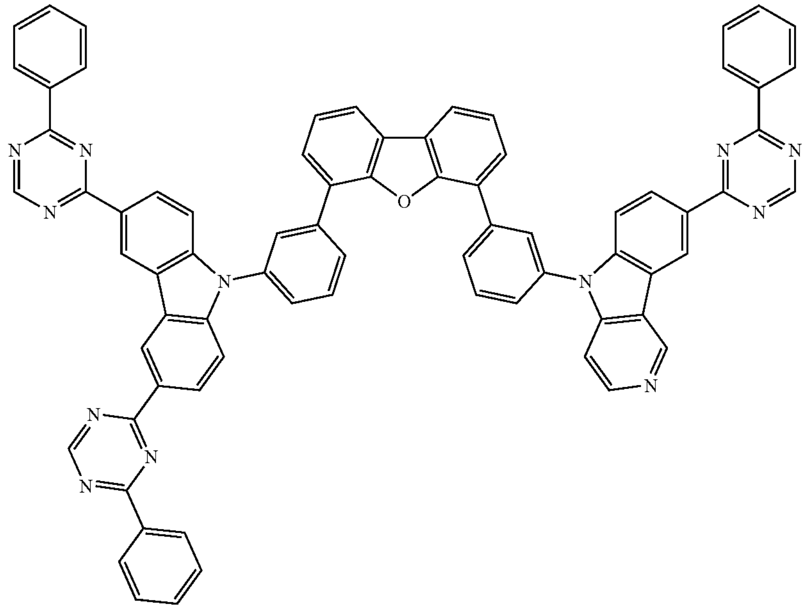

-continued
97
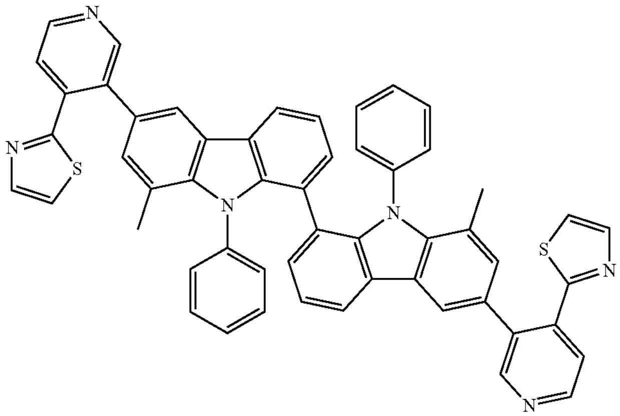
98
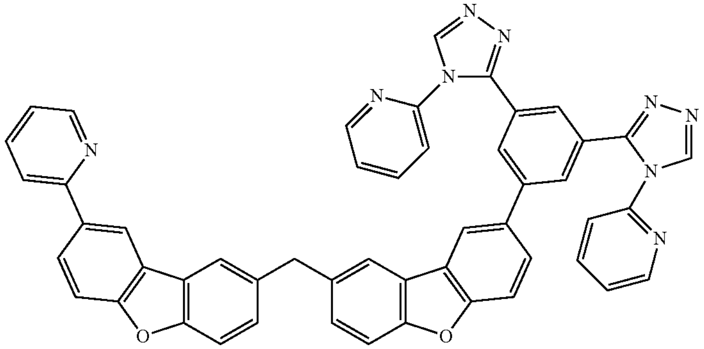
99
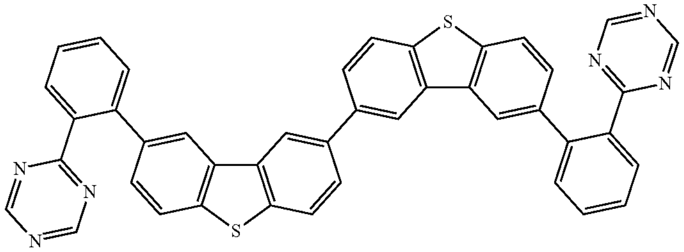
[Chemical formula 35]
100
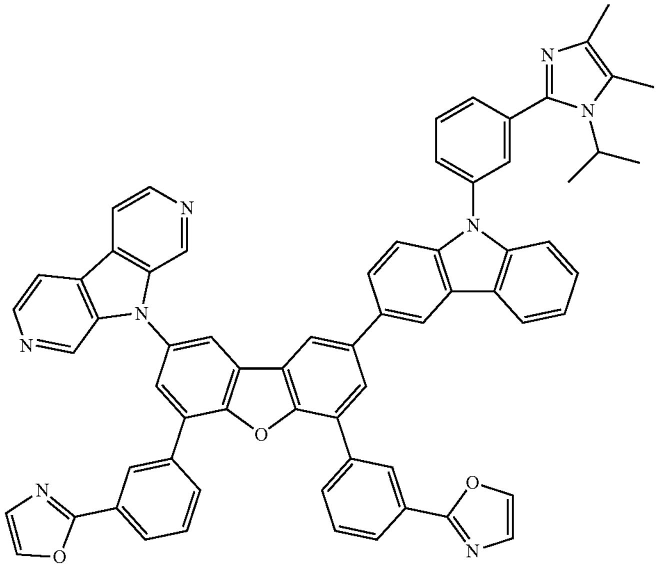

-continued
101
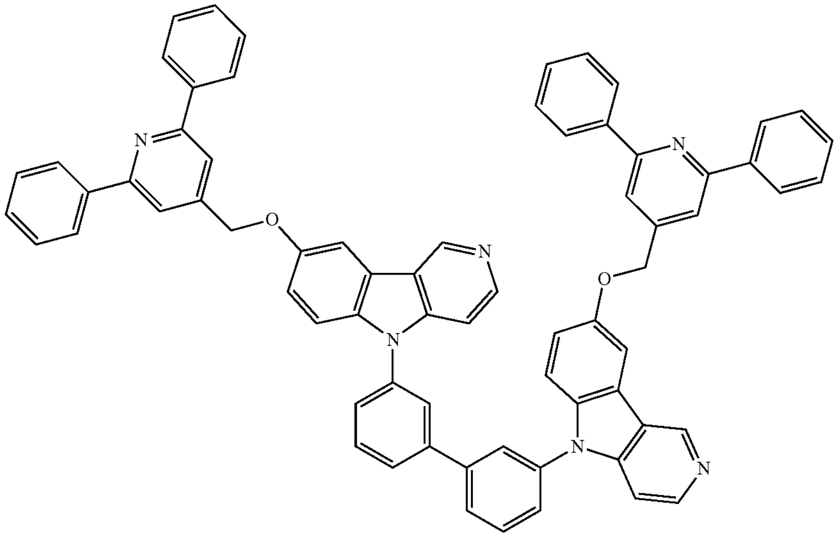
102
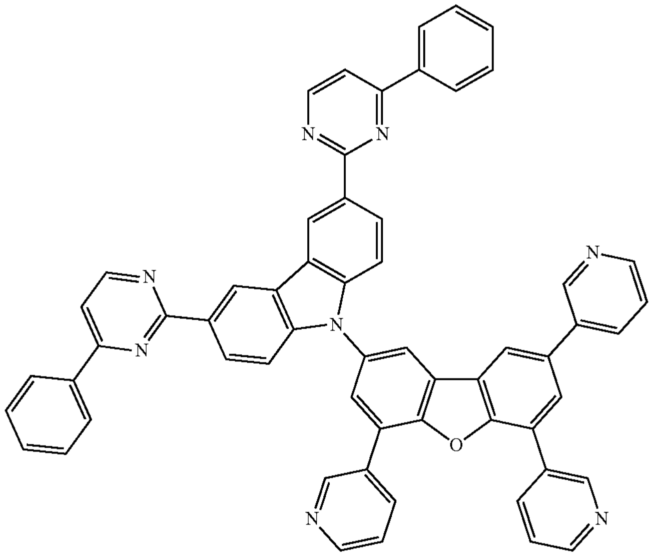
[Chemical formula 36]
103
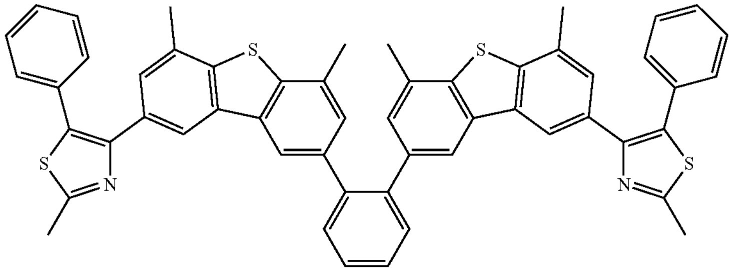

-continued
104
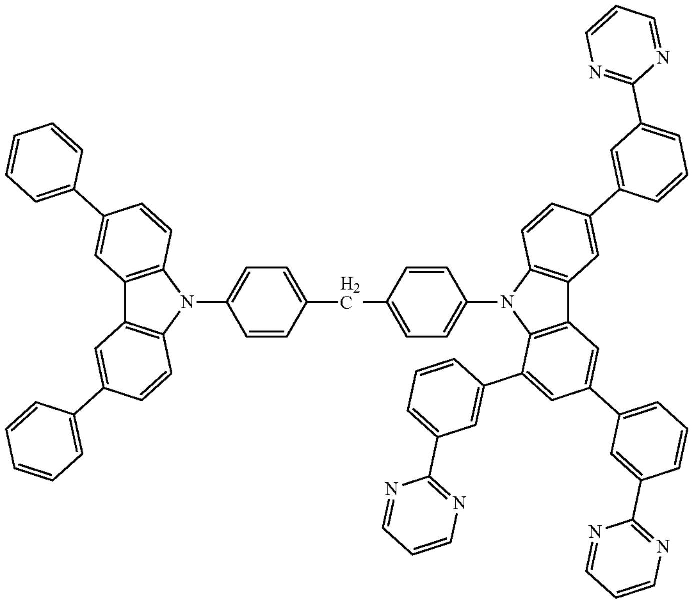
105
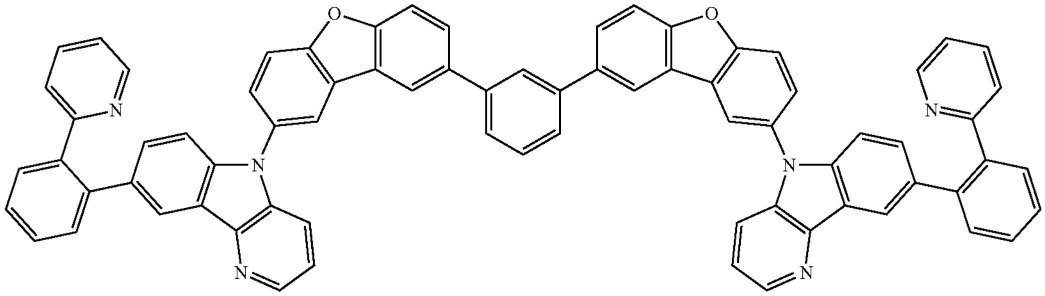
106
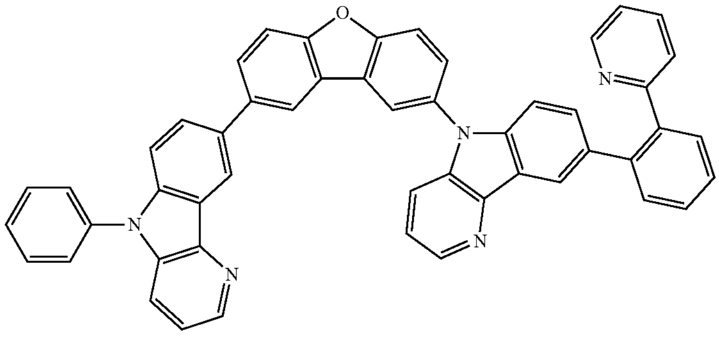

-continued
[Chemical formula 37]
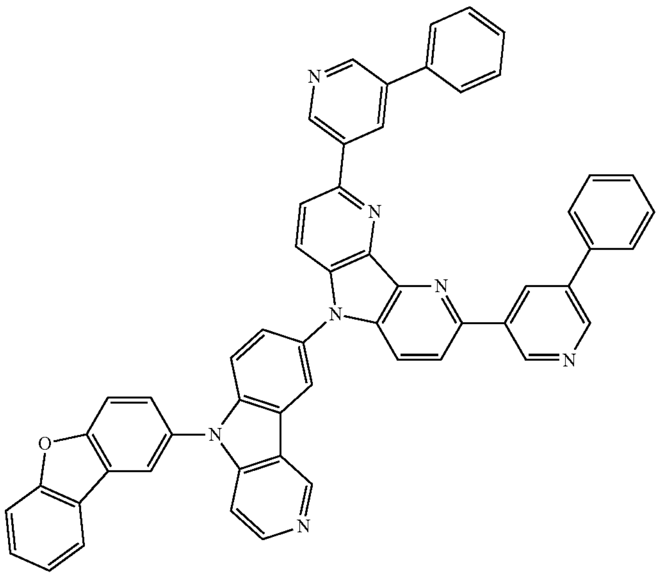
107
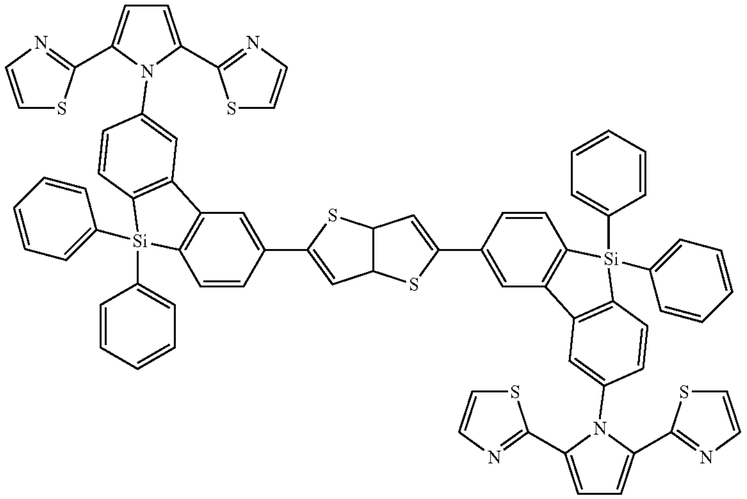
108
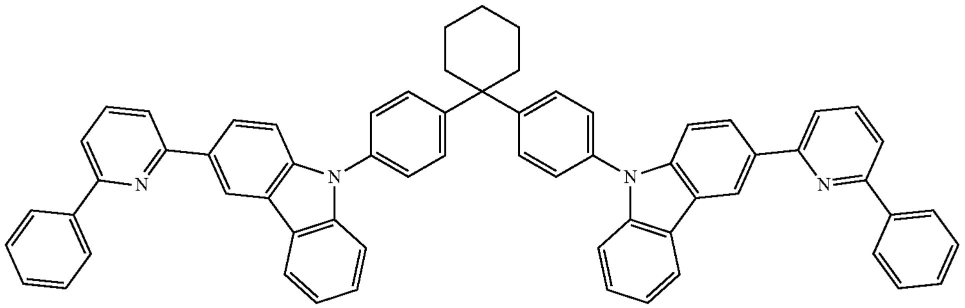
109

-continued
[Chemical formula 38]
110
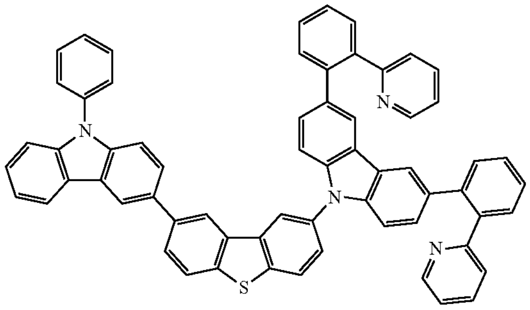
111
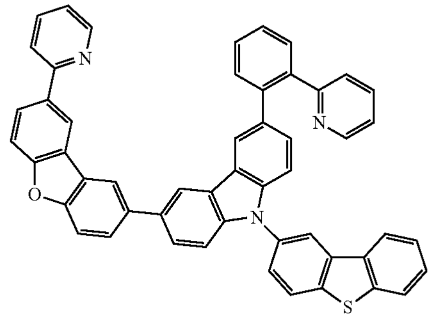
112
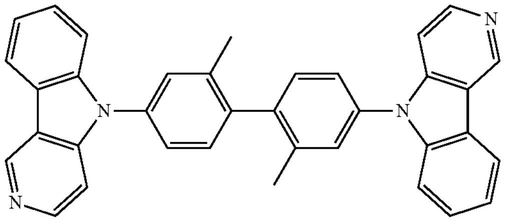
(1.5) Example of Synthesis of Compound
Hereinafter, a specific example of synthesis of illustrative compound 5 will be shown as a non-limiting example of synthesis of a typical compound.
[Chemical formula 39]
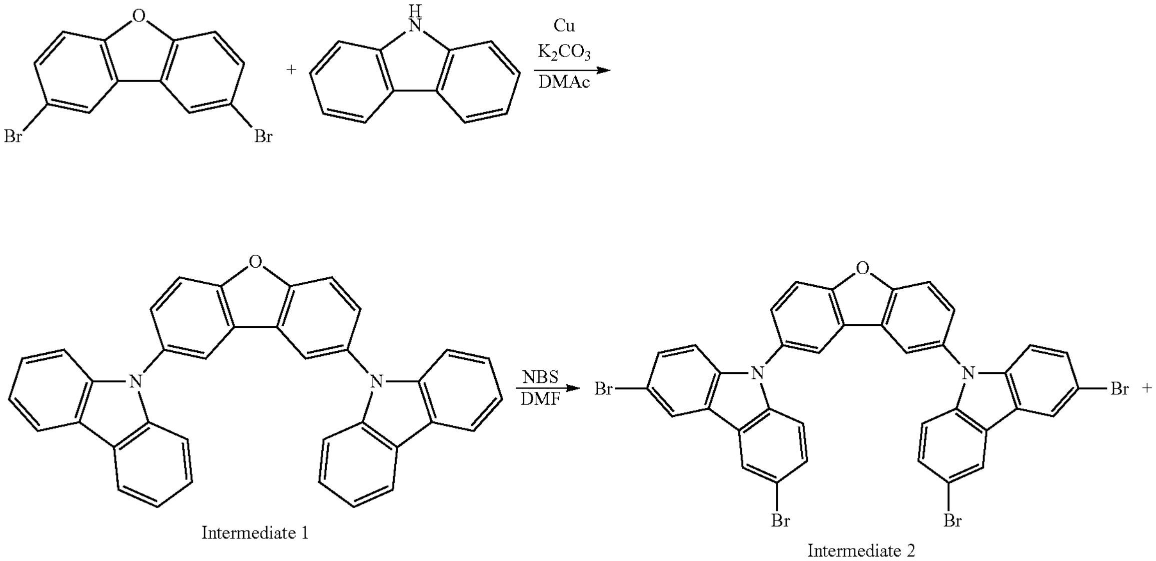
Intermediate 1
Intermediate 2

-continued

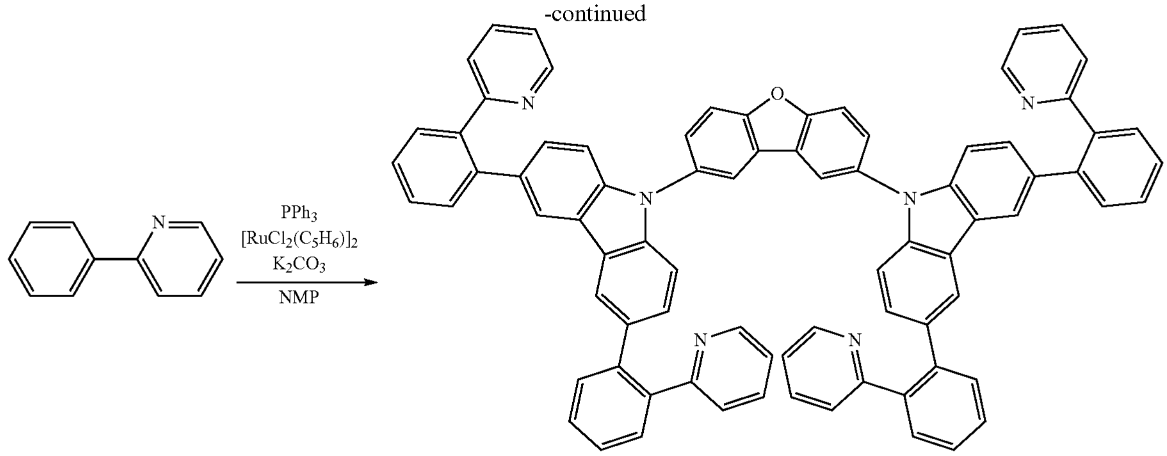

Illustrative compound 5

Step 1: (Synthesis of Intermediate 1)

Under a nitrogen atmosphere, 3,6-dibromodibenzofuran (1.0 mole), carbazole (2.0 moles), copper powder (3.0 moles), potassium carbonate (1.5 moles) were mixed in 300 ml of DMAc (dimethylacetamide) and stirred at 130° C. for 24 hours. After the resulting reaction liquid was cooled to room temperature (25° C.), 1 L of toluene was added to the liquid. The mixture was washed three times with distilled water. The solvent was then removed from the organic layer by distillation under reduced pressure. The residue was purified by silica gel flash chromatography (n-heptane: toluene=4:1 to 3:1) to give intermediate 1 with a yield of 85%.

Step 2: (Synthesis of Intermediate 2)

At room temperature (25° C.), intermediate 1 (0.5 moles) was dissolved in 100 ml of DMF (dimethylformamide) under the atmosphere, and NBS (N-bromosuccinimide) (2.0 moles) was added and stirred at room temperature (25° C.) overnight. The resulting precipitate was separated by filtration and washed with methanol to give intermediate 2 with a yield of 92%.

Step 3: (Synthesis of Illustrative Compound 5)

Under a nitrogen atmosphere, intermediate 2 (0.25 moles), 2-phenylpyridine (1.0 mole), a ruthenium complex $[(\eta^6\text{-}C_6H_6)RuCl_2]_2$ (0.05 moles), triphenylphosphine (0.2 moles), and potassium carbonate (12 moles) were mixed in 3 L of NMP (N-methyl-2-pyrrolidone) and stirred at 140° C. overnight.

After the reaction liquid was cooled to room temperature (25° C.), 5 L of dichloromethane was added, and the reaction liquid was filtered. The solvent was then removed from the filtrate by distillation under reduced pressure (800 Pa, 80° C.). The (N-methyl-2-pyrrolidone) residue was purified by silica gel flash chromatography ($CH_2Cl_2$:$Et_3N$=20:1 to 10:1).

The respective fractions were collected, from which the solvent was removed by distillation under reduced pressure. The residue was then dissolved again in dichloromethane and washed three times with water. The organic phase was dried over anhydrous magnesium sulfate. The solvent was then removed from the dried product by distillation under reduced pressure, so that illustrative compound 5 was obtained with a yield of 68%.

(2) Electrode Layer

The electrode layer 1*b* includes silver or an alloy including silver as a main component. The electrode layer 1*b* is deposited on the underlying layer 1*a*.

The electrode layer 1*b* with such a structure can be deposited by a method using a wet process such as application, ink-jetting, coating, or dipping or by a method using a dry process such as vapor deposition (such as resistive heating or electron beam deposition), sputtering, or CVD. In particular, vapor deposition is preferably used.

The electrode layer 1*b* deposited on the underlying layer 1*a* is characterized by having sufficient electrical conductivity without being subjected to a high-temperature annealing treatment or other treatments after the deposition of the electrode layer 1*b*. If necessary, however, the electrode layer 1*b* may be subjected to a high-temperature annealing treatment or other treatments after the deposition.

The electrode layer 1*b* may include an alloy including silver (Ag) as a main component. In this case, the alloy may be, for example, a silver-magnesium (AgMg), silver-copper (AgCu), silver-palladium (Aged), silver-palladium-copper (AgPdCu), or silver-indium (AgIn) alloy.

The electrode layer 1*b* described above may have a multilayer structure that includes two or more separate layers of silver or a silver-based alloy, stacked as needed.

The electrode layer 1*b* preferably has a thickness in the range of 2 to 15 nm, more preferably in the range of 3 to 12 nm, even more preferably in the range of 4 to 9 nm. When the thickness is 15 nm or less, absorption or reflection by the layer can be kept low, so that the transparent electrode can have high transmittance. When the thickness is 2 nm or more, it can be ensured that the layer has sufficient electrical conductivity.

As described above, the transparent electrode 1 has a multilayer structure including the underlying layer 1*a* and the electrode layer 1*b* deposited on the upper side of the underlying layer 1*a*. The top of the electrode layer 1*b* of the transparent electrode 1 may be covered with a protective film, or an additional electrode layer may be formed on the top of the electrode layer 1*b*. In this case, the protective film and the additional electrode layer should preferably be optically transparent so that the transparent electrode 1 can remain optically transparent.

(3) Advantageous Effects of Transparent Electrode

The transparent electrode 1, configured as described above, includes the underlying layer 1*a* including a nitrogen atom-containing compound; and the electrode layer 1*b* including silver or an alloy including silver as a main component and provided on the underlying layer 1*a*. Therefore, in the process of forming the electrode layer 1*b* on the underlying layer 1*a*, silver atoms used to form the electrode layer 1*b* interact with the nitrogen atom-containing compound in the underlying layer 1*a*, so that the silver atoms are reduced in diffusion length at the surface of the underlying layer 1*a* and thus inhibited from aggregating.

Generally, in the process of depositing an electrode layer 1*b* including silver as a main component, silver particles can easily form isolated islands due to nucleation growth (Volumer Weber (VW) mode), which makes it difficult to obtain electrical conductivity when the layer is thin, and also increases the sheet resistance. This suggests that a thick layer should be formed to ensure the electrical conductivity. However, a thick layer can reduce the light transmittance and thus is not proper for the transparent electrode.

According to the structure of the transparent electrode 1, however, the aggregation of silver is suppressed on the underlying layer 1*a* as described above, so that the electrode layer 1*b* including silver or an alloy including silver as a main component can be formed in a monolayer growth mode (Frank van der Merwe (FM) mode).

Regarding the transparent electrode 1, the term "transparent" means that it has a light transmittance of 50% or more at a wavelength of 550 nm. Each of the above materials for the underlying layer 1*a* can form a film with sufficiently high optical transparency as compared with silver or an alloy including silver as a main component for the electrode layer 1*b*. On the other hand, the conductivity of the transparent electrode 1 is mainly ensured by the electrode layer 1*b*. As described above, the electrode layer 1*b* including silver or an alloy including silver as a main component can ensure conductivity with a smaller thickness. Therefore, the transparent electrode 1 can have both higher conductivity and higher optical transparency.

(4) Applications of Transparent Electrode

The transparent electrode 1 configured as described above can be used not only in the organic light-emitting device of the present invention but also in a variety of other electronic devices. Examples of other electronic devices include LEDs (light-emitting diodes), liquid crystal devices, solar cells, touch panels, and the like. In these electronic devices, the transparent electrode 1 can be used as an electrode member required to have optical transparency.

<Internal Light Extraction Layer>

The internal light extraction layer 2 is disposed between the transparent substrate 13 and the transparent electrode 1. The internal light extraction layer 2 includes a scattering layer 2*a* and a smooth layer 2*b*, which are stacked in order from the transparent substrate 13 side.

The internal light extraction layer 2 has a refractive index in the range of 1.7 to less than 2.5 at a wavelength of 550 nm. Waveguide mode light is confined in the light-emitting layer of the organic light-emitting device, and plasmon mode light is reflected from the cathode. Since these modes are specific optical modes, a refractive index of 1.7 or more is necessary for the extraction of light in these modes. On the other hand, there is almost no light in the region of a refractive index of 2.5 or more even with respect to the highest-order plasmon mode. Therefore, the quantity of extractable light will not increase even if the refractive index is 2.5 or more.

In fact, it is preferred that the scattering layer 2*a* and the smooth layer 2*b* each have a refractive index of 1.7 to less than 2.5. In many cases, however, it is difficult to independently measure the refractive index of each layer. Thus, the internal light extraction layer 2 as a whole only has to have a refractive index in the above range.

In the present invention, the refractive index can be measured with a multi-wavelength Abbe refractometer, a prism coupler, a Michelson interferometer, a spectroscopic ellipsometer, or the like.

In addition, the internal light extraction layer 2 should have a haze value (the ratio of the scattering transmittance to the total light transmittance) of 20% or more, more preferably 25% or more, even more preferably 30% or more. When the haze value is 20% or more, the luminous efficiency can be improved.

The haze value is a physical property calculated based on (i) the effect of the difference in the refractive index of the composition in the film and (ii) the effect of the surface profile. In the present invention, the internal light extraction layer 2 having the smooth layer 2*b* disposed on the scattering layer 2*a* is subjected to the measurement of the haze value. Therefore, when the average surface roughness Ra per 10 μm square is reduced to less than 100 nm, the haze value can be measured without the effect (ii).

In the present invention, the internal light extraction layer 2 preferably has a transmittance of 50% or more, more preferably 55% or more, even more preferably 60% or more.

(1) Scattering Layer

The scattering layer 2*a* is preferably a high refractive index layer with a refractive index in the range of 1.7 to less than 2.5. In this case, the scattering layer 2*a* may be a film made of a single material with a refractive index of 1.7 to less than 2.5 or a film formed by mixing two or more compounds so that the mixture can have a refractive index of 1.7 to less than 2.5. In the case of such a mixed system, a calculated refractive index obtained by summing the values each obtained by multiplying the intrinsic refractive index of each material by each mixing ratio may be used instead as the refractive index of the scattering layer 2*a*. In this case, the refractive index of each material may be less than 1.7 or not less than 2.5 as long as the film of the mixture has a refractive index of 1.7 to less than 2.5.

In the present invention, the scattering layer 2*a* may be a scattering mixture layer (scattering film) that takes advantage of a refractive index difference caused by a mixture of a resin and particles. Alternatively, the scattering layer 2*a* may be a shape-controlled scattering layer that is formed by controlling a shape such as forming a dip-and-bump structure.

(1.1) Scattering Mixture Layer

Next, a case where a layer configured to diffract or diffuse light (scattering mixture layer) is used in the present invention will be described.

The scattering mixture layer is provided to increase the light extraction efficiency and formed on the uppermost surface of the transparent substrate 13 on the transparent electrode 1 side.

The scattering mixture layer 2*a* includes a layer medium and particles contained in the layer medium.

There is a difference between the refractive index of a resin material (binder) as the layer medium and the refractive index of the particles in the layer medium. The refractive index difference may be 0.03 or more, preferably 0.1 or more, more preferably 0.2 or more, even more preferably 0.3 or more. When the refractive index difference between the layer medium and the particles is 0.03 or more, a scattering effect occurs at the interface between the layer medium and the particles. Preferably, as the refractive index difference increases, greater refraction occurs at the interface, so that the scattering effect increases.

As mentioned above, the scattering mixture layer 2*a* diffuses light by using the refractive index difference between the layer medium and the particles. Therefore, the particles therein are preferably transparent particles having a particle size equal to or greater than the size in the Mie scattering region in the visible light range. The particles preferably have an average particle size of 0.2 μm or more.

On the other hand, the upper limit of the average particle size is preferably less than 10 μm, more preferably less than 5 μm, even more preferably less than 3 μm, most preferably less than 1 μm, because as the particle size becomes larger, the thickness of the smooth layer 2*b* for smoothing the roughness of the scattering mixture layer 2*a* containing the particles needs to be increased, which is disadvantageous for process load and film absorption.

The average particle size of the high refractive index particles can be measured using a system based on dynamic light scattering, such as Nanotrac UPA-EX150 manufactured by NIKKISO CO., LTD., or using electron micrograph image processing.

Such particles are not restricted and may be appropriately selected depending on the purpose. The particles may be organic or inorganic fine particles. In particular, the particles are preferably inorganic fine particles with a high refractive index.

The organic fine particles with a high refractive index may be, for example, polymethyl methacrylate beads, acrylic-styrene copolymer beads, melamine beads, polycarbonate beads, styrene beads, crosslinked polystyrene beads, polyvinyl chloride beads, benzoguanamine-melamine formaldehyde beads, or the like.

The inorganic fine particles with a high refractive index may be, for example, inorganic oxide particles made of an oxide of at least one selected from zirconium, titanium, aluminum, indium, zinc, tin, antimony, and the like. Specifically, the inorganic oxide particles may be made of $ZrO_2$, $TiO_2$, $BaTiO_3$, $Al_2O_3$, $In_2O_3$, ZnO, $SnO_2$, $Sb_2O_3$, ITO, $SiO_2$, $ZrSiO_4$, zeolite, or the like. In particular, $TiO_2$, $BaTiO_3$, $ZrO_2$, ZnO, and $SnO_2$ are preferred, and $TiO_2$ is most preferred. Rutile type $TiO_2$ is more preferable than anatase type $TiO_2$ because the former has a higher refractive index and lower catalytic activity so that it can allow the high refractive index layer and the adjacent layer to have higher weather resistance.

As mentioned below, a liquid dispersion of the particles for forming the scattering mixture layer 2*a* with a high refractive index may be prepared. In this case, the particles may be subjected to a surface treatment before use, or the particles may be used without being subjected to a surface treatment. Which should be selected may be determined in view of the improvement of the dispersibility or stability.

When a surface treatment is performed, examples of the material for use in the surface treatment include a different type of inorganic oxide, such as silicon oxide or zirconium oxide, a metal hydroxide such as aluminum hydroxide, organosiloxane, and an organic acid such as stearic acid. These surface treatment materials may be used alone or in combination of two or more. Particularly in view of the stability of the liquid dispersion, the surface treatment material is preferably a different type of inorganic oxide and/or a metal hydroxide, more preferably a metal hydroxide.

When the inorganic oxide particles are coated with the surface treatment material, the content of the coating is preferably 0.01 to 99% by weight (in general, the content of the coating is expressed by the ratio of the weight of the surface treatment material used on the surface of the particles to the weight of the particles). If the content of the surface treatment material coating is too low, the dispersibility- or stability-improving effect of the surface treatment can be insufficient. If the content is too high, the refractive index of the high refractive index scattering mixture layer 2*a* will decrease, which is not preferred.

In addition, quantum dots described in WO 2009/014707 A and U.S. Pat. No. 6,608,439 are also preferably used as high refractive index materials.

The high refractive index particles have a refractive index of 1.7 or more, preferably 1.85 or more, more preferably 2.0 or more. If the refractive index is less than 1.7, the refractive index difference between the binder and the particles would be so small that the scattering quantity would decrease, which may make it impossible to obtain the effect of improving the light extraction efficiency.

On the other hand, the refractive index of the high refractive index particles should have an upper limit of less than 3.0. When the refractive index difference between the binder and the particles is large, a sufficient quantity of scattering can be achieved, and the effect of improving the light extraction efficiency can be obtained.

The high refractive index particles are preferably disposed with a particle monolayer thickness in such a way that the particles are in contact with or close to the interface between the scattering mixture layer 2*a* and the smooth layer 2*b*. This makes it possible for the particles to scatter evanescent light, which leaks to the scattering mixture layer 2*a* when total reflection occurs in the smooth layer 2*b*, so that the light extraction efficiency will increase. If the high refractive index particles exist in a region with a thickness larger than the average particle size (for example, if the thickness of the scattering mixture layer 2*a* is 1.3 times the average particle size of the high refractive index particles), some particles relatively far from the interface will not scatter evanescent light and not contribute to the improvement of the light extraction efficiency. If the thickness of the particle distribution increases, a problem may arise, such as a reduction in coating uniformity or interface smoothness or display performance degradation due to an increase in reflected scattered light.

The content of the high refractive index particles in the scattering mixture layer 2*a* is preferably in the range of 1.0 to 70%, more preferably in the range of 5 to 50%, in terms of volume fraction. This makes it possible to form a distribution of high and low refractive indices at the interface between the scattering mixture layer 2*a* and the smooth layer 2*b*, so that the quantity of light scattering can be increased to increase the light extraction efficiency.

When the layer medium is a resin material, a method for forming the scattering mixture layer 2*a* includes, for example, dispersing the particles in a resin material (polymer) solution for forming the medium (the particles are insoluble in the solvent used) and then applying the dispersion to a substrate.

Some of the particles can locally cause a diffraction effect because they are actually polydispersed particles and difficult to arrange regularly, but many of the particles can improve the light extraction efficiency by changing the direction of light based on diffusion.

In the present invention, any of known resins (binders) may be used as the binder with no particular limitation. Examples of the binder include acrylic esters, methacrylic esters, polyethylene terephthalate (PET), polybutylene terephthalate, polyethylene naphthalate (PEN), polycarbonate (PC), polyarylate, polyvinyl chloride (PVC), polyethylene (PE), polypropylene (PP), polystyrene (PS), nylon (Ny), aromatic polyamide, polyether ether ketone, polysulfone, polyether sulfone, polyimide, polyether imide, and other resin films, heat-resistant transparent films (e.g., Sila-DEC (product name) manufactured by Chisso Corporation) having an organic-inorganic hybrid structure with a basic skeleton of silsesquioxane, polysiloxane, polysilazane, polysiloxazane, or the like, perfluoroalkyl group-containing silane compounds (e.g., (heptadecafluoro-1,1,2,2-tetradecyl)triethoxysilane), fluorine-containing copolymers having constituent units derived from a fluorine-containing monomer and a monomer for adding a crosslinking group, and the like. Two or more of these resins may be used in a mixture. Among them, organic-inorganic hybrid structure-containing resins are preferred.

Hydrophilic resins shown below may also be used. Hydrophilic resins may be water-soluble reins, water-dispersible resins, colloidally dispersible resins, or any mixture thereof. Hydrophilic resins include acrylic resins, polyester resins, polyamide resins, polyurethane resins, fluororesins, and the like. Specific examples include polyvinyl alcohol, gelatin, polyethylene oxide, polyvinylpyrrolidone, casein, starch, agar, carrageenan, polyacrylic acid, polymethacrylic acid, polyacrylamide, polymethacrylamide, polystyrene sulfonic acid, cellulose, hydroxyethyl cellulose, carboxymethyl cellulose, hydroxyethyl cellulose, dextran, dextrin, pullulan, water-soluble polyvinyl butyral, and other polymers. In particular, polyvinyl alcohol is preferred.

One of these polymers may be used alone as the binder resin, or if necessary, two or more of these polymers may be mixed and used as the binder resin.

Conventionally known resin particles (emulsion) or the like may also preferably be used.

The binder to be used is also preferably a resin curable generally with ultraviolet rays or electron beams, specifically, a mixture of an ionizing radiation-curable resin, a thermoplastic resin, and a solvent, or a thermosetting resin.

Such a binder resin is preferably a polymer having a saturated hydrocarbon or polyether main chain, more preferably a polymer having a saturated hydrocarbon main chain.

In addition, the binder is preferably crosslinked. The polymer having a saturated hydrocarbon main chain is preferably obtained by polymerization reaction of an ethylenic unsaturated monomer or monomers. A monomer having two or more ethylenic unsaturated groups is preferably used to form a crosslinked binder.

In the present invention, it is particularly preferred to use a compound capable of forming a metal oxide, a metal nitride, or a metal oxynitride upon exposure to ultraviolet rays under a specific atmosphere. Such a compound suitable for use in the present invention is preferably the compound described in JP 08-112879 A, which can undergo a modification treatment at relatively low temperature.

Specific examples of such a compound include a polysiloxane having Si—O—Si bonding (including a polysilsesquioxane), a polysilazane having Si—N—Si bonding, and a polysiloxazane having both Si—O—Si bonding and Si—N—Si bonding. Two or more of them may be mixed and used. Different compounds may also be sequentially or simultaneously stacked and used.

(Polysiloxane)

A polysiloxane for use in the present invention may include any of the following general structural units: $[R_3SiO_{1/2}]$, $[R_2SiO]$, $[RSiO_{3/2}]$, and $[SiO_2]$, wherein R is independently selected from the group consisting of a hydrogen atom, an alkyl group having 1 to 20 carbon atoms (such as methyl, ethyl, or propyl), an aryl group (such as phenyl), and an unsaturated alkyl group (such as vinyl). Specific examples of the polysiloxane group include $[PhSiO_{3/2}]$, $[MeSiO_{3/2}]$, $[HSiO_{3/2}]$, [MePhSiO], $[Ph_2SiO]$, [PhviSiO], $[ViSiO_{3/2}]$ (Vi represents a vinyl group), [MeHSiO], [MeViSiO], $[Me_2SiO]$, $[Me_3SiO_{1/2}]$, and the like. A polysiloxane mixture or copolymer may also be used.

(Polysilsesquioxane)

In the present invention, the polysiloxane is preferably a polysilsesquioxane. A polysilsesquioxane is a compound including silsesquioxane as a structural unit. A "silsesquioxane" is a compound represented by $[RSiO_{3/2}]$, which is a polysiloxane synthesized generally by hydrolysis and polycondensation of an $RSiX_3$ type compound (R is a hydrogen atom, alkyl, alkenyl, aryl, aralkyl, or the like, and X is halogen, alkoxy, or the like). Typical known examples of the molecular configuration of polysilsesquioxane include a random structure, a ladder structure, a cage structure, and a partially opened cage structure (a cage-like structure lacking one silicon atom or a cage-like structure in which silicon-oxygen linkages are partially cleaved).

Among these polysilsesquioxanes, what is called a hydrogen silsesquioxane polymer is preferably used. The hydrogen silsesquioxane polymer may be a hydride siloxane polymer represented by $HSi(OH)_x(OR)_yO_{z/2}$, wherein each R is an organic group or a substituted organic group, which forms a hydrolyzable substituent when bonded to silicon through an oxygen atom, x=0 to 2, y=0 to 2, z=1 to 3, and x+y+z=3. R may be alkyl (such as methyl, ethyl, propyl, or butyl), aryl (such as phenyl), or alkenyl (such as allyl or vinyl). These resins may be completely condensed $(HSiO_{3/2})n$ or only partially hydrolyzed (in other words, the product may include some of the Si—OR moieties), and/or partially condensed (in other words, the product may include some of the Si—OH moieties).

(Polysilazane)

A polysilazane for use in the present invention is a polymer having silicon-nitrogen bonding, which is an inorganic precursor polymer of $SiO_2$, $Si_3N_4$, and $SiO_xN_y$ (x: 0.1 to 1.9, y: 0.1 to 1.3) (an intermediate solid solution of $SiO_2$ and $Si_3N_4$) or the like, having Si—N, Si—H, N—H, and the like.

A polysilazane represented by formula (B) below is preferably used in the present invention.

$$[\text{—}Si(R_1)(R_2)\text{—}N(R_3)]\text{—} \qquad \text{Formula (B):}$$

In formula (B), $R_1$, $R_2$, and $R_3$ each represent a hydrogen atom, an alkyl group, an alkenyl group, a cycloalkyl group, an aryl group, an alkylsilyl group, an alkylamino group, or an alkoxy group.

In the present invention, a perhydropolysilazane in which $R_1$, $R_2$, and $R_3$ are all hydrogen atoms is particularly preferred in view of denseness.

When the binder is an ionizing radiation-curable resin composition, a common curing method, specifically, electron beam irradiation or ultraviolet light irradiation may be used to cure the ionizing radiation-curable resin composition.

For example, the electron beam curing may be performed using electron beams with an energy of 10 to 1,000 keV, preferably 30 to 300 keV emitted from any of various electron beam accelerators such as Cockcroft-Walton, Van de Graaff, resonant transformer, insulated core transformer, linear, Dynamitron, and radio frequency accelerators. For example, the ultraviolet curing may be performed using ultraviolet rays generated from a light source such as an ultrahigh pressure mercury lamp, a high pressure mercury lamp, a low pressure mercury lamp, a carbon arc lamp, a xenon arc lamp, or a metal halide lamp.

(Vacuum Ultraviolet Irradiation Device with Excimer Lamp)

In the present invention, a preferred ultraviolet irradiation device specifically includes a rare gas excimer lamp configured to emit vacuum ultraviolet rays at 100 to 230 nm.

Rare gas atoms such as Xe, Kr, Ar, and Ne do not form molecules through chemical bonding, and thus such rare gas is called inert gas. However, when charged with energy by discharge or the like, rare gas atoms (excited atoms) can bond to other atoms to form molecules.

For example, a rare gas of Xe (xenon) emits 172 nm excimer light when as shown in the reaction formulae below, excited excimer molecules $Xe_2$* are transferred to the ground state.

$$e+Xe \rightarrow Xe^*$$

$$Xe^*+2Xe \rightarrow Xe_2^*+Xe$$

$$Xe_2^* \rightarrow Xe+Xe+h\nu(172\ nm)$$

An excimer lamp is characterized in that the radiation concentrates on a single wavelength with almost no radiation other than necessary light so that it has high efficiency. In addition, it does not emit excessive radiation so that it can keep the temperature of the object relatively low. It also does not take time to start or restart and can be instantly turned on and off.

A dielectric barrier discharge lamp is a light source capable of efficiently applying excimer light.

A dielectric barrier discharge lamp is configured to generate discharge between electrodes with a dielectric interposed therebetween, in which generally at least one of the electrodes should be disposed at a discharge vessel of a dielectric material and the outside thereof. The dielectric barrier discharge lamp includes, for example, a double cylindrical discharge vessel including thick and thin quartz glass tubes; rare gas such as xenon sealed therein; a first mesh electrode provided outside the discharge vessel; and another electrode provided inside the inner tube. When a high-frequency voltage or the like is applied between the electrodes, the dielectric barrier discharge lamp generates dielectric barrier discharge in the discharge vessel, so that excimer light is emitted when excimer molecules of xenon or the like, generated by the discharge, undergo dissociation.

The excimer lamp has high light generation efficiency and thus can be turned on with low power. It is also characterized by being capable of preventing an increase in the temperature of the object irradiated with the light because it does not emit long-wavelength light responsible for temperature increase and radiates energy at a single wavelength in the ultraviolet region.

(1.2) Shape-Controlled Scattering Layer

In the present invention, the shape-controlled scattering layer 2*a* is preferably provided at a total reflection interface or preferably provided at the interface between layers with different refractive indices where the intensity of total reflection is high. The term "total reflection interface" refers to an interface with a refractive index difference of 0.05 or more. An interface with a refractive index difference of 0.1 or more is more effective, and an interface with a refractive index difference of 0.15 or more is much more effective.

When there are two or more interfaces with such properties, it is preferable to provide two or more scattering layers at the two or more interfaces. It is also preferable to dispose the scattering layer at a position closest to the substrate.

The shape-controlled scattering layer 2*a* has a dip-and-bump structure capable of diffracting or diffusing light. The shape-controlled scattering layer 2*a* is provided on the transparent substrate 13. When the shape-controlled scattering layer 2*a* is provided on the uppermost surface of the transparent substrate 13, for example, the transparent electrode (anode) 1, each layer of the light-emitting functional layer 3 including the light-emitting layer 3*c*, the counter electrode 5*a*, and other components can be disposed on the shape-controlled scattering layer 2*a* to form the organic light-emitting device 100. In this case, part of the light emitted from the light-emitting layer 3*c* can be extracted to improve the luminous efficiency. In an organic light-emitting device without the internal light extraction layer 2, however, it is generally impossible to extract such part of the light because the light undergoes total reflection at the interface between the substrate and the electrode (anode).

The dip-and-bump structure capable of diffracting light includes dips and bumps arranged with a certain pitch (period).

In order to improve the visible light extraction efficiency, the dip-and-bump structure should form a diffraction grating for diffracting light with a wavelength of 400 to 750 nm in a visible light medium. There is a certain relationship between the angles of light incident on and outgoing from the diffraction grating, the diffraction grating spacing (the period of the arrangement of dips and bumps), the wavelength of light, the refractive index of the medium, the diffraction order, and other factors. In the present invention, to diffract light in the visible light region and a wavelength region close thereto, dips and bumps should be arranged with a certain pitch P (see FIG. 2) in the range of 150 to 3,000 nm depending on the wavelength at which the extraction efficiency is to be improved.

The dip-and-bump structure capable of functioning as a diffraction grating is described in, for example, JP 11-283751 A and JP 2003-115377 A. A striped diffraction grating has no diffracting effect in a direction parallel to the stripe. Therefore, the diffraction grating should preferably function evenly in all two-dimensional directions. For example, the diffraction grating preferably includes dips and bumps that each have a certain shape and are regularly arranged at certain intervals when viewed in the normal direction of the substrate surface or the display surface.

The shape of the hole in the dip is typically, but not limited to, circular, triangular, quadrangular, or polygonal. The hole preferably has an inner diameter in the range of 75 to 1,500 nm (as calculated for a circle with the same area).

When viewed in the plan direction, the cross-sectional shape of the dip (pit) may be, but not limited to, hemispherical, rectangular, semicircular, or pyramidal. The dip preferably has a depth in the range of 50 to 1,600 nm, more preferably in the range of 50 to 1,200 nm. The dip with a depth smaller than this would be less effective in causing diffraction or scattering. The dip with too large a depth can degrade the flatness of the display device, which is not preferred.

To form a diffraction grating, these dips are preferably arranged in a two-dimensionally, regularly repeated pattern such as a square lattice pattern (tetragonal lattice pattern) or a honeycomb lattice pattern.

The shape of the projection (bump) may be the same as that of the dip. For example, when the bump is a columnar projection, the shape of the projection may be circular, triangular, quadrangular, or polygonal when viewed in the normal direction of the surface. The height and pitch (period) of the projections may be set in the same way as in the case where the holes are formed. In other words, the shapes of the dip and the bump may be reverse to each other, and the bump may be formed to have the size for the dip.

FIGS. 2 to 4C show examples of the dip-and-bump structure formed as described above and capable of functioning as a diffraction grating.

Figure 2:
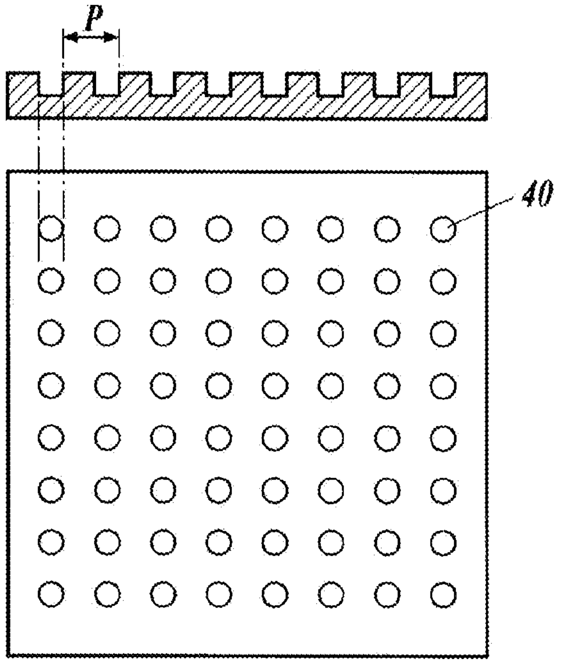
FIG. 2 is a schematic view showing an example of the dip-and-bump structure of a scattering layer.
Figure 3:
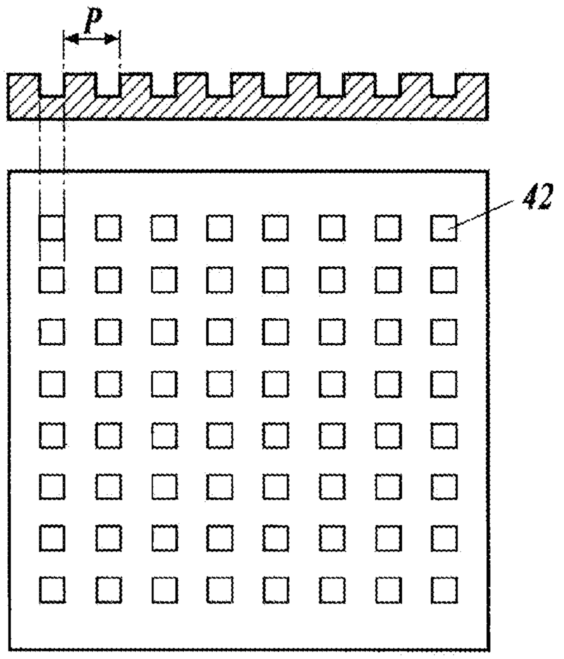
FIG. 3 is a schematic view showing an example of the dip-and-bump structure of a scattering layer.

FIG. 2 shows a dip-and-bump structure in which dips 40 each having a circular hole and a rectangular cross-section are arranged in a square lattice pattern. FIG. 3 shows a dip-and-bump structure in which dips 42 each having a square hole and a rectangular cross-section are arranged in a square lattice pattern.

Figure 4A:
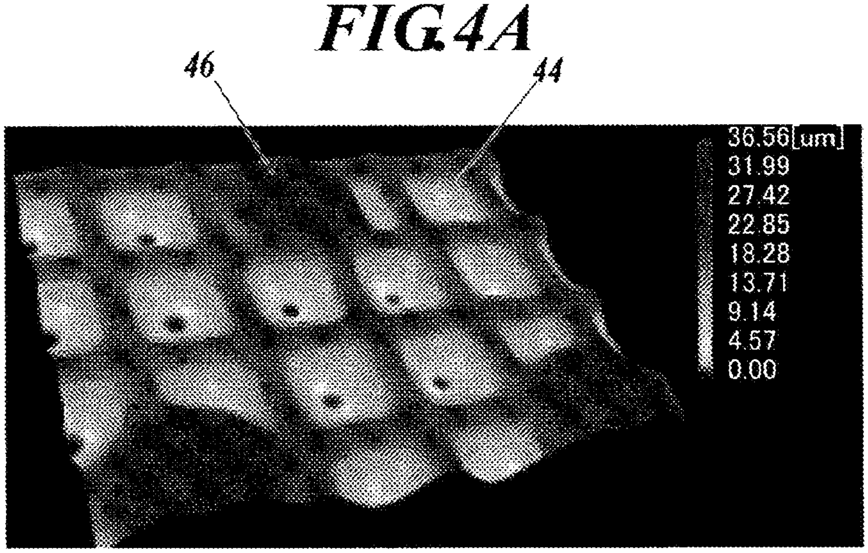
FIG. 4A is a view showing an example of the dip-and-bump structure of a scattering layer.
Figure 4B:
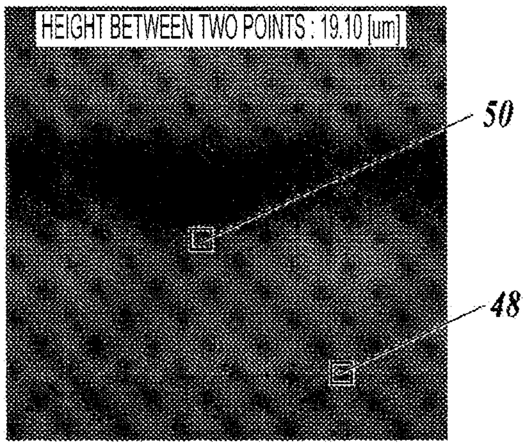
FIG. 4B is a view showing an example of the dip-and-bump structure of a scattering layer.
Figure 4C:
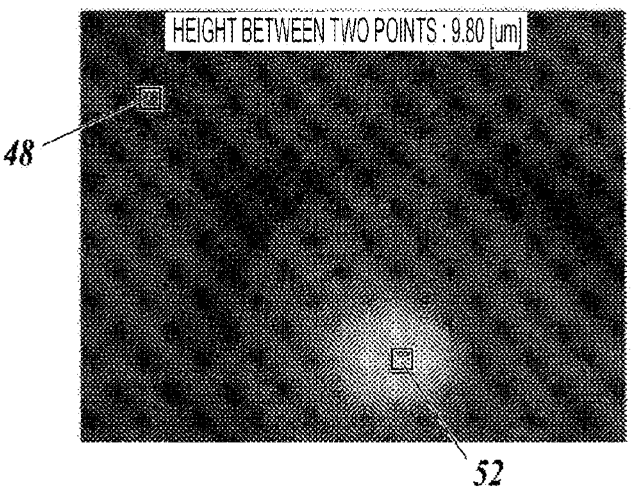
FIG. 4C is a view showing an example of the dip-and-bump structure of a scattering layer.

FIG. 4A shows a complex dip-and-bump structure in which pyramidal (waffle-like) dips 44 and hemispherical bumps 46 are formed and arranged in a square lattice pattern. FIGS. 4B and 4C show examples in which the dips 44 has a depth (a difference between the levels of a lattice point 48 and the apex 50 of the dip 44) of about 20 μm and the bumps 46 have a height (a difference between the levels of the lattice point 48 and the apex 52 of the bump 46) of about 10 μm although the depth and the height are non-limiting.

The shape-controlled scattering layer 2*a* having such a dip-and-bump structure may be formed on, for example, the surface of the substrate, so that emitted light with a wavelength corresponding to the pitch (period) of the dip-and-bump structure can be extracted with improved efficiency from the substrate side.

These diffraction gratings can be formed, for example, on a resin material film by an imprinting technique or the like. When an imprinting technique is used, for example, the desired dip-and-bump structure can be formed by a process that includes forming a polymer film of thermoplastic resin such as polymethyl methacrylate (PMMA) on the substrate and then heating and pressing the thermoplastic resin against a mold having dips and bumps to transfer the dip-and-bump shape of the mold to the resin.

Another forming technique may also be used, which includes applying an ultraviolet-curable resin to the substrate and then applying ultraviolet rays to the resin while bringing the resin into intimate contact with a mold having dips and bumps so that the dip-and-bump shape of the mold is transferred to the resin being cured by photopolymerization.

The dip-and-bump structure may also be formed by etching a gas barrier layer of an inorganic oxide such as silicon oxide. In this case, reactive ion etching or the like may be used.

Alternatively, the dip-and-bump structure can be formed on a gas barrier layer of an inorganic oxide such as silicon oxide by a process that includes forming a gel film by sol-gel method and then heating the gel film while pressing a mold with dips and bumps against the gel film.

On the other hand, the dip-and-bump structure capable of diffusing light is a structure configured to diffuse light by diffraction, refraction, and reflection, which may have, for example, a corrugated shape with an average pitch (period) in the range of 0.3 to 20 μm and an average height in the range of 100 to 7,000 nm corresponding to about ⅕ to ⅓ of the pitch. The height should preferably be at least 100 nm so that light propagating in the light-emitting layer by total reflection or reflection from the metal electrode as a cathode can be diffused and extracted in a sufficient amount relative to the amount of light outgoing directly to the outside. If the pitch (period) of the corrugated shape is too long, the light-emitting layer can absorb light before the occurrence of the scattering phenomenon, and if the average height is too large, the light-emitting layer can be difficult to form, which are not preferred.

Figure 5A:
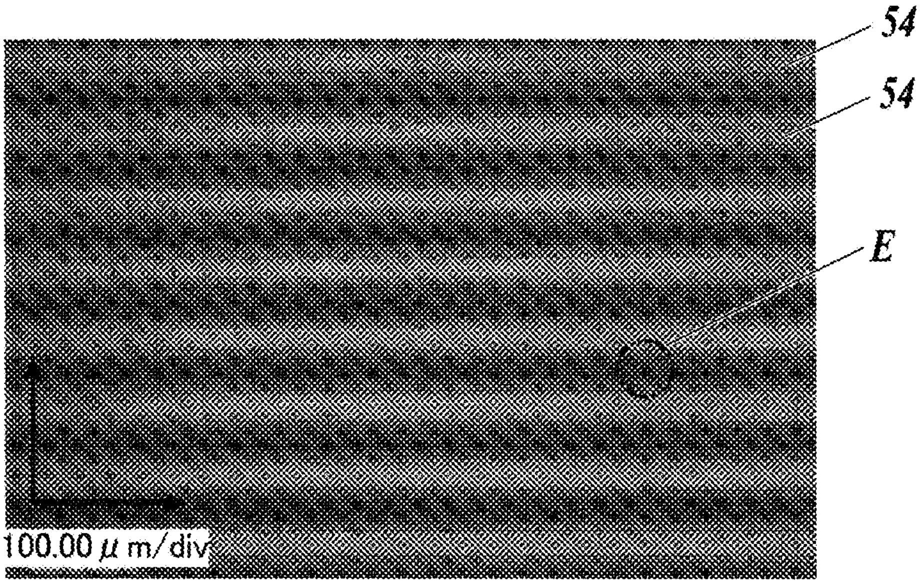
FIG. 5A is a view showing an example of the dip-and-bump structure of a scattering layer.
Figure 5B:
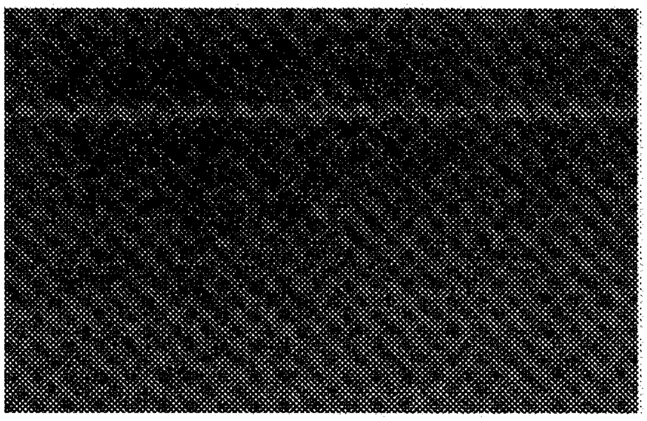
FIG. 5B is a view showing an example of the dip-and-bump structure of a scattering layer.

FIG. 5A shows a corrugated shape that includes about 50-μm-wide semicylindrical cross-section parts 54 continuously formed in parallel on a substrate. FIG. 5B is an enlarged view of part E in FIG. 5A, showing that the surface of the semicylindrical part has dips and bumps formed by a large number of small particles.

Figure 6A:
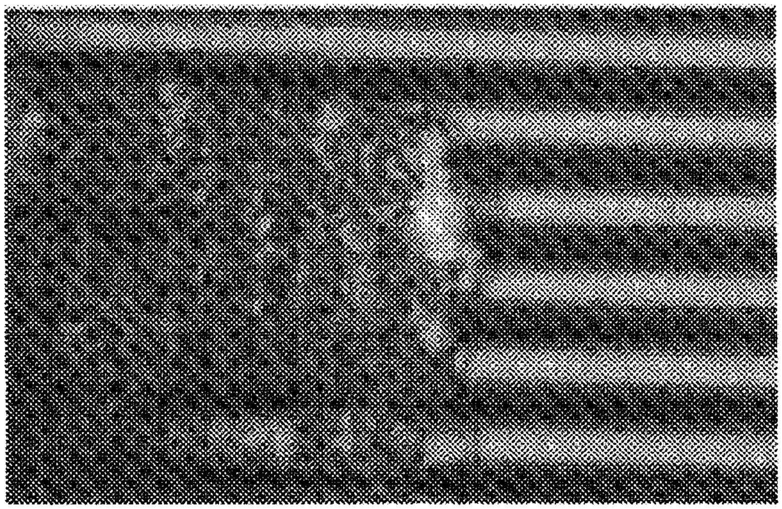
FIG. 6A is a view showing the state of the inside of the dip-and-bump structure shown in FIG. 5.
Figure 6B:
FIG. 6B is a view showing the state of the inside of the dip-and-bump structure shown in FIG. 5.

As shown in FIGS. 6A and 6B, when the surface of the semicylindrical part was shaved, a large number of particles with a particle size of about 2 to 3 μm were observed in the inside while the binder was not identifiable.

(2) Smooth Layer

In the present invention, the smooth layer 2*b* is preferably a high refractive index layer with a refractive index of 1.7 to less than 2.5. As long as it has a refractive index of 1.7 to less than 2.5, it may be made of a single material or a mixture. When a mixture is used to form the smooth layer 2*b*, the concept for its refractive index is the same as that for the scattering layer 2*a*.

Figure 7:
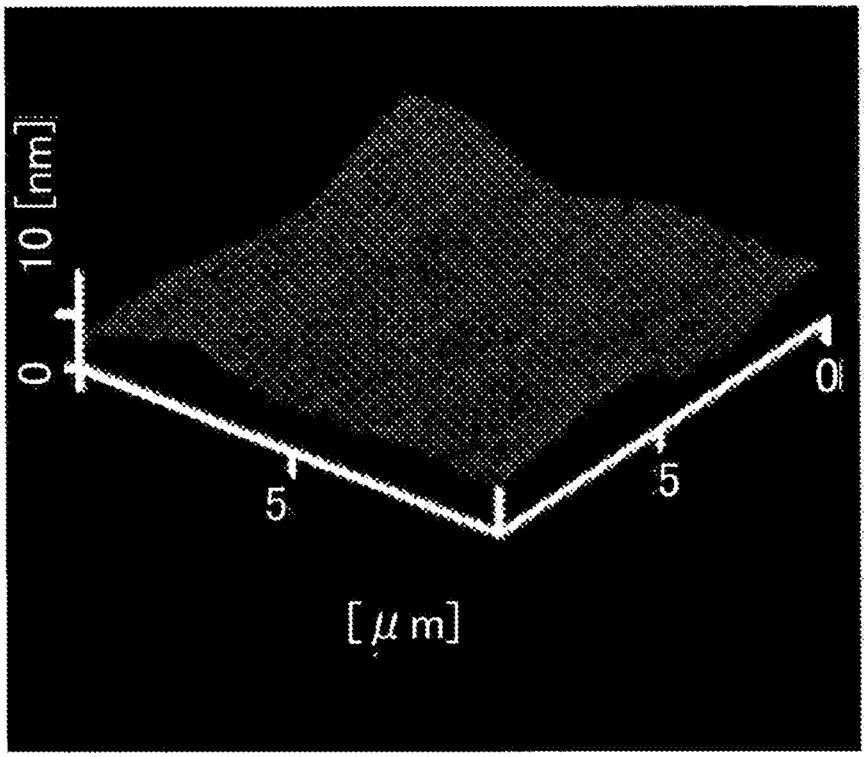
FIG. 7 is a view showing an example of the results of the AFM measurement of the average surface roughness of a smooth layer.

It is important that the smooth layer 2*b* has such flatness that the transparent electrode 1 can be formed in good condition thereon. Regarding the surface profile, the smooth layer 2*b* should have an average surface roughness Ra of less than 100 nm, preferably less than 30 nm, more preferably less than 10 nm, most preferably less than 5 nm. FIG. 7 shows an example of the results of the measurement of the average surface roughness Ra of the smooth layer 2*b* according to the present invention.

As used herein, the term "average surface roughness Ra" refers to the average surface roughness Ra per 10 μm square measured by atomic force microscopy (AFM).

The resin (binder) used to form the smooth layer 2*b* may be the same resin as for the scattering layer 2*a*.

The high refractive index material in the smooth layer 2*b* is preferably a fine particle sol.

The high refractive index smooth layer 2*b* may contain metal oxide fine particles. The lower limit of the refractive index of the metal oxide fine particles (in a bulk state) is preferably 1.7 or more, more preferably 1.85 or more, even more preferably 2.0 or more, furthermore preferably 2.5 or more. The upper limit of the refractive index of the metal oxide fine particles is preferably 3.0 or less. If the metal oxide fine particles have a refractive index of less than 1.7, the desired effect of the present invention can be undesirably small. If the metal oxide fine particles have a refractive index of more than 3.0, multiple scattering in the film can increase so that the transparency can undesirably decrease.

In general, the lower limit of the particle size of the metal oxide fine particles (inorganic particles) in the high refractive index smooth layer 2*b* is preferably 5 nm or more, more preferably 10 nm or more, even more preferably 15 nm or more. The upper limit of the particle size of the metal oxide fine particles is preferably 70 nm or less, more preferably 60 nm or less, even more preferably 50 nm or less. The metal oxide fine particles with a particle size of less than 5 nm can easily aggregate to rather reduce the transparency, which is not preferred. The smaller particle size provides a larger surface area which may increase the catalytic activity and facilitate the degradation of the smooth layer 2*b* and the adjacent layer, which is not preferred. The metal oxide fine particles with a particle size of more than 70 nm can reduce the transparency of the smooth layer 2*b*, which is not preferred. As long as the effects of the present invention are not impaired, the particles may have any size distribution and may have a broad or narrow size distribution or two or more size distributions.

The lower limit of the content of the metal oxide fine particles in the smooth layer 2*b* is preferably 70% by weight or more, more preferably 80% by weight or more, even more preferably 85% by weight or more, based on the total weight of the smooth layer 2*b*. The upper limit of the content of the metal oxide fine particles is preferably 97% by weight or less, more preferably 95% by weight or less. If the content of the metal oxide fine particles in the smooth layer 2*b* is less than 70% by weight, it would be substantially difficult to set the refractive index of the smooth layer 2*b* to 1.80 or more. If the content of the metal oxide fine particles in the smooth layer 2*b* is more than 95% by weight, it would be difficult to form the smooth layer 2*b* by coating, and even if possible, the resulting film can have high brittleness and low flex resistance after drying, which is not preferred.

The metal fine particles in the smooth layer 2*b* according to the present invention are more preferably $TiO_2$ (titanium dioxide sol) in view of stability. In particular, rutile type $TiO_2$ is more preferable than anatase type $TiO_2$ because the former has a higher refractive index and lower catalytic activity so that it can allow the smooth layer 2*b* and the adjacent layer to have higher weather resistance.

Methods for preparing titanium dioxide sol, which may be used in the present invention, can be found in, for example, JP 63-17221 A, JP 07-819 A, JP 09-165218 A, and JP 11-43327 A.

The titanium dioxide fine particles preferably have a primary particle size in the range of 5 to 15 nm, more preferably in the range of 6 to 10 nm.

<Transparent Substrate>

The substrate 13 on which the transparent electrode 1 (the internal light extraction layer 2) is formed may be, for example, but not limited to, glass, plastic, or the like. Glass, quartz, or a transparent resin film is preferably used to form the transparent substrate 13.

The glass may be, for example, silica glass, soda lime silica glass, lead glass, borosilicate glass, alkali-free glass, or the like. In view of adhesion to the scattering layer 2*a*, durability, and smoothness, if necessary, the surface of these glass materials may be subjected to a physical process such as polishing, or a coating of an inorganic or organic material or a hybrid coating of a combination thereof may be formed on the surface of these glass materials.

The resin film may be made of, for example, polyester such as polyethylene terephthalate (PET) or polyethylene naphthalate (PEN), polyethylene, polypropylene, cellophane, cellulose esters such as cellulose diacetate, cellulose triacetate (TAC), cellulose acetate butyrate, cellulose acetate propionate (CAP), cellulose acetate phthalate, and cellulose nitrate, or derivatives thereof, polyvinylidene chloride, polyvinyl alcohol, polyethylene vinyl alcohol, syndiotactic polystyrene, polycarbonate, norbornene resin, polymethylpentene, polyether ketone, polyimide, polyether sulfone (PES), polyphenylene sulfide, polysulfones, polyether imide, polyether ketone imide, polyamide, fluororesin, nylon, polymethyl methacrylate, acrylic or polyarylates, or cycloolefin resin such as ARTON (trade name, manufactured by JSR Corporation) or APEL (trade name, manufactured by Mitsui Chemicals, Inc.).

A coating of an inorganic or organic material or a hybrid coating of a combination thereof may be formed on the surface of the resin film. Such a coating or hybrid coating is preferably a gas barrier film (also referred to as a barrier coating or the like) having a water-vapor permeability of 0.01 g/($m^2$·24 h) or less as measured by the method according to JIS K 7129 (1992) (25±0.5° C., relative humidity 90±2% RH). Such a coating or hybrid coating is more preferably a high gas barrier film having an oxygen permeability of $1\times10^{-3}$ ml/($m^2$·24 h·atm) or less as measured by the method according to JIS K 7126 (1987) and a water-vapor permeability of $1\times10^{-5}$ g/($m^2$·24 h) or less.

Such a gas barrier film may be made of any material having the function of inhibiting the infiltration of water, oxygen, and other substances capable of inducing the degradation of the device. For example, silicon oxide, silicon dioxide, silicon nitride, polysilazane as mentioned above, or the like may be used to form such a gas barrier film. The gas barrier film more preferably has a multilayer structure of such an inorganic layer and a layer of an organic material (organic layer) so that the brittleness of the gas barrier film can be reduced. The inorganic and organic layers may be stacked in any order. Preferably, both are alternately stacked a plurality of times.

The gas barrier film may be formed using any method such vacuum deposition, sputtering, reactive sputtering, molecular beam epitaxy, ionized-cluster beam technique, ion plating, plasma polymerization, atmospheric pressure plasma polymerization, plasma CVD, laser CVD, thermal CVD, or coating. In particular, the gas barrier film is preferably formed by the atmospheric pressure plasma polymerization described in JP 2004-68143 A or by a method of applying vacuum ultraviolet rays at a wavelength of 100 to 230 nm to polysilazane (a liquid containing it) to modify it.

<Counter Electrode (Cathode)>

The counter electrode 5*a* is an electrode film provided to function as a cathode for supplying electrons to the light-emitting functional layer 3. Any of metals, alloys, organic or inorganic conductive compounds, and mixtures thereof may be used to form the counter electrode 5*a*. Specifically, such materials include aluminum, silver, magnesium, lithium, a magnesium-copper mixture, a magnesium-silver mixture, a magnesium-aluminum mixture, a magnesium-indium mixture, indium, a lithium-aluminum mixture, rare earth metals, and oxide semiconductors such as ITO, ZnO, $TiO_2$, and $SnO_2$.

The counter electrode 5*a* can be produced by forming a thin film of any of these conductive materials by a method such as vapor deposition or sputtering. The sheet resistance of the counter electrode 5*a* is preferably not more than several hundred Ω/square, and its thickness is generally selected in the range of 5 nm to 5 μm, preferably in the range of 5 to 200 nm.

When the organic light-emitting device 100 is such that emitted light h is also extracted from the counter electrode 5*a* side, the counter electrode 5*a* should include a highly light-transmitting conductive material, which may be selected from the conductive materials listed above.

<Light-Emitting Layer>

The light-emitting layer 3*c* is a layer for providing a place where electrons and holes injected from the electrodes or adjacent layers are recombined to form excitons for light emission. The light-emitting part may be inside the light-emitting layer 3*c* or at the interface between the light-emitting layer 3*c* and the adjacent layer. The light-emitting layer 3*c* may have any structure as long as the requirements according to the present invention are satisfied.

As a non-limiting example, the total thickness of the light-emitting layer 3*c* is preferably adjusted to fall within the range of 2 nm to 5 μm, more preferably within the range of 2 to 500 nm, even more preferably within the range of 5 to 200 nm so that the film can be uniformly formed, unnecessary high-voltage can be prevented from being applied during light emission, and the stability of luminescent color at the driving current can be improved.

The thickness of individual light-emitting layers is also preferably adjusted to fall within the range of 2 nm to 1 μm, more preferably within the range of 2 to 200 nm, even more preferably within the range of 3 to 150 nm.

The light-emitting layer 3*c* preferably contains a light-emitting dopant (also referred to as a luminescent dopant compound, a dopant compound, or simply a dopant) and a host compound (also referred to as a matrix material, a light-emitting host compound, or simply a host).

(1) Host Compound

The host compound is a compound that plays a role in injecting and transporting mainly charges in the light-emitting layer 3*c*. In the organic light-emitting device, light is not substantially observed from the host compound itself.

The host compound is preferably a compound whose phosphorescence quantum yield is less than 0.1, more preferably less than 0.01, with respect to phosphorescence emission at room temperature (25° C.). The host compound preferably makes up 20% or more of the weight of the compounds in the light-emitting layer 3*c*.

In addition, the energy of the excited state of the host compound is preferably higher than the energy of the excited state of the light-emitting dopant present in the same layer.

A host compound may be used alone, or two or more host compounds may be used together. Using two or more host compounds, charge transfer can be controlled so that the organic light-emitting device can have a high efficiency.

Any host compound conventionally used in organic light-emitting devices may be used in the present invention. The host compound may be a low molecular weight compound, a polymer compound having a repeating unit(s), or a compound having a reactive group such as a vinyl group or an epoxy group.

Known host compounds are preferably such that they have the ability to transport holes or electrons, make it possible to prevent an increase in the emission wavelength, and also have a high glass transition temperature (Tg) so that stable operation of the organic light-emitting device can be achieved during high-temperature driving or against the heat generated during the driving of the device. The Tg is preferably 90° C. or more, more preferably 120° C. or more.

The glass transition point (Tg) is the value determined by the method according to JIS K 7121 using DSC (differential scanning calorimetry).

Examples of known host compounds that may be used for the organic light-emitting device 100 of the present invention include, but are not limited to, compounds described in the following literatures:

JP 2001-257076 A, JP 2002-308855 A, JP 2001-313179 A, JP 2002-319491 A, JP 2001-357977 A, JP 2002-334786 A, JP 2002-8860 A, JP 2002-334787 A, JP 2002-15871 A, JP 2002-334788 A, JP 2002-43056 A, JP 2002-334789 A, JP 2002-75645 A, JP 2002-338579 A, JP 2002-105445 A, JP 2002-343568 A, JP 2002-141173 A, JP 2002-352957 A, JP 2002-203683 A, JP 2002-363227 A, JP 2002-231453 A, JP 2003-3165 A, JP 2002-234888 A, JP 2003-27048 A, JP 2002-255934 A, JP 2002-260861 A, JP 2002-280183 A, JP 2002-299060 A, JP 2002-302516 A, JP 2002-305083 A, JP 2002-305084 A, JP 2002-308837 A, US 2003/0,175,553 A, US 2006/0,280,965 A, US 2005/0,112,407 A, US 2009/0,017,330 A, US 2009/0,030,202 A, US 2005/0,238,919 A, WO 2001/039234 A, WO 2009/021126 A, WO 2008/056746 A, WO 2004/093207 A, WO 2005/089025 A, WO 2007/063796 A, WO 2007/063754 A, WO 2004/107822 A, WO 2005/030900 A, WO 2006/114966 A, WO 2009/086028 A, WO 2009/003898 A, WO 2012/023947 A, JP 2008-074939 A, JP 2007-254297 A, and EP 2034538 A.

(2) Light-Emitting Dopant

The light-emitting dopant will be described.

The light-emitting dopant is preferably a fluorescence-emitting dopant (also referred to as a fluorescent dopant or a fluorescent compound) or a phosphorescence-emitting dopant (also referred to as a phosphorescent dopant or a phosphorescent compound). In the present invention, at least one light-emitting layer 3*c* preferably contains a phosphorescence-emitting dopant.

The concentration of the light-emitting dopant in the light-emitting layer 3*c* may be freely determined based on the specific dopant to be used and the requirements for the device. The light-emitting layer 3*c* may contain the dopant at a concentration uniform in the thicknesswise direction of the layer, or may have a certain dopant concentration distribution in the thicknesswise direction of the layer.

Two or more different light-emitting dopants may be used together, and dopants with different structures may be used together, or a fluorescence-emitting dopant may be used in combination with a phosphorescence-emitting dopant. This makes it possible to obtain any desired luminescent color.

The color of the light emitted from compounds or the organic light-emitting device 100 of the present invention can be determined by measuring the light with a spectral radiance meter CS-1000 (manufactured by Konica Minolta) and determining the color from the measurement results based on the CIE chromaticity coordinates according to FIG. 4.16 on page 108 of Shin-Hen Shikisai Kagaku Handbook (New Handbook of Color Science) (edited by The Color Science Association of Japan, University of Tokyo Press, 1985).

In the present invention, one or more light-emitting layers 3*c* also preferably contain two or more light-emitting dopants with different luminescent colors to produce white emission.

Any combination of light-emitting dopants may be used to produce white emission. For example, a combination of blue and orange dopants, a combination of blue, green, and red dopants, or the like may be used.

The white color of the light from the organic light-emitting device of the present invention is preferably such that the chromaticity of the light according to the CIE 1931 color system at 1,000 cd/$m^2$ falls within the region x=0.39±0.09, y=0.38±0.08 when the 2° view angle front luminance is measured by the above method.

(2.1) Phosphorescence-Emitting Dopant

The phosphorescence-emitting dopant (hereinafter also referred to as the phosphorescent dopant) will be described.

The phosphorescent dopant is such a compound that emission from the excited triplet can be observed. Specifically, the phosphorescent dopant may be defined as a compound that emits phosphorescence at room temperature (25° C.) and has a phosphorescence quantum yield of 0.01 or more at 25° C. The phosphorescence quantum yield is preferably 0.1 or more.

The phosphorescence quantum yield can be measured by the method described on page 398 of The 4th Edition Jikken Kagaku Koza (Handbook of Experimental Chemistry) 7, Bunko (Spectroscopy) II (1992, Maruzen). The phosphorescence quantum yield in a solution can be measured using various solvents. The phosphorescent dopant should have the specified phosphorescence quantum yield (0.01 or more) in any one of such solvents.

There are two principles for light emission from the phosphorescent dopant. One is an energy transfer type, according to which carriers are transported to a host compound and recombined on the host compound, so that the host compound is brought into an excited state, the energy of which is transferred to the phosphorescent dopant so that light is emitted from the phosphorescent dopant.

The other is a carrier trap type, according to which carriers are recombined on the phosphorescent dopant serving as a carrier trap, so that light is emitted from the phosphorescent dopant.

In both cases, it is required that the energy of the excited state of the phosphorescent dopant be lower than the energy of the excited state of the host compound.

The phosphorescent dopant may be appropriately selected from known dopants and used for the light-emitting layer 3*c* of the organic light-emitting device 100.

Examples of known phosphorescent dopants that may be used in the present invention include the compounds described in the following literatures:

Nature 395, 151 (1998), Appl. Phys. Lett. 78, 1622 (2001), Adv. Mater. 19, 739 (2007), Chem. Mater. 17, 3532 (2005), Adv. Mater. 17, 1059 (2005), WO 2009/100991 A, WO 2008/101842 A, WO 2003/040257 A, US 2006/835,469 A, US 2006/0,202,194 A, US 2007/0,087,321 A, US 2005/0,244,673 A, Inorg. Chem. 40, 1704 (2001), Chem. Mater. 16, 2480 (2004), Adv. Mater. 16, 2003 (2004), Angew. Chem. Int. Ed. 2006, 45, 7800, Appl. Phys. Lett. 86, 153505 (2005), Chem. Lett. 34, 592 (2005), Chem. Commun. 2906 (2005), Inorg. Chem. 42, 1248 (2003), WO 2009/050290 A, WO 2002/015645 A, WO 2009/000673 A, US 2002/0,034,656 A, U.S. Pat. No. 7,332,232, US 2009/0,108,737 A, US 2009/0,039,776 A, U.S. Pat. No. 6,921,915, U.S. Pat. No. 6,687,266, US 2007/0,190,359 A, US 2006/0,008,670 A, US 2009/0,165,846 A, US 2008/0,015,355 A, U.S. Pat. No. 7,250,226, U.S. Pat. No. 7,396,598, US 2006/0,263,635 A, US 2003/0,138,657 A, US 2003/0,152,802 A, U.S. Pat. No. 7,090,928, Angew. Chem. Int. Ed. 47, 1 (2008), Chem. Mater. 18, 5119 (2006), Inorg. Chem. 46, 4308 (2007), Organometallics 23, 3745 (2004), Appl. Phys. Lett. 74, 1361 (1999), WO 2002/002714 A, WO 2006/009024 A, WO 2006/056418 A, WO 2005/019373 A, WO 2005/123873 A, WO 2005/123873 A, WO 2007/004380 A, WO 2006/082742 A, US 2006/0,251,923 A, US 2005/0,260,441 A, U.S. Pat. No. 7,393,599, U.S. Pat. No. 7,534,505, U.S. Pat. No. 7,445,855, US 2007/0,190,359 A, US 2008/0,297,033 A, U.S. Pat. No. 7,338,722, US 2002/0,134,984 A, U.S. Pat. No. 7,279,704, US 2006/098,120 A, US 2006/103,874 A, WO 2005/076380 A, WO 2010/032663 A, WO 2008/140115 A, WO 2007/052431 A, WO 2011/134013 A, WO 2011/157339 A, WO 2010/086089 A, WO 2009/113646 A, WO 2012/020327 A, WO 2011/051404 A, WO 2011/004639 A, WO 2011/073149 A, JP 2012-069737 A, JP 2012-195554 A, JP 2009-114086 A, JP 2003-81988 A, JP 2002-302671 A, and JP 2002-363552 A.

In particular, the phosphorescent dopant is preferably an organometallic complex having Ir as a central metal. The phosphorescent dopant is more preferably a complex having at least one coordination moiety from a metal-carbon bond, a metal-nitrogen bond, a metal-oxygen bond, and a metal-sulfur bond.

(2.2) Fluorescence-Emitting Dopant

The fluorescence-emitting dopant (hereinafter also referred to as the "fluorescent dopant") will be described.

The fluorescent dopant may be any compound capable of emitting light from the excited singlet state so that light emission from the excited singlet state can be observed.

Examples of the fluorescent dopant include anthracene derivatives, pyrene derivatives, chrysene derivatives, fluoranthene derivatives, perylene derivatives, fluorene derivatives, arylacetylene derivative, styrylarylene derivative, styrylamine derivatives, arylamine derivatives, boron complexes, coumarin derivatives, pyran derivatives, cyanine derivatives, croconium derivatives, squarylium derivatives, oxobenzanthracene derivatives, fluorescein derivatives, rhodamine derivatives, pyrylium derivatives, perylene derivatives, polythiophene derivatives, or rare earth complex compounds.

In recent years, light-emitting dopants capable of producing delayed fluorescence have been developed. Such dopants may also be used.

Examples of light-emitting dopants capable of producing delayed fluorescence include, but are not limited to, compounds described in WO 2011/156793 A, JP 2011-213643 A, and JP 2010-93181 A.

<Injection Layer: Hole Injection Layer, Electron Injection Layer>

The injection layer is a layer provided between the electrode and the light-emitting layer 3*c* so as to reduce the driving voltage or improve the emission luminance. Such a layer is described in detail in "Yuki EL Soshi to Sono Kogyoka-Saizensen" (Organic EL Devices and Forefront of Their Industrialization), published by NTS Inc., Nov. 30, 1998, Part 2, Chapter 2, "Denkyoku Zairyou" (Electrode Materials), pages 123-166. Examples include a hole injection layer 3*a* and an electron injection layer 3*e*.

The injection layer may be provided as needed. The hole injection layer 3*a* may be provided between the anode and the light-emitting layer 3*c* or a hole transport layer 3*b*. The electron injection layer 3*e* may be provided between the cathode and the light-emitting layer 3*c* or an electron transport layer 3*d*.

The hole injection layer 3*a* is also described in detail in publications such as JP 09-45479 A, JP 09-260062 A, and JP 08-288069 A. Examples include a layer of a phthalocyanine such as copper phthalocyanine, a layer of an oxide such as vanadium oxide, an amorphous carbon layer, and a polymer layer including a conductive polymer such as polyaniline (Emeraldine) or polythiophene.

The electron injection layer 3*e* is also described in detail in publications such as JP 06-325871 A, JP 09-17574 A, and JP 10-74586 A. Examples include a layer of a metal such as strontium or aluminum, a layer of an alkali metal halide such as potassium fluoride, a layer of an alkaline-earth metal compound such as magnesium fluoride, and a layer of an oxide such as molybdenum oxide. In the present invention, the electron injection layer 3*e* is preferably a very thin film whose thickness is preferably in the range of 1 nm to 10 μm although it depends on the material.

<Hole Transport Layer>

The hole transport layer 3*b* includes a hole transport material having the function of transporting holes. In a broad sense, the hole injection layer 3*a* and an electron-blocking layer fall within the category of the hole transport layer 3*b*. The hole transport layer 3*b* may be a single layer or a multilayer structure.

The hole transport material has one of the ability to inject or transport holes and the ability to block electrons. The hole transport material may be any of organic and inorganic materials. Examples include triazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, aniline-based copolymers, and conductive high-molecular oligomers, specifically, thiophene oligomers.

The hole transport material may be any of the above materials. Preferably, the hole transport material is any of a porphyrin compound, an aromatic tertiary amine compound, and a styrylamine compound. In particular, an aromatic tertiary amine compound is preferably used.

Typical examples of the aromatic tertiary amine compound and the styrylamine compound include N,N,N',N'-tetraphenyl-4,4'-diaminophenyl, N,N'-diphenyl-N,N'-bis(3-methylphenyl)-[1,1'-biphenyl]-4,4'-diamine (TPD), 2,2-bis(4-di-p-tolylaminophenyl)propane, 1,1-bis(4-di-p-tolylaminophenyl)cyclohexane, N,N,N',N'-tetra-p-tolyl-4,4'-diaminobiphenyl, 1,1-bis(4-di-p-tolylaminophenyl)-4-phenylcyclohexane, bis(4-dimethylamino-2-methylphenyl)phenylmethane, bis(4-di-p-tolylaminophenyl)phenylmethane, N,N'-diphenyl-N,N'-di(4-methoxyphenyl)-4,4'-diaminobiphenyl, N,N,N',N'-tetraphenyl-4,4'-diaminodiphenyl ether, 4,4'-bis(diphenylamino)quadriphenyl, N,N,N-tri(p-tolyl)amine, 4-(di-p-tolylamino)-4'-[4-(di-p-tolylamino)styryl]stilbene, 4-N,N-diphenylamino-(2-diphenylvinyl)benzene, 3-methoxy-4-N, N-diphenylaminostilbenzene, N-phenylcarbazole, compounds described in U.S. Pat. No. 5,061,569, having two condensed aromatic rings in their molecule, such as 4,4'-bis[N-(1-naphthyl)-N-phenylamino]biphenyl (NPD), and compounds described in JP 04-308688 A, having three triphenylamine units linked in a starburst manner, such as 4,4',4"-tris[N-(3-methylphenyl)-N-phenylamino]triphenylamine (MTDATA).

Polymer materials having any of these materials incorporated in the polymer chain or polymer materials whose main chain is formed using any of these materials may also be used. In addition, p-type Si and inorganic compounds such as p-type SiC may also be used as hole injection or transport materials.

In addition, materials described in JP 11-251067 A and J. Huang et. al., Applied Physics Letters, 80 (2002), p. 139 may also be used, such as what are called p-type hole transport materials. In the present invention, these materials are preferably used because they can form high-efficiency light-emitting devices.

The thickness of the hole transport layer 3*b* is generally, but not limited to, about 5 nm to about 5 μm, preferably 5 to 200 nm. The hole transport layer 3*b* may be a single layer structure including one or more of the above materials.

The material for the hole transport layer 3*b* may be doped with an impurity for increasing the p-conductivity. Examples of such an impurity include those described in JP 04-297076 A, JP 2000-196140 A, JP 2001-102175 A, and J. Appl. Phys., 95, 5773 (2004).

Preferably, when the p-conductivity of the hole transport layer 3*b* is increased in this way, low power consumption devices can be produced.

<Electron Transport Layer>

The electron transport layer 3*d* includes a material having the function of transporting electrons. In a broad sense, the electron injection layer 3*e* and a hole-blocking layer (not shown) fall within the category of the electron transport layer 3*d*. The electron transport layer 3*d* may be formed as a single layer structure or a multilayer structure.

In the electron transport layer 3*d* of a single layer structure or a multilayer structure, the electron transport material (also serving as a hole-blocking material) constituting the layer part adjacent to the light-emitting layer 3*c* only needs to have the function of transmitting electrons to the light-emitting layer 3*c* when the electrons are injected from the cathode. The material with such properties may be any material selected from conventionally known compounds. Examples of such compounds include nitro-substituted fluoren derivatives, diphenylquinone derivatives, thiopyran dioxide derivatives, carbodiimide, fluorenylidenemethane derivatives, anthraquinodimethane, anthrone derivatives, oxadiazole derivatives, and the like. Materials that may be used for the electron transport layer 3*d* also include thiadiazole derivatives derived from the oxadiazole derivatives by replacing the oxygen atom in the oxadiazole ring with a sulfur atom; and quinoxaline derivatives having a quinoxaline ring known as an electron-withdrawing group. Polymer materials having any of these materials incorporated in the polymer chain or polymer materials whose main chain is formed using any of these materials may also be used.

Materials that may be used for the electron transport layer 3*d* also include 8-quinolinol derivative metal complexes such as tris(8-quinolinol)aluminum ($Alq_3$), tris(5,7-dichloro-8-quinolinol)aluminum, tris(5,7-dibromo-8-quinolinol)aluminum, tris(2-methyl-8-quinolinol)aluminum, tris(5-methyl-8-quinolinol)aluminum, and bis(8-quinolinol) zinc (Znq), and metal complexes derived from any of these metal complexes by replacing the central metal with In, Mg, Cu, Ca, Sn, Ga, or Pb.

Alternatively, metal-free- or metallo-phthalocyanine or a compound derived therefrom by substitution with an alkyl group, a sulfonic acid group, or the like at the end is also preferably used as the material for the electron transport layer 3*d*. Materials that may be used for the electron transport layer 3*d* also include distyrylpyrazine derivatives, which may also be used as materials for the light-emitting layer 3*c*. Similarly to the hole injection layer 3*a* or the hole transport layer 3*b*, inorganic semiconductors such as n-type Si and n-type SiC may also be used as materials for the electron transport layer 3*d*.

The thickness of the electron transport layer 3*d* is generally, but not limited to, about 5 nm to about 5 μm, preferably 5 to 200 nm. The electron transport layer 3*d* may be a single layer structure including one or more of the above materials.

The material for the electron transport layer 3*d* may be doped with an impurity for increasing the n-conductivity. Examples of such an impurity include those described in JP 04-297076 A, JP 10-270172 A, JP 2000-196140 A, JP 2001-102175 A, and J. Appl. Phys., 95, 5773 (2004). The electron transport layer 3*d* preferably contains potassium or a potassium compound. The potassium compound may be, for example, potassium fluoride, or the like. When the n-conductivity of the electron transport layer 3*d* is increased in this way, lower power consumption devices can be produced.

The material (electron-transporting compound) used to form the electron transport layer 3*d* may be the same as the material used to form the underlying layer 1*a*. This also applies to the electron transport layer 3*d* for also serving as the electron injection layer 3*e*, and it may be made of the same material as the material used to form the underlying layer 1*a*.

<Blocking Layer: Hole-Blocking Layer, Electron-Blocking Layer>

As mentioned above, the blocking layer is optionally provided in addition to the basic constituent layer of an organic compound thin film. For example, JP 11-204258 A, JP 11-204359 A, and "Yuki EL Soshi to Sono Kogyoka-Saizensen" (Organic EL Devices and Forefront of Their Industrialization), published by NTS Inc., Nov. 30, 1998, page 237 describe hole-blocking (hole-block) layers.

In a broad sense, the hole-blocking layer has the function of an electron transport layer 3*d*. The hole-blocking layer includes a hole-blocking material having the function of transporting electrons and a very low ability to transport holes so that it can increase the probability of recombination of electrons and holes by transporting electrons and blocking holes. If necessary, the composition of the electron transport layer 3*d* may be used to form the hole-blocking layer. The hole-blocking layer is preferably provided adjacent to the light-emitting layer 3*c*.

In a broad sense, the electron-blocking layer has the function of a hole transport layer 3*b*. The electron-blocking layer includes a material having the function of transporting holes and a very low ability to transport electrons so that it can increase the probability of recombination of electrons and holes by transporting holes and blocking electrons. If necessary, the composition of the hole transport layer 3*b* may be used to form the electron-blocking layer. The hole-blocking layer preferably has a thickness in the range of 3 to 100 nm, more preferably in the range of 5 to 30 nm.

<Auxiliary Electrode>

The auxiliary electrode 15, which is provided to reduce the resistance of the transparent electrode 1, is provided in contact with the electrode layer 1*b* of the transparent electrode 1. The auxiliary electrode 15 is preferably made of a low-resistance metal such as gold, platinum, silver, copper, or aluminum. Since these metals have low optical transparency, the auxiliary electrode 15 should be patterned so that the extraction of emitted light h from a light extraction surface 13*a* will not be affected.

The method for forming the auxiliary electrode 15 with such properties may be vapor deposition, sputtering, printing, ink-jetting, or aerosol jetting. In view of the numerical aperture for light extraction, the auxiliary electrode 15 preferably has a line width of 50 μm or less. In view of conductivity, the auxiliary electrode 15 preferably has a thickness of 1 μm or more.

<Extraction Electrode>

The extraction electrode 16 is provided to electrically connect the transparent electrode 1 to an external power source. The material for the extraction electrode 16 is not restricted, and a known material is preferably used to form the extraction electrode 16. The extraction electrode 16 may be, for example, a metal film such as an MAM electrode with a three-layer structure (Mo/Al—Nd alloy/Mo).

<Sealant>

The sealant 17 is provided to cover the organic light-emitting device 100. The sealant 17 may be a sheet-shaped (film-shaped) sealing member, which is bonded to the transparent substrate 13 side with an adhesive 19, or a sealing film. In such a case, the sealant 17 is provided to cover at least the light-emitting functional layer 3 while the terminal parts of the transparent electrode 1 and the counter electrode 5*a* of the organic light-emitting device 100 are exposed. The sealant 17 may also be provided with electrodes, and the terminal parts of the transparent electrode 1 and the counter electrode 5*a* of the organic light-emitting device 100 may be electrically connected to the electrodes, respectively.

The sheet-shaped (film-shaped) sealant 17 may be, for example, a glass base material, a polymer base material, a metal base material, or the like. These base materials may be formed into thinner films. Specifically, the glass base material may be soda-lime glass, barium/strontium-containing glass, lead glass, aluminosilicate glass, borosilicate glass, barium borosilicate glass, quartz, or the like. The polymer base material may be polycarbonate, acrylic, polyethylene terephthalate, polyether sulfide, polysulfone, or the like. The metal base material may include at least one metal selected from the group consisting of stainless steel, iron, copper, aluminum, magnesium, nickel, zinc, chromium, titanium, molybdenum, silicon, germanium, and tantalum, or an alloy thereof.

In particular, a thin film of the polymer base material or the metal base material is preferably used as the sealant 17, so that the device can be obtained in the form of a thin film.

In addition, such a film of the polymer base material preferably has an oxygen permeability of $1\times10^{-3}$ ml/($m^2$·24 h·atm) or less as measured by the method according to JIS K 7126 (1987) and a water-vapor permeability of $1\times10^{-3}$ g/($m^2$·24 h) or less (25±0.5° C., relative humidity (90±2)% RH) as measured by the method according to JIS K 7129 (1992).

The base material described above may also be formed into a concave sheet and then used as the sealant 17. In this case, the base material member may be subjected to sandblasting, chemical etching, or other processes so that a concave shape is formed.

An adhesive 19 is used to bond such a sheet-shaped sealant 17 to the substrate 13 side. The adhesive 19 is used as a sealing agent for sealing the organic light-emitting device 100 sandwiched between the sealant 17 and the transparent substrate 13. Specifically, the adhesive 19 may be a photo-curing or thermosetting adhesive having a reactive vinyl group of an acrylic acid oligomer or a methacrylic acid oligomer, or a moisture-curing adhesive such as 2-cyanoacrylic acid ester.

Alternatively, the adhesive 19 may be of a thermosetting and chemical setting type (two-part mixing type) such as an epoxy adhesive. A hot melt adhesive such as polyamide, polyester, or polyolefin may also be used. A cationic curing or ultraviolet curing epoxy resin adhesive may also be used.

Some organic materials used to form the organic light-emitting device 100 may be degraded by heat treatment. Therefore, the adhesive 19 is preferably such that it can be bonded and cured at a temperature from room temperature (25° C.) to 80° C. A desiccant may also be dispersed in the adhesive 19.

A commercially available disperser may be used to apply the adhesive 19 to the part where the sealant 17 and the transparent substrate 13 are to be bonded, or the adhesive 19 may be applied by printing such as screen printing.

When a gap is formed between the sheet-shaped sealant 17, the transparent substrate 13, and the adhesive 19, inert gas such as nitrogen or argon or inert liquid such as fluorinated hydrocarbon or silicone oil is preferably injected into the gap in a gas or liquid phase. Alternatively, vacuum may also be used. In addition, a moisture absorbing compound may also be sealed inside.

Examples of the moisture absorbing compound include metal oxides (such as sodium oxide, potassium oxide, calcium oxide, barium oxide, magnesium oxide, and aluminum oxide), sulfates (such as sodium sulfate, potassium sulfate, magnesium sulfate, and cobalt sulfate), metal halides (such as calcium chloride, magnesium chloride, cesium fluoride, tantalum fluoride, cerium bromide, magnesium bromide, barium iodide, and magnesium iodide), and perchlorates (such as barium perchlorate and magnesium perchlorate). Anhydrous salts are preferably used for sulfates, metal halides, and perchlorates.

On the other hand, a sealing film may be used as the sealant 17. In this case, the sealing film is provided on the transparent substrate 13 in such a way that the light-emitting functional layer 3 of the organic light-emitting device 100 is completely covered while the terminal parts of the transparent electrode 1 and the counter electrode 5*a* of the organic light-emitting device 100 are exposed.

Such a sealing film is made of an inorganic or organic material. Such a sealing film should be made of a material having the function of preventing the entry of water, oxygen, and other substances capable of degrading the light-emitting functional layer 3 of the organic light-emitting device 100. Such a material may be, for example, an inorganic material such as silicon oxide, silicon dioxide, or silicon nitride. To improve the brittleness of the sealing film, an organic material film may also be used together with the inorganic material film to form a multilayer structure.

These films may be formed by any method such as vacuum vapor deposition, sputtering, reactive sputtering, molecular beam epitaxy, ionized cluster beam technique, ion plating, plasma polymerization, atmospheric pressure plasma polymerization, plasma CVD, laser CVD, thermal CVD, or coating.

<Protective Film or Protective Sheet>

Although not shown, a protective film or a protective sheet may be provided in such a way that the organic light-emitting device 100 and the sealant 17 are sandwiched between the transparent substrate 13 and the protective film or sheet. The protective film or sheet is provided to mechanically protect the organic light-emitting device 100. Particularly when the sealant 17 is a sealing film, the protective film or sheet is preferably provided because the mechanical protection of the organic light-emitting device 100 by the sealing film is not sufficient.

The protective film or sheet may be a glass sheet, a polymer sheet, a polymer film thinner than the above, a metal sheet, a metal film thinner than the metal sheet, a polymer material film, or a metal material film. In particular, a polymer film is preferably used in view of lightweight and thickness reduction.

<Method for Manufacturing Organic Light-Emitting Device>

As an example, a method for manufacturing the organic light-emitting device 100 shown in FIG. 1 will be described in this section.

First, a resin material solution containing dispersed particles with an average particle size of 0.2 μm or more is applied to a transparent substrate 13 to form a scattering layer 2*a*. Next, a resin material solution containing dispersed particles with an average particle size in the range of 5 to 70 nm is applied to the scattering layer 2*a* to form a smooth layer 2*b*, so that an internal light extraction layer 2 is formed.

An underlying layer 1*a*, for example, including a nitrogen atom-containing compound is then formed with a thickness of 1 μm or less, preferably 10 to 100 nm, on the internal light extraction layer 2 (smooth layer 2*b*) by vapor deposition or any other suitable method.

An electrode layer 1*b* including silver (or an alloy including silver as a main component) is then formed with a thickness of 12 nm or less, preferably 4 to 9 nm, on the underlying layer 1*a* by vapor deposition or any other suitable method, so that a transparent electrode 1 as an anode is formed. At the same time, an extraction layer 16 for connection to an external power source is formed at the end of the transparent electrode 1 by vapor deposition or any other suitable method.

Subsequently, a hole injection layer 3*a*, a hole transport layer 3*b*, a light-emitting layer 3*c*, an electron transport layer 3*d*, and an electron injection layer 3*e* are sequentially deposited thereon to form a light-emitting functional layer 3. Each of these layers may be deposited by spin coating, casting, ink-jetting, vapor deposition, printing, or the like. Vacuum vapor deposition or spin coating is particularly preferred because it can easily form a uniform film and is less likely to form pinholes. The deposition method used may also differ from layer to layer. When vapor deposition is used to form each layer, the deposition conditions, although varying with the type of the compound used and other factors, are preferably selected as appropriate from the following common ranges: boat heating temperature 50 to 450° C., the degree of vacuum $1\times10^{-6}$ to $1\times10^{-2}$ Pa, deposition rate 0.01 to 50 nm/sec, substrate temperature −50 to 300° C., film thickness 0.1 to 5 μm.

After the light-emitting functional layer 3 is formed as described above, a counter electrode 5*a* for serving as a cathode is formed thereon by a suitable deposition method such as vapor deposition or sputtering. In this process, the counter electrode 5*a* is formed and patterned to have a terminal part extending from the top of the light-emitting functional layer 3 to the edge of the transparent substrate 13, while it is insulated from the transparent electrode 1 with the light-emitting functional layer 3. In this way, an organic light-emitting device 100 is obtained. Subsequently, a transparent sealant 17 is provided to cover at least the light-emitting functional layer 3 while the terminal parts of the transparent electrode 1 (extraction electrode 16) and the counter electrode 5*a* of the organic light-emitting device 100 are exposed.

Thus, the desired organic light-emitting device 100 is obtained on the transparent substrate 13. When the organic light-emitting device 100 is manufactured in this way, it is preferable to continuously form the components from the light-emitting functional layer 3 to the counter electrode 5*a* in a single vacuum pumping process. Alternatively, however, the transparent substrate 13 may be taken out of the vacuum atmosphere in midstream and then subjected to a different deposition process. In such a case, it is necessary to adopt special measures such as operation under a dry inert gas atmosphere.

A DC voltage of about 2 to about 40 V may be applied to the organic light-emitting device 100 obtained as described above, in which the transparent electrode 1 is a plus pole (anode) and the counter electrode 5*a* is a minus pole (cathode), so that light emission can be observed. Alternatively, an AC voltage may be applied. The AC voltage applied may have any waveform.

<Advantageous Effects of Organic Light-Emitting Device>

The organic light-emitting device 100 of the present invention described above includes the transparent electrode 1, which has both conductivity and optical transparency, the transparent substrate 13, and the internal light extraction layer 2 provided between the transparent electrode 1 and the transparent substrate 13. This structure makes it possible to reduce total reflection loss between the transparent electrode 1 and the transparent substrate 13 and to improve luminous efficiency.

The organic light-emitting device 100 includes the transparent electrode 1 as an anode, the light-emitting functional layer 3 provided thereon, and the counter electrode 5*a* as a cathode provided thereon. In this structure, a sufficient voltage can be applied across the transparent electrode 1 and the counter electrode 5*a*, so that the organic light-emitting device 100 can emit light with high luminance and the efficiency of extraction of emitted light h from the transparent electrode 1 side can be improved, so that high luminance can be achieved. In addition, the driving voltage for a certain level of luminance can also be reduced, so that the emission lifetime can be extended.

Second Embodiment

A second embodiment differs from the first embodiment mainly in the features mentioned below.

<Structure of Organic Light-Emitting Device>

An organic light-emitting device 200 shown in FIG. 8 differs from the organic light-emitting device 100 described with reference to FIG. 1 in that the transparent electrode 1 is used as a cathode.

Figure 8:
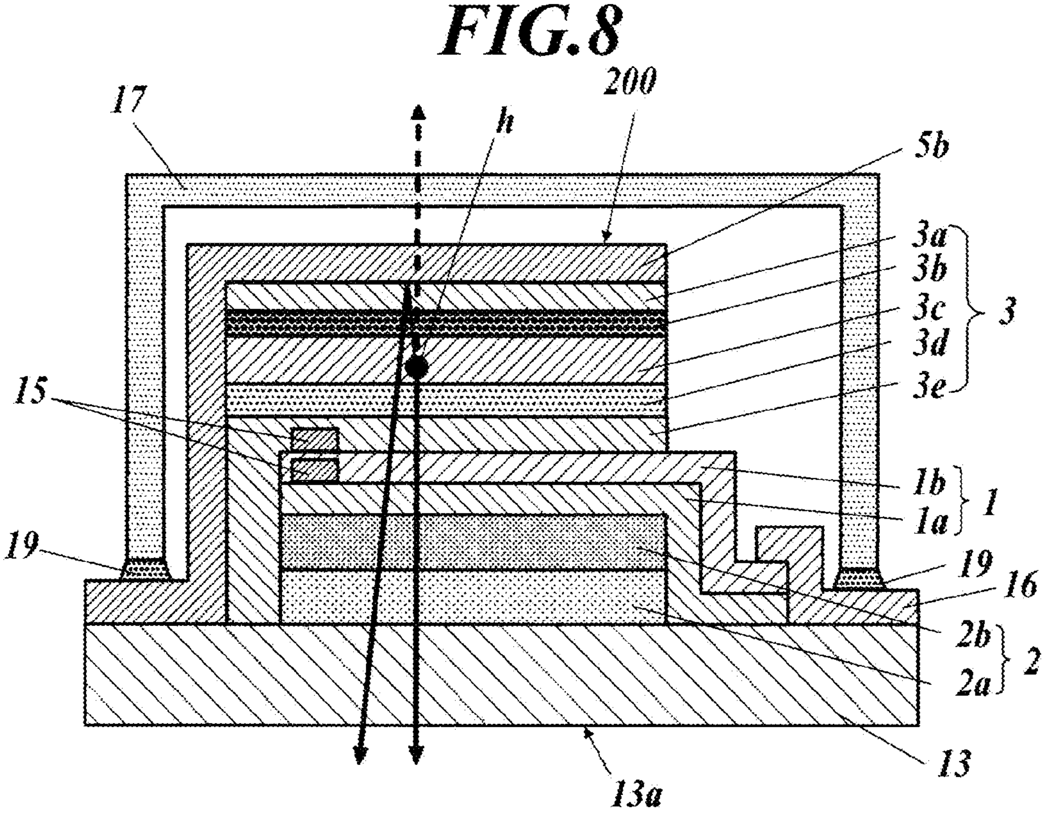
FIG. 8 is a schematic cross-sectional view showing the structure of an organic light-emitting device according to a second embodiment.

As shown in FIG. 8, the organic light-emitting device 200 is provided on a transparent substrate 13 and includes an internal light extraction layer 2 and a transparent electrode 1, which are characterized by being as described above and provided on the transparent substrate 13 in the same manner as in the first embodiment.

Therefore, the organic light-emitting device 200 is so configured that emitted light h is extracted from at least the transparent substrate 13 side. However, the transparent electrode 1 is used as a cathode (negative pole). Therefore, the counter electrode 5*b* is used as an anode.

In such a case, the layer structure of the organic light-emitting device 200 is not limited to the example described below and may be any common layer structure as in the first embodiment.

As an example in this embodiment, an illustrative structure includes an electron injection layer 3*e*, an electron transport layer 3*d*, a light-emitting layer 3*c*, a hole transport layer 3*b*, and a hole injection layer 3*a*, which are stacked in this order on the top of the transparent electrode 1 for functioning as a cathode. Among these components, the light-emitting layer 3*c* including at least an organic material is an essential component.

Besides these layers, the light-emitting functional layer 3 may include any of various optional components as described for the first embodiment. In the structure shown above, only the part where the light-emitting functional layer 3 is sandwiched between the transparent electrode 1 and the counter electrode 5*b* serves as a light-emitting region in the organic light-emitting device 200 similarly to the first embodiment.

In order to reduce the resistance of the transparent electrode 1, the layer structure shown above may also include an auxiliary electrode 15 in contact with the electrode layer 1*b* of the transparent electrode 1 as in the first embodiment.

In this structure, any of a metal, an alloy, an organic or inorganic conductive compound, and any mixture thereof may be used to form the counter electrode 5*b* for serving as an anode. Specific examples include a metal such as gold (Au), copper iodide (CuI), and oxide semiconductors such as ITO, ZnO, $TiO_2$, and $SnO_2$.

The counter electrode 5*b* can be produced by forming a thin film of any of these conductive materials by a method such as vapor deposition or sputtering. The sheet resistance of the counter electrode 5*b* is preferably not more than several hundred Ω/square, and the counter electrode 5*b* generally has a thickness selected in the range of 5 nm to 5 μm, preferably in the range of 5 to 200 nm.

When emitted light h is also extracted from the counter electrode 5*b* side in the organic light-emitting device 200, the counter electrode 5*b* should include a highly light-transmitting conductive material, which may be selected from the conductive materials listed above.

The organic light-emitting device 200 configured as described above is sealed with a sealant 17 for preventing the degradation of the light-emitting functional layer 3 as in the first embodiment.

The detailed features of each of the principal layers (exclusive of the counter electrode 5*b* used as an anode) in the organic light-emitting device 200 described above and the method for manufacturing the organic light-emitting device 200 are the same as those in the first embodiment. Therefore, the description of such details is omitted here.

<Advantageous Effects of Organic Light-Emitting Device>

The organic light-emitting device 200 of the present invention described above includes the transparent electrode 1, which has both conductivity and optical transparency, the transparent substrate 13, and the internal light extraction layer 2 provided between the transparent electrode 1 and the transparent substrate 13. This structure makes it possible to reduce total reflection loss between the transparent electrode 1 and the transparent substrate 13 and to improve luminous efficiency.

The organic light-emitting device 200 includes the transparent electrode 1 as a cathode, the light-emitting functional layer 3 provided thereon, and the counter electrode 5*b* as an anode provided thereon. In this structure, a sufficient voltage can be applied across the transparent electrode 1 and the counter electrode 5*b* as in the first embodiment, so that the organic light-emitting device 200 can emit light with high luminance and the efficiency of extraction of emitted light h from the transparent electrode 1 side can be improved, so that high luminance can be achieved. In addition, the driving voltage for a certain level of luminance can also be reduced, so that the emission lifetime can be extended.

Third Embodiment

A third embodiment differs from the first embodiment mainly in the features mentioned below.

<Structure of Organic Light-Emitting Device>

An organic light-emitting device 300 shown in FIG. 9 differs from the organic light-emitting device 100 described with reference to FIG. 1 in that a counter electrode 5*c* is provided on the substrate 131 side and a light-emitting functional layer 3, a transparent electrode 1, and an internal light extraction layer 2 are provided in this order on the counter electrode 5*c*.

Figure 9:
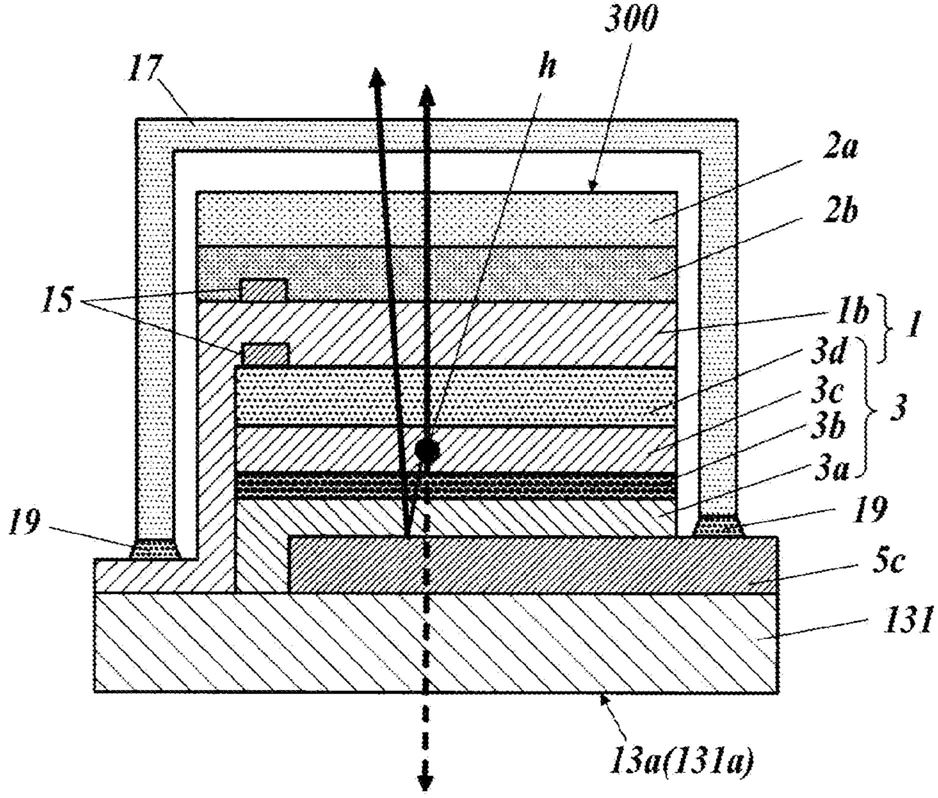
FIG. 9 is a schematic cross-sectional view showing the structure of an organic light-emitting device according to a third embodiment.

As shown in FIG. 9, the organic light-emitting device 300 is provided on the substrate 131 and includes the counter electrode 5*c* for serving as an anode, the light-emitting functional layer 3, the transparent electrode 1 for serving as a cathode, and the internal light extraction layer 2, which are stacked in order from the substrate 131 side. Among these components, the internal light extraction layer 2 and the transparent electrode 1 are characterized by being as described above. Therefore, the organic light-emitting device 300 is so configured that emitted light h is extracted from at least the transparent electrode 1 side opposite to the substrate 131.

In such a case, the layer structure of the organic light-emitting device 300 is not restricted and may be any common layer structure as in the first embodiment.

As an example in this embodiment, an illustrative structure includes a hole injection layer 3*a*, a hole transport layer 3*b*, a light-emitting layer 3*c*, and an electron transport layer 3*d*, which are stacked in this order on the top of the counter electrode 5*c* for functioning as an anode. Among these components, the light-emitting layer 3*c* including at least an organic material is an essential component. The electron transport layer 3*d* also serves as the electron injection layer 3*e* and is provided to have the ability to inject electrons.

The characteristic features of the organic light-emitting device 300 of this embodiment are that the electron transport layer 3*d* having the ability to inject electrons is provided as the underlying layer 1*a* of the transparent electrode 1. In this embodiment, therefore, the transparent electrode 1 for use as a cathode includes the underlying layer 1*a* and the electrode layer 1*b* provided thereon, wherein the underlying layer 1*a* also serves as the electron transport layer 3*d* having the ability to inject electrons.

It is important that the electron transport layer 3*d* with such properties includes the material described above for the underlying layer 1*a* of the transparent electrode 1.

Besides these layers, the light-emitting functional layer 3 may include any of various optional components as described for the first embodiment, except that no electrode injection layer or no hole-blocking layer is provided between the electrode layer 1*b* of the transparent electrode 1 and the electron transport layer 3*d* also serving as the underlying layer 1*a* of the transparent electrode 1. In the structure shown above, only the part where the light-emitting functional layer 3 is sandwiched between the transparent electrode 1 and the counter electrode 5*c* serves as a light-emitting region in the organic light-emitting device 300 similarly to the first embodiment.

In order to reduce the resistance of the transparent electrode 1, the layer structure shown above may also include an auxiliary electrode 15 in contact with the electrode layer 1*b* of the transparent electrode 1 as in the first embodiment.

Any of a metal, an alloy, an organic or inorganic conductive compound, and any mixture thereof may also be used to form the counter electrode 5*c* for serving as an anode. Specific examples include a metal such as gold (Au), copper iodide (CuI), and oxide semiconductors such as ITO, ZnO, $TiO_2$, and $SO_2$.

The counter electrode 5*c* can be produced by forming a thin film of any of these conductive materials by a method such as vapor deposition or sputtering. The sheet resistance of the counter electrode 5*c* is preferably not more than several hundred Ω/square, and the counter electrode 5*c* generally has a thickness selected in the range of 5 nm to 5 μm, preferably in the range of 5 to 200 nm.

When emitted light h is also extracted from the counter electrode 5*c* side in the organic light-emitting device 300, the counter electrode 5*c* should include a highly light-transmitting conductive material, which may be selected from the conductive materials listed above.

The substrate 131 may be transparent or opaque. When emitted light h is also extracted from the counter electrode 5*c* side, the substrate 131 may be the same as the transparent substrate 13 shown in the first embodiment. In this case, the outside-facing surface of the substrate 131 serves as a light extraction surface 131*a*.

When opaque, the substrate 131 may be a substrate of a metal such as aluminum or stainless steel, a film, an opaque resin substrate, a ceramic substrate, or the like.

<Advantageous Effects of Organic Light-Emitting Device>

The organic light-emitting device 300 of the present invention described above includes the transparent electrode 1, which has both conductivity and optical transparency, and the internal light extraction layer 2 provided on the transparent electrode 1. This structure makes it possible to reduce total reflection loss between the transparent electrode 1 and the outside air and to improve luminous efficiency.

In the organic light-emitting device 300, the electron transport layer 3*d* forming the uppermost part of the light-emitting functional layer 3 and having the ability to inject electrons is used as the underlying layer 1*a*, on which the electrode layer 1*b* is provided, and the transparent electrode 1 including the underlying layer 1*a* and the electrode layer 1*b* provided therein is used as a cathode. In this structure, a sufficient voltage can be applied across the transparent electrode 1 and the counter electrode 5*c* as in the first and second embodiments, so that the organic light-emitting device 300 can emit light with high luminance and the efficiency of extraction of emitted light h from the transparent electrode 1 side can be improved, so that high luminance can be achieved. In addition, the driving voltage for a certain level of luminance can also be reduced, so that the emission lifetime can be extended. When the counter electrode 5*c* is optically transparent in the structure described above, emitted light h can also be extracted from the counter electrode 5*c* side.

This embodiment has shown a structure in which the underlying layer 1*a* of the transparent electrode 1 also serves as the electron transport layer 3*d* having the ability to inject electrons. Alternatively, the underlying layer 1*a* may also serve as an electron injection layer or an electron transport layer 3*d* with no ability to inject electrons. When the underlying layer 1*a* is formed as a very thin film to the extent where the light-emitting function is not affected, the underlying layer 1*a* does not need to have the ability to transport or inject electrons.

Also when the underlying layer 1*a* of the transparent electrode 1 is formed as a very thin film to the extent where the light-emitting function is not affected, the counter electrode 5*c* on the substrate 131 side may be used as a cathode, and the transparent electrode 1 on the light-emitting functional layer 3 may be used as an anode. In this case, the light-emitting layer 3 includes, for example, an electron injection layer 3*e*, an electron transport layer 3*d*, a light-emitting layer 3*c*, a hole transport layer 3*b*, and a hole injection layer 3*a*, which are stacked in order from the counter electrode 5*c* (cathode) side on the substrate 131. In addition, the transparent electrode 1 having a multilayer structure composed of a very thin underlying layer 1*a* and an electrode layer 1*b* is provided as an anode on the top of the light-emitting layer 3.

<<Applications of Organic Light-Emitting Device>>

The organic light-emitting devices having the structures described above respectively are surface emitting devices and therefore can be used as a variety of light-emitting sources. Examples include illumination devices such as domestic lightings and vehicle interior lightings, backlights for watches and liquid crystal devices, lightings for sign advertisements, light sources for signals, light sources for optical recording media, light sources for electro-photographic copiers, light sources for optical communication processors, light sources for optical sensors, and the like. However, these are non-limiting, and the devices can be effectively used in other applications, specifically, as backlights or illumination sources for use in combination with color filters for liquid crystal displays.

The organic light-emitting device of the present invention may also be used as a certain type of lamp for illumination or an exposure light source. The organic light-emitting device of the present invention may also be used for projection devices of an image projection type or displays on which viewers directly see still or moving images. In this case, a larger light-emitting surface may be formed by a technique what is called tiling, in which light-emitting panels each having the organic light-emitting device are two-dimensionally joined together for a recent larger illumination device or display.

When the device is used in a display for reproducing moving images, the driving method may be of simple matrix (passive matrix) type or active matrix type. A color or full-color display can also be produced using two or more types of organic light-emitting devices according to the present invention that emit light in different colors.

In the following, an illumination device will be described as an example of use, and then another illumination device having a light-emitting surface increased by tiling will be described.

<Illumination Device 1>

An illumination device according to the present invention has the organic light-emitting device described above.

The organic light-emitting device for use in the illumination device according to the present invention may be designed to have a resonator structure incorporated in each structure described above. Examples of the purpose of the organic light-emitting device having the resonator structure include, but are not limited to, light sources for optical recording media, light sources for electro-photographic copiers, light sources for optical communication processors, and light sources for optical sensors. The device may also be designed to perform laser oscillation for use in the above applications.

The materials used to form the organic light-emitting device of the present invention can be used to form an organic light-emitting device capable of emitting substantially white light (also referred to as a white organic light-emitting device). For example, light in multiple colors may be emitted simultaneously using multiple luminescent materials and mixed to produce white light emission. The combination of multiple colors may include three maximum emission wavelengths for three primary colors, red, green, and blue, or include two maximum emission wavelengths in complementary color relationship, such as blue and yellow or blue green and orange.

The combination of luminescent materials to produce multiple luminescent colors may be either a combination of two or more materials capable of emitting different types of phosphorescence or fluorescence or a combination of a luminescent material capable of emitting fluorescence or phosphorescence and a dye material capable of emitting light using, as exciting light, the light from the luminescent material. A white organic light-emitting device may also use a mixture of two or more light-emitting dopants.

Such a white organic light-emitting device emits white light by itself in contrast to a structure including organic light-emitting devices for different emission colors separately arranged parallel in an array to produce white light emission. When such a device is produced, therefore, no mask is required in forming almost all the layers of the device, and the film can be formed over a surface by vapor deposition, casting, spin-coating, ink-jetting, or printing, which improves the productivity.

The light-emitting layer of such a white organic light-emitting device may be formed using any luminescent materials. For example, for a backlight in a liquid crystal display, any suitable materials may be selected from the above metal complexes and known luminescent materials and so combined that they can be adapted to the wavelength range corresponding to the CF (color filter) characteristics and can produce white color.

Using the white organic light-emitting device described above, an illumination device capable of emitting substantially white light can be obtained.

<Illumination Device 2>

Figure 10:
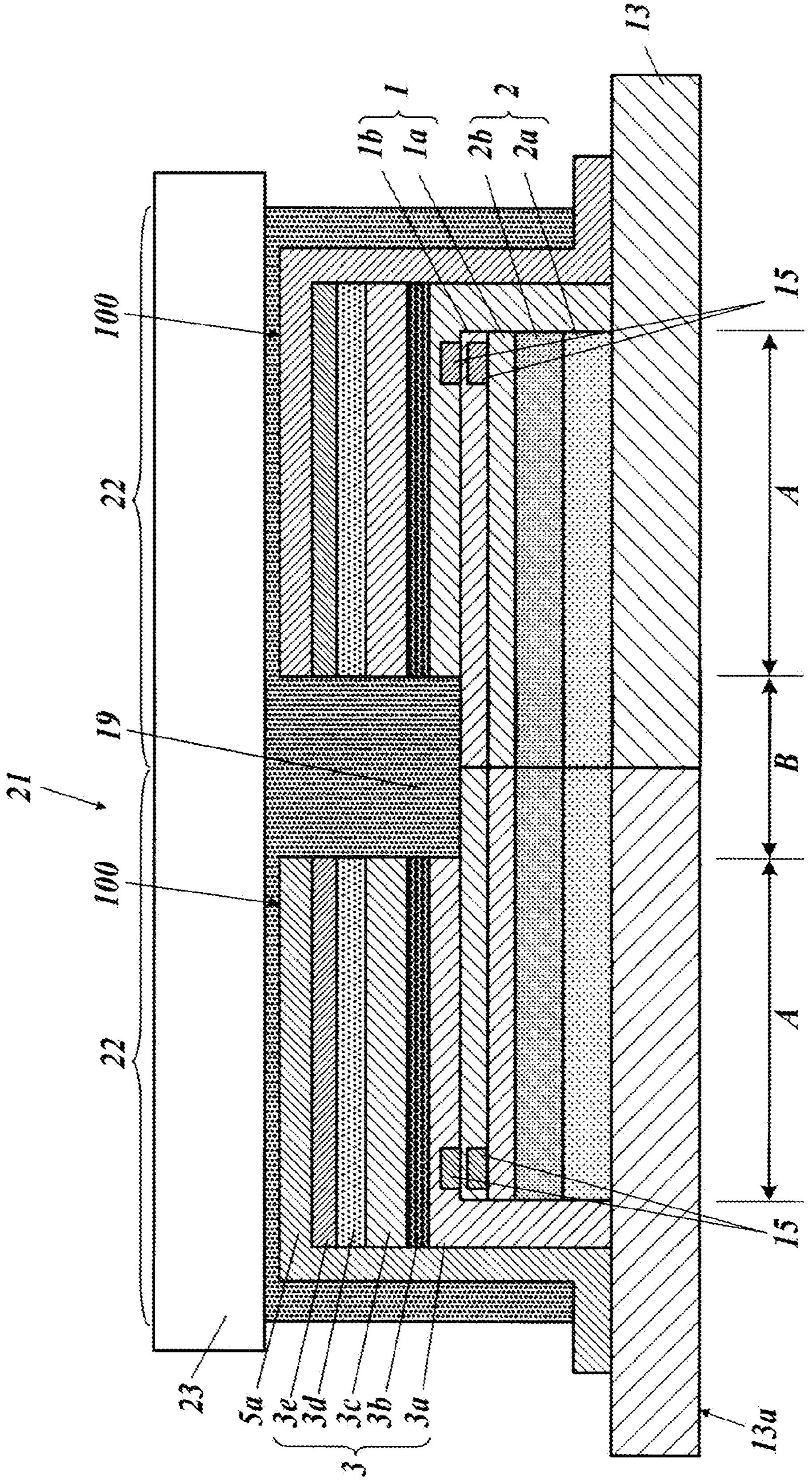
FIG. 10 is a schematic cross-sectional view showing the structure of an illumination device having a large light-emitting surface formed using organic light-emitting devices according to the present invention.

FIG. 10 is a cross-sectional view showing an example of an illumination device in which a plurality of organic light-emitting devices 100 each having the above structure are used to form a large light-emitting surface.

As shown in FIG. 10, an illumination device 21 includes a plurality of light-emitting panels 22 each having the organic light-emitting device 100 provided on the transparent substrate 13, in which the panels 22 are arranged (or tiled) on a support substrate 23 to form a larger light-emitting surface. The support substrate 23 may also serve as a sealant 17. The light-emitting panels 22 are tiled in such a way that the organic light-emitting devices 100 are sandwiched between the support substrate 23 and the transparent substrates 13 of the light-emitting panels 22. An adhesive 19 may be applied between the support substrate 23 and the transparent substrates 13 in order to seal the organic light-emitting devices 100. The terminals of the transparent electrodes 1 as anodes and the counter electrodes 5*a* as cathodes should be exposed at the periphery of the light-emitting panels 22. It should be noted that FIG. 10 only shows the exposed parts of the counter electrodes 5*a*.

As an example, FIG. 10 shows that the light-emitting functional layer 3 of the organic light-emitting device 100 includes the hole injection layer 3*a*, the hole transport layer 3*b*, the light-emitting layer 3*c*, the electron transport layer 3*d*, and the electron injection layer 3*e*, which are stacked in order on the transparent electrode 1.

In the illumination device 21 with such a structure, the central part of each light-emitting panel 22 forms a light-emitting region A, and a non-light-emitting region B occurs between the light-emitting panels 22. Therefore, a light extraction member for increasing the amount of light extracted from the non-light-emitting region B may be provided on the non-light-emitting region B of the light extraction surface 13*a*. A light condensing sheet or a light diffusion sheet may be used as the light extraction member.

Hereinafter, the present invention will be more specifically described with reference to examples, which, however, are not intended to limit the present invention.

Example 1

<<Preparation of Transparent Electrode>>

(1) Preparation of Internal Light Extraction Layers (1.1) Preparation of Internal Light Extraction Layer 1

According to Example 1 in JP 2012-116101 A, a gas barrier layer was formed on a PET substrate (125 μm in thickness).

More specifically, a 500-mm-wide, 125-μm-thick, polyester film with both sides treated for enhanced adhesion (Super Low Heat Shrinkage PET Q83 manufactured by Teijin DuPont Films Japan Limited) was provided. A UV-curable, organic-inorganic hybrid hard coating material OPSTAR Z7535 manufactured by JSR Corporation was applied to one side of the polyester film in such a way that a 4-μm-thick coating would be formed after drying. The coating was then dried under the conditions of 80° C. for 3 minutes and cured under the conditions of 1.0 J/cm$^2$ in the air atmosphere using a high-pressure mercury lamp, so that a bleed-out preventing layer was formed.

Subsequently, a UV-curable, organic-inorganic hybrid hard coating material OPSTAR Z7501 manufactured by JSR Corporation was applied to the other side of the resin substrate in such a way that a 4-μm-thick coating would be formed after drying. The coating was then dried under the conditions of 80° C. for 3 minutes and then cured under the conditions of 1.0 J/cm$^2$ in the air atmosphere using a high-pressure mercury lamp, so that a flat layer was formed.

The resulting flat layer had a maximum section height Rt (p) of 16 nm as measured for surface roughness according to JIS B 0601.

The surface roughness was measured with an atomic force microscope (AFM) SPI3800N DFM manufactured by SII. The area on which a single measurement operation was performed was 10 μm×10 μm. The measurement was performed three times on different sites, and the average of the Rt values measured respectively was used as the measured value.

The resin substrate prepared as described above had a thickness of 133 μm.

Subsequently, using a reduced-pressure extrusion coater, a coating liquid containing an inorganic precursor compound was applied to the surface of the flat layer of the resin substrate in such a way that a 150-nm-thick dried layer would be formed, when a first gas barrier layer was formed.

The coating liquid containing an inorganic precursor compound was prepared as a dibutyl ether solution of 5% by weight of an inorganic precursor compound by mixing a catalyst-free dibutyl ether solution of 20% by weight of perhydropolysilazane (AQUAMICA NN120-20 manufactured by AZ Electronic Materials) and a 5% by weight (on a solid basis) amine catalyst-containing dibutyl ether solution of 20% by weight of perhydropolysilazane (AQUAMICA NAX120-20 manufactured by AZ Electronic Materials), adjusting the amine catalyst solid content to 1% by weight, and then diluting the mixture with dibutyl ether.

After the application, the coating was dried under the conditions of a drying temperature of 80° C., a drying time of 300 seconds, and a drying atmosphere dew point of 5° C.

After the drying, the resin substrate was gradually cooled to 25° C. and then subjected to a modification treatment by applying vacuum ultraviolet light to the coating surface in a vacuum ultraviolet irradiation device. The light source of the vacuum ultraviolet irradiation device was a Xe excimer lamp having a double tube structure configured to emit 172 nm vacuum ultraviolet light.

In each of the application, drying, and modification treatment steps, the same level of tension was applied by a tension control mechanism (not shown).

After the modification treatment, the gas barrier layer-bearing substrate was dried as described above and then subjected to a second modification treatment under the same conditions so that the gas barrier layer formed had a dry thickness of 150 nm.

Subsequently, a second gas barrier layer was formed on the first gas barrier layer in the same way as for the first gas barrier layer, so that a gas barrier-coated PET film was obtained.

Subsequently, according to the method described in WO 2000/36665 A, a PMMA layer (300 nm in thickness) was formed on the PET film by forming a polymethyl methacrylate oligomer by vacuum deposition and polymerizing the oligomer.

Subsequently, using imprint molding, the dip-and-bump shape of a mold was transferred to the surface of the PMMA layer, so that a scattering layer having the dip-and-bump structure was formed. More specifically, the PMMA layer was heated and pressed against a stainless steel roll having an embossed surface previously formed for marking. In this process, dips 150 nm in diameter and 120 nm in depth were formed in a square lattice pattern with a pitch (period) of 300 nm (the pattern produces a light diffraction effect to increase the efficiency of extraction of light in the range of 10 to 580 nm, what is called a green region).

A mixture of a polyester emulsion (Z561 manufactured by GOO Chemical Co., Ltd.) and a titanium oxide sol dispersion was applied to the scattering layer and then dried to form a smooth layer with an average dry thickness of 700 nm.

The PMMA film (scattering layer) had a refractive index of 1.5, and the uppermost layer of the polyester emulsion-titanium oxide sol mixture (the smooth layer) had a refractive index of 1.85. The whole of the internal light extraction layer had a refractive index of 1.8.

(1.2) Preparation of Internal Light Extraction Layer 2

Internal light extraction layer 2 was prepared as in the preparation of internal light extraction layer 1, except that a dip-and-bump structure was formed on the surface of the PMMA film as shown below.

Using imprint molding, the surface of the PMMA film was heated and pressed against a stainless steel roll having a corrugated embossed surface for marking, so that a randomly, gently corrugated shape with an average pitch of 3 μm and an average height of 500 nm was formed.

The PMMA film (scattering layer) had a refractive index of 1.5, and the uppermost layer of the polyester emulsion-titanium oxide sol mixture (the smooth layer) had a refractive index of 1.85. The whole of the internal light extraction layer had a refractive index of 1.8.

(1.3) Preparation of Internal Light Extraction Layer 3

The substrate used was a 0.7-mm-thick, 60 mm×60 mm, transparent, alkali-free glass substrate, which was degreased, washed with ultrapure water, and dried with a clean dryer before use.

A scattering layer-forming liquid formulation was then designed per 10 ml in the following manner: $TiO_2$ particles with a refractive index of 2.4 and an average particle size of 0.25 μm (JR600A manufactured by TAYCA CORPORATION) and a resin solution (ED230AL (organic-inorganic hybrid resin) manufactured by APM) were mixed in a solid content ratio of 70 vol %/30 vol % using n-propyl acetate and cyclohexanone in a solvent ratio of 10 wt %/90 wt % to form a composition with a solid concentration of 15 wt %.

More specifically, the $TiO_2$ particles were mixed with the solvents and dispersed for 10 minutes with an ultrasonic disperser (UH-50 manufactured by SMT Corporation) under the standard conditions for microchip step (MS-3, 3 mmϕ, manufactured by SMT Corporation) while cooled at room temperature, so that a $TiO_2$ dispersion was obtained.

Subsequently, while the $TiO_2$ dispersion was stirred at 100 rpm, the resin was gradually added and mixed into the dispersion. After the addition was completed, the stirring rate was raised to 500 rpm, and the mixing was performed for 10 minutes, so that a scattering coating liquid was obtained.

The coating liquid was then filtered through a 0.45 μm, hydrophobic PVDF filter (manufactured by Whatman) to give the desired dispersion.

The dispersion was applied to the substrate by spin coating (500 rmp, 30 seconds) and then preliminarily dried (80° C., 2 minutes). The dried product was further baked (120° C., 60 minutes) to form a 0.5-μm-thick scattering layer.

A smooth layer-forming liquid formulation was then designed per 10 ml in the following manner: a dispersion of nano $TiO_2$ with an average particle size of 0.02 μm (HDT-760T manufactured by TAYCA CORPORATION) and a resin solution (ED230AL (organic-inorganic hybrid resin) manufactured by APM) were mixed in a solid content ratio of 45 vol %/55 vol % using n-propyl acetate, cyclohexanone, and toluene in a solvent ratio of 20 wt %/30 wt %/50 wt % to form a composition with a solid concentration of 20 wt %.

More specifically, the nano $TiO_2$ dispersion was mixed with the solvents. While the mixture was stirred at 100 rpm, the resin was gradually added and mixed into the mixture. After the addition was completed, the stirring rate was raised to 500 rpm, and the mixing was performed for 10 minutes, so that a smooth coating liquid was obtained.

The coating liquid was then filtered through a 0.45 μm, hydrophobic PVDF filter (manufactured by Whatman) to give the desired dispersion.

The dispersion was applied to the scattering layer by spin coating (500 rmp, 30 seconds) and then preliminarily dried (80° C., 2 minutes). The dried product was further baked (120° C., 30 minutes) to form a 0.7-μm-thick smooth layer, so that internal light extraction layer 3 was obtained.

The smooth layer alone had a refractive index of 1.85.

Internal light extraction layer 3, prepared as described above, had a transmittance T of 67% and a haze value Hz of 50%.

According to D542, the refractive index of the whole of the internal light extraction layer was measured at a wavelength of 550 nm using an ellipsometer manufactured by SOPRA. The measured refractive index was 1.85.

(1.4) Preparation of Internal Light Extraction Layer 4

Internal light extraction layer 4 was prepared as in the preparation of internal light extraction layer 3, except that the alkali-free glass substrate was replaced by the gas barrier-coated PET film for internal light extraction layer 1.

(1.5) Preparation of Internal Light Extraction Layer 5

Internal light extraction layer 5 was prepared as in the preparation of internal light extraction layer 3, except that the formulation of the scattering layer and the smooth layer was changed as shown below using materials other than the $TiO_2$ particles.

A scattering layer-forming liquid formulation was designed per 10 ml in the following manner: $SiO_2$ particles with a refractive index of 1.5 and an average particle size of 0.4 μm (Sciqas manufactured by Sakai Chemical Industry Co., Ltd.) and a resin solution (ED230AL (organic-inorganic hybrid resin) manufactured by APM) were mixed in a solid content ratio of 70 vol %/30 vol % using n-propyl acetate and cyclohexanone in a solvent ratio of 10 wt %/90 wt % to form a composition with a solid concentration of 15 wt %.

A smooth layer-forming liquid was prepared as in the preparation of the smooth layer-forming liquid for internal light extraction layer 3, except that the dispersion of nano $TiO_2$ was not used.

The smooth layer alone had a refractive index of 1.5.

The whole of the internal light extraction layer had a refractive index of 1.5.

(2) Preparation of Transparent Electrodes (2.1) Preparation of Transparent Electrode 1-1

The internal light extraction layer 1-bearing PET substrate was fixed on a substrate holder for a commercially available vacuum deposition system. Illustrative compound 10 was added to a resistance heating tantalum boat. The substrate holder and the heating boat were then placed in a first vacuum chamber of the vacuum deposition system. Silver (Ag) was added to a resistance heating tungsten boat, which was then placed in a second vacuum chamber.

Firstly, after the pressure in the first vacuum chamber was reduced to $4\times10^{-4}$ Pa, the heating boat containing illustrative compound 10 was heated by passing a current through it, and an underlying layer of illustrative compound 10 with a thickness of 25 nm was formed on the substrate (smooth layer) at a deposition rate of 0.1 to 0.2 nm/sec.

Subsequently, the underlying layer-bearing substrate was transferred under vacuum to the second vacuum chamber. After the pressure in the second vacuum chamber was reduced to $4\times10^{-4}$ Pa, the heating boat containing silver was heated by passing a current through it, and an electrode layer of silver with a thickness of 8 nm was formed on the substrate (underlying layer) at a deposition rate of 0.1 to 0.2 nm/sec, so that transparent electrode 1-1 with a multilayer structure composed of the underlying layer and the electrode layer was obtained.

(2.2) Preparation of Transparent Electrodes 1-2 to 1-5

Transparent electrodes 1-2 to 1-5 were each prepared as in the preparation of transparent electrode 1, except that internal light extraction layer 1 was replaced by each of internal light extraction layers 2 to 5.

(2.3) Preparation of Transparent Electrode 1-6

A PET substrate (125 μm in thickness) was fixed on a substrate holder for a commercially available vacuum deposition system. Illustrative compound 10 was added to a resistance heating tantalum boat. The substrate holder and the heating boat were then placed in a first vacuum chamber of the vacuum deposition system. Silver (Ag) was added to a resistance heating tungsten boat, which was then placed in a second vacuum chamber.

In this state, first, after the pressure in the first vacuum chamber was reduced to $4\times10^{-4}$ Pa, the heating boat containing illustrative compound 10 was heated by passing a current through it, and an underlying layer of illustrative compound 10 with a thickness of 25 nm was formed on the substrate at a deposition rate of 0.1 to 0.2 nm/sec.

Subsequently, the underlying layer-bearing substrate was transferred under vacuum to the second vacuum chamber. After the pressure in the second vacuum chamber was reduced to $4\times10^{-4}$ Pa, the heating boat containing silver was heated by passing a current through it, and an electrode layer of silver with a thickness of 8 nm was formed on the substrate (underlying layer) at a deposition rate of 0.1 to 0.2 nm/sec, so that transparent electrode 1-6 with a multilayer structure composed of the underlying layer and the electrode layer was obtained.

(2.4) Preparation of Transparent Electrode 1-7

Transparent electrode 1-7 was prepared as in the preparation of transparent electrode 1-6, except that the PET substrate was replaced by an alkali-free glass substrate, which was the same as for internal light extraction layer 3.

(2.5) Preparation of Transparent Electrode 1-8

A 0.7-mm-thick, 60 mm×60 mm, transparent, alkali-free glass substrate was degreased, washed with ultrapure water, and dried with a clean dryer. The substrate was then heated at 300° C. (for 600 seconds) in a vacuum chamber. Subsequently, using a DC magnetron sputtering system, a 100-nm-thick film of 99.99% purity ITO ($In_2O_3$ 90%, $SnO_2$ 10%) was deposited on the glass substrate at constant Ar and $O_2$ gas flow rates, so that transparent electrode 1-8 was obtained.

(2.6) Preparation of Transparent Electrode 1-9

Transparent electrode 1-9 was prepared as in the preparation of transparent electrode 1-8, except that an ITO electrode (100 nm in thickness) was formed on a PET substrate (125 μm in thickness) at room temperature.

<<Evaluation of Transparent Electrodes>>

(1) Measurement of Electric Resistance

The electric resistance (Ω) of each prepared transparent electrode was measured with a resistivity meter (MCP-T610 manufactured by Mitsubishi Chemical Corporation) by four-terminal four-probe method under constant current application.

Table 1 shows the results.

TABLE 1

| Transparent electrode No. | Substrate | Internal light extraction layer: Scattering layer: Mode | Average particle size (μm) | Smooth layer | Refractive index | Transparent electrode: Underlying layer material | Electrode layer: Material | Thickness (nm) | Driving voltage (V) | Resistance (Ω) |
|---|---|---|---|---|---|---|---|---|---|---|
| 1-1 | PET | Shape-controlled (square lattice pattern) | — | Present | 1.8 | Compound 10 | Ag | 8 | 3.3 | 8 |
| 1-2 | PET | Shape-controlled (corrugated pattern) | — | Present | 1.8 | Compound 10 | Ag | 8 | 3.3 | 8 |
| 1-3 | Alkali-free glass | Scattering mixture ($TiO_2$) | 0.25 | Present | 1.85 | Compound 10 | Ag | 8 | 3.3 | 8 |
| 1-4 | PET | Scattering mixture ($TiO_2$) | 0.25 | Present | 1.85 | Compound 10 | Ag | 8 | 3.3 | 8 |
| 1-5 | Alkali-free glass | Scattering mixture ($SiO_2$) | 0.4 | Present | 1.5 | Compound 10 | Ag | 8 | 3.3 | 8 |
| 1-6 | PET | — | — | | — | Compound 10 | Ag | 8 | 3.3 | 8 |
| 1-7 | Alkali-free glass | — | — | | — | Compound 10 | Ag | 8 | 3.3 | 8 |
| 1-8 | Alkali-free glass | — | — | | — | — | ITO | 100 | 3.3 | 8 |
| 1-9 | PET | — | — | | — | — | ITO | 100 | 3.3 | 120 |

(2) Conclusion

Table 1 shows that transparent electrode 1-8 with the ITO transparent electrode formed on the glass substrate has an electric resistance of 8Ω while transparent electrode 1-9 with the ITO transparent electrode formed on the film substrate has an electric resistance of 120Ω, which is significantly higher than the former.

In contrast, transparent electrodes 1-6 and 1-7, formed on a glass substrate and a PET substrate, respectively, using a thin silver electrode, both have an electric resistance of 8Ω, with no difference between them, which shows that they are useful as electrodes regardless of what the substrate is made of. Similar results are obtained for transparent electrodes 1-1 to 1-5 having the thin silver electrode on which the internal light extraction layer is formed.

These results show that the thin silver electrode is superior to the ITO electrode and that the internal light extraction layer formed on the electrode does not affect the electrode performance.

Example 2

<<Preparation of Light-Emitting Panel>>

Figure 11:
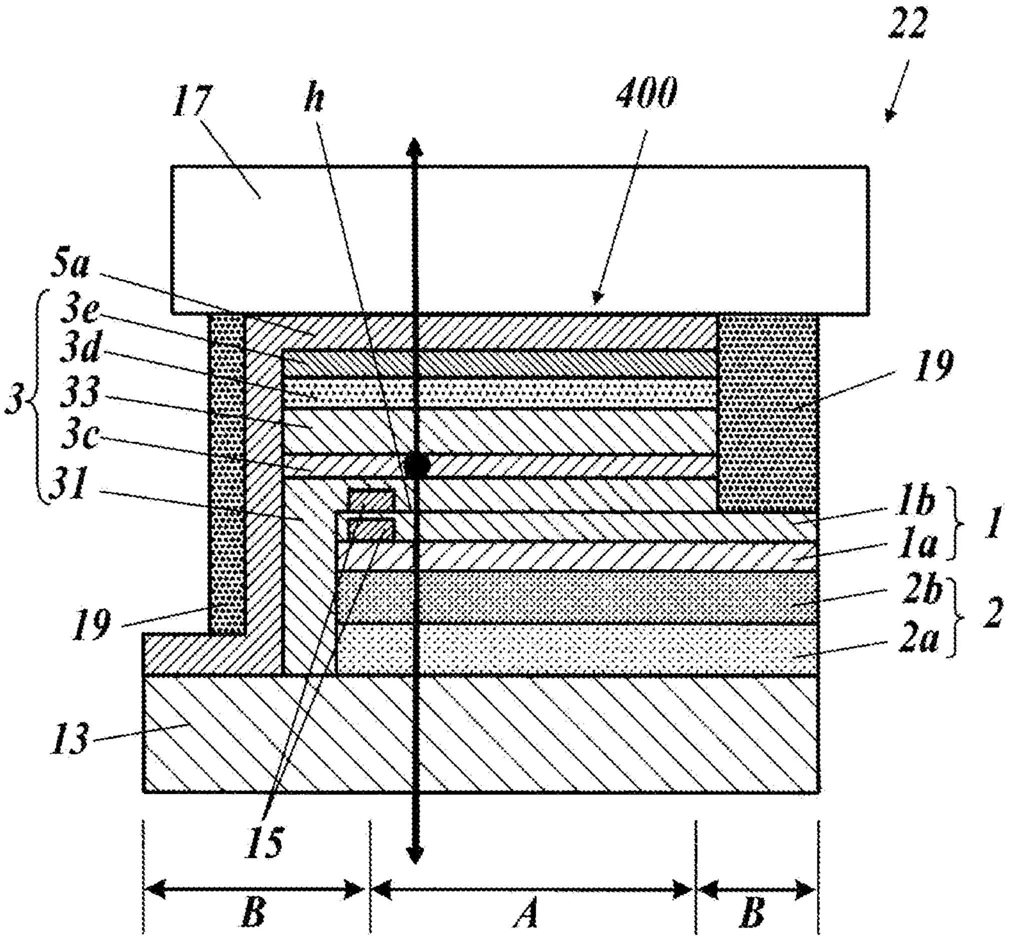
FIG. 11 is a cross-sectional view for illustrating an organic light-emitting device prepared in Examples.

A double-sided emission organic light-emitting device was prepared using, as an anode, each transparent electrode prepared in Example 1. Hereinafter, the preparation procedure will be described with reference to FIG. 11.

(1) Preparation of Light-Emitting Panel 2-1

First, the internal light extraction layer 2 and transparent electrode 1-bearing transparent substrate 13 (transparent electrode 1-3) was fixed on a substrate holder for a commercially available vacuum deposition system. A vapor deposition mask was placed facing the surface of the transparent electrode 1 where deposition was to be performed. Each of the materials for forming a light-emitting functional layer 3 was also added, in an amount optimal for the deposition of each layer, to each heating boat in the vacuum deposition system. Each heating boat used was made of a resistance heating tungsten material.

Subsequently, the pressure in the deposition chamber of the vacuum deposition system was reduced to a degree of vacuum of $4\times10^{-4}$ Pa, and the heating boats containing the materials, respectively, were sequentially heated by passing a current through them, when each layer was formed as shown below.

First, a heating boat containing α-NPD of the structural formula shown below as a hole transport/injection material was heated by passing a current through it so that a hole transport/injection layer 31 of α-NPD for serving as both a hole injection layer and a hole transport layer was formed on the electrode layer 1*b* of the transparent electrode 1. In this process, the deposition rate was 0.1 to 0.2 nm/sec, and the thickness of the layer was 20 nm.

[Chemical formula 40]

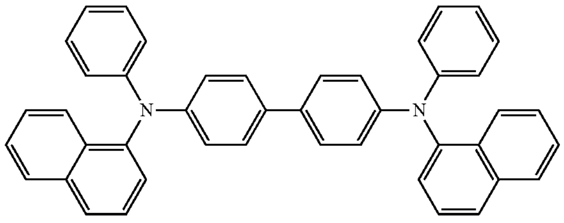

α-NPD

Subsequently, a heating boat containing host material H4 of the structural formula shown below and a heating boat containing phosphorescence-emitting compound Ir-4 of the structural formula shown below were each independently energized so that a light-emitting layer 3*c* composed of host material H4 and phosphorescence-emitting compound Ir-4 was formed on the hole transport/injection layer 31. In this process, the passage of current through the heating boats was controlled so that the deposition rate ratio of host material H4 to phosphorescence-emitting compound Ir-4 was 100:6. The thickness of the layer was 30 nm.

[Chemical formula 41]

H4

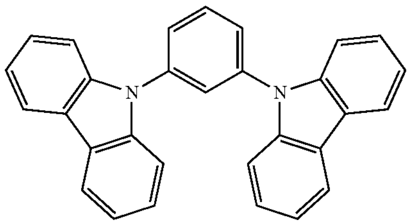

Ir-4

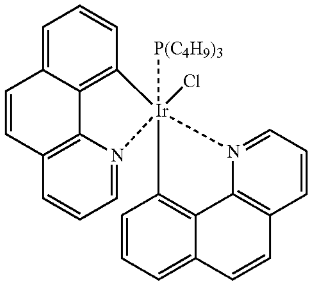

Subsequently, a heating boat containing BAlq of the structural formula shown below as a hole-blocking material was heated by passing a current through it so that a hole-blocking layer 33 of BAlq was formed on the light-emitting layer 3*c*. In this process, the deposition rate was 0.1 to 0.2 nm/sec, and the thickness of the layer was 10 nm.

[Chemical formula 42]

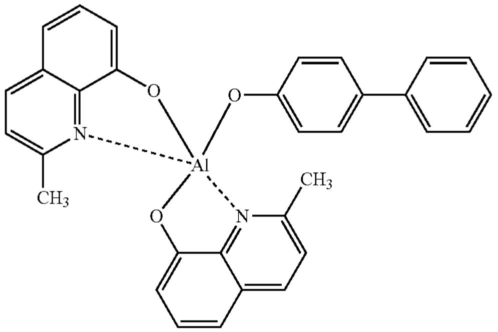

BAlq

Subsequently, a heating boat containing illustrative compound 10 of the structural formula shown above as an electron transport material and a heating boat containing potassium fluoride were each independently energized so that an electron transport layer 3*d* composed of illustrative compound 10 and potassium fluoride was formed on the hole-blocking layer 33. In this process, the passage of current through the heating boats was controlled so that the deposition rate ratio of illustrative compound 10 to potassium fluoride was 75:25. The thickness of the layer was 30 nm.

Subsequently, a heating boat containing potassium fluoride as an electron injection material was heated by passing a current through it so that an electron injection layer 3*e* of potassium fluoride was formed on the electron transport layer 3*d*. In this process, the deposition rate was 0.01 to 0.02 nm/sec, and the thickness of the layer was 1 nm.

Thereafter, the electron injection layer 3*e*-bearing transparent substrate 13 was transferred from the deposition chamber of the vacuum deposition system under vacuum into the process chamber of a sputtering system having an ITO target attached as a counter electrode material. In the process chamber, an optically transparent counter electrode 5*a* of ITO with a thickness of 150 nm was then formed as a cathode at a deposition rate of 0.3 to 0.5 nm/sec. In this way, an organic light-emitting device 400 was formed on the transparent substrate 13.

Subsequently, the organic light-emitting device 400 was covered with a sealant 17 of a 300-μm-thick glass base material. While the organic light-emitting device 400 was covered, an adhesive 19 (sealing material) was applied between the sealant 17 and the transparent substrate 13. The adhesive 19 used was a photo-curing epoxy adhesive (LUXTRAK LC0629B manufactured by Toagosei Co., Ltd.). The adhesive 19 applied between the sealant 17 and the transparent substrate 13 was irradiated with UV light from the glass base material (sealant 17) side, so that the adhesive 19 was cured to seal the organic light-emitting device 400.

In the process of forming the organic light-emitting device 400, a vapor deposition mask was used in the formation of each layer, so that a 4.5 cm×4.5 cm light-emitting region A was formed at the center of the 5 cm×5 cm transparent substrate 13, and a non-light-emitting region B with a width of 0.25 cm was formed around the whole of the light-emitting region A. The transparent electrode 1 as an anode and the counter electrode 5*a* as a cathode were each formed to have a terminal part extending to the edge of the transparent substrate 13, while they were insulated from each other with the light-emitting functional layer 3 having the components from the hole transport/injection layer 31 to the electron transport layer 3*e*.

In this way, light-emitting panel 2-1 was obtained, which had the organic light-emitting device 400 provided on the transparent substrate 13 and sealed with the sealant 17 and the adhesive 19.

In light-emitting panel 2-1, emitted light h of each color produced by the light-emitting layer 3*c* is extracted from both the transparent electrode 1 side and the counter electrode 5*a* side, in other words, both the transparent substrate 13 side and the sealant 17 side.

(2) Preparation of Light-Emitting Panel 2-2

Light-emitting panel 2-2 was prepared as in the preparation of light-emitting panel 2-1, except that transparent electrode 1-3 was replaced by transparent electrode 1-7 with no internal light extraction layer.

(3) Preparation of Light-Emitting Panel 2-3

Light-emitting panel 2-3 was prepared as in the preparation of light-emitting panel 2-1, except that the smooth layer was not formed when the internal light extraction layer was formed for transparent electrode 1-3.

The scattering layer had a refractive index of 2.1.

(4) Preparation of Light-Emitting Panel 2-4

Light-emitting panel 2-4 was prepared as in the preparation of light-emitting panel 2-1, except that the scattering layer was not formed when the internal light extraction layer was formed for transparent electrode 1-3.

The smooth layer had a refractive index of 1.85.

(5) Preparation of Light-Emitting Panels 2-5 to 2-8

Light-emitting panels 2-5 to 2-8 were each prepared as in the preparation of light-emitting panel 2-1, except that transparent electrode 1-3 was replaced by each of transparent electrodes 1-1, 1-2, 1-4, and 1-5.

<<Evaluation of Light-Emitting Panels>>

(1) Measurement of Driving Voltage and Luminous Efficiency

Each prepared light-emitting panel was turned on at room temperature (in the range of about 23 to 25° C.) under 2.5 mA/cm$^2$ constant current density conditions. The emission luminance of each sample was measured with a spectral radiance meter CS-2000 (manufactured by Konica Minolta), and the driving voltage (V) and the luminous efficiency (extraction efficiency) at the corresponding current value were determined.

Table 2 shows the results.

Note that the luminous efficiency is expressed as the relative value to the luminous efficiency of light-emitting panel 2-2 normalized to 100.

TABLE 2

| Light-emitting panel No. | Transparent electrode No. | Refractive index of internal light extraction layer | Driving voltage (V) | Luminous efficiency | Note |
|---|---|---|---|---|---|
| 2-1 | 1-3 | 1.85 | 3.3 | 130 | Inventive |
| 2-2 | 1-7 | — | 3.3 | 100 | Comparative |
| 2-3 | 1-3 (without smooth layer) | 2.1 (scattering layer) | Un-measurable | — | Comparative |
| 2-4 | 1-3 (without scattering layer) | 1.85 (smooth layer) | 3.3 | 90 | Comparative |
| 2-5 | 1-1 | 1.8 | 3.3 | 120 | Inventive |
| 2-6 | 1-2 | 1.8 | 3.3 | 120 | Inventive |
| 2-7 | 1-4 | 1.85 | 3.3 | 130 | Inventive |
| 2-8 | 1-5 | 1.5 | 3.3 | 90 | Comparative |

(2) Conclusion

Table 2 shows that light-emitting panels 2-1 and 2-5 to 2-7 according to the present invention have a higher luminous efficiency than light-emitting panels 2-2 to 2-4 and 2-8 as comparative examples. In light-emitting panel 2-3 as a comparative example with no smooth layer, a large leak current was observed with no light emission observed.

These results show that the internal light extraction layer provided adjacent to the thin silver electrode is useful when it includes the scattering layer and the smooth layer and has a refractive index in the range of 1.7 to less than 2.5.

Example 3

<<Preparation of Light-Emitting Panels>>

(1) Preparation of Light-Emitting Panels 3-1 to 3-7

Light-emitting panels 3-1 to 3-7 were each prepared as in the preparation of light-emitting panel 2-7, except that $TiO_2$ particles in the scattering layer were changed as shown in Table 3.

(2) Preparation of Light-Emitting Panel 3-8

Light-emitting panel 3-8 was prepared as in the preparation of light-emitting panel 2-7, except that the internal light extraction layer was not formed.

<<Evaluation of Light-Emitting Panels>>

(1) Measurement of Driving Voltage and Luminous Efficiency

The driving voltage (V) and the luminous efficiency of each prepared light-emitting panel were measured as in Example 2.

Table 3 shows the results.

Note that the luminous efficiency is expressed as the relative value to the luminous efficiency of light-emitting panel 3-8 normalized to 100.

(2) Measurement of Haze Value

The haze value of each prepared light-emitting panel was measured with HAZE METER NDH5000 manufactured by Tokyo Denshoku Co., Ltd. according to JIS K 7361-1 (1997).

Table 3 shows the results.

(3) Measurement of Emission Lifetime

The luminance of each prepared light-emitting panel was measured with a spectral radiance meter CS-1000 (manufactured by Konica Minolta) when it was driven at a constant current of 2.5 mA/cm$^2$ under a dry nitrogen gas atmosphere at 23° C. The time taken for the luminance to decrease to a half of the luminance immediately after the start of the light emission (the initial luminance) was determined as the half-lifetime ($\tau_{0.5}$), which was used as a measure of life.

Table 3 shows the measurement results.

Note that the emission lifetime is expressed as the relative value to the emission lifetime of light-emitting panel 3-8 normalized to 100.

TABLE 3

| Light-emitting panel No. | Transparent electrode No. | Scattering layer Material | Scattering layer Average particle size (μm) | Scattering layer Refractive index | Refractive index of internal light extraction layer | Driving voltage (V) | Luminous efficiency | Haze value (%) | Emission lifetime | Note |
|---|---|---|---|---|---|---|---|---|---|---|
| 3-1 | 1-4 | $TiO_2$ (MT-100HD manufactured by TAYCA CORPORATION) | 0.02 | 2.4 | 1.85 | 3.3 | 105 | 2 | 110 | Inventive |
| 3-2 | 1-4 | $TiO_2$ (MT-700HD manufactured by TAYCA CORPORATION) | 0.05 | 2.4 | 1.85 | 3.3 | 105 | 5 | 110 | Inventive |

TABLE 3-continued

| Light-emitting panel No. | Transparent electrode: No. | Transparent electrode: Scattering layer: Material | Scattering layer: Average particle size (μm) | Scattering layer: Refractive index | Refractive index of internal light extraction layer | Driving voltage (V) | Luminous efficiency | Haze value (%) | Emission lifetime | Note |
|---|---|---|---|---|---|---|---|---|---|---|
| 3-3 | 1-4 | $TiO_2$ (JR-405 manufactured by TAYCA CORPORATION) | 0.21 | 2.4 | 1.85 | 3.3 | 125 | 40 | 150 | Inventive |
| 2-7 | 1-4 | $TiO_2$ (JR-600A manufactured by TAYCA CORPORATION) | 0.25 | 2.4 | 1.85 | 3.3 | 130 | 50 | 150 | Inventive |
| 3-4 | 1-4 | $TiO_2$ (JR-301 manufactured by TAYCA CORPORATION) | 0.3 | 2.4 | 1.85 | 3.3 | 130 | 55 | 150 | Inventive |
| 3-5 | 1-4 | $TiO_2$ (MP-70 manufactured by TAYCA CORPORATION) | 0.7 | 2.4 | 1.85 | 3.3 | 130 | 50 | 142.5 | Inventive |
| 3-6 | 1-4 | $TiO_2$ (MP-100 manufactured by TAYCA CORPORATION) | 1 | 2.4 | 1.85 | 3.3 | 125 | 45 | 135 | Inventive |
| 3-7 | 1-4 | $TiO_2$ (TIO13PB manufactured by Kojundo Chemical Laboratory Co., Ltd.) | 2 | 2.4 | 1.85 | 3.3 | 125 | 40 | 100 | Inventive |
| 3-8 | 1-4 | — | — | — | — | 3.3 | 100 | 0 | 100 | Comparative |

(4) Conclusion

Table 3 shows that light-emitting panels 2-7 and 3-1 to 3-7 according to the present invention are superior in luminous efficiency, haze value, and emission lifetime to light-emitting panel 3-8 as a comparative example. Among them, light-emitting panels 2-7 and 3-3 to 3-6 show particularly good results for all characteristics.

These results show that the scattering layer is useful when it contains particles with an average particle size of 0.2 μm to less than 1 μm and a refractive index of 1.7 to less than 3.0.

INDUSTRIAL APPLICABILITY

The present invention is particularly suitable for use in providing organic light-emitting devices possessing high luminous efficiency and containing a transparent electrode having both conductivity and optical transparency.

The invention claimed is:

1. An organic light-emitting device comprising:

an internal light extraction layer comprising a scattering layer and a smooth layer; and a transparent electrode comprising an underlying layer and an electrode layer, wherein the transparent electrode is provided on a smooth layer side of the internal light extraction layer, the internal light extraction layer has a refractive index in the range of 1.7 to less than 2.5, the smooth layer has a refractive index in the range of 1.7 or more, and the electrode layer comprises silver or an alloy comprising silver as a main component.

2. The organic light-emitting device according to claim 1, wherein the scattering layer contains particles with an average particle size of 0.2 μm to less than 1 μm and a refractive index of 1.7 to less than 3.0.

3. The organic light-emitting device according to claim 1, wherein the scattering layer has a smooth layer-side surface formed to have a dip-and-bump structure.

4. The organic light-emitting device according to claim 1, wherein the underlying layer comprises a nitrogen atom-containing compound.

5. The organic light-emitting device according to claim 4, wherein the nitrogen atom-containing compound has a heterocyclic ring containing a nitrogen atom as a heteroatom.

6. The organic light-emitting device according to claim 4, wherein the nitrogen atom-containing compound has a pyridine group.

7. The organic light-emitting device according to claim 4, wherein the nitrogen atom-containing compound is a compound represented by formula (1):

[Chemical formula 1]

$(Ar1)n1\text{-}Y1$ Formula (1)

wherein n1 represents an integer of 1 or more,

Y1 represents a substituent when n1 is 1 or Y1 represents a simple bond or a n1-valent linking group when n1 is 2 or more, Ar1 represents a group represented by formula (A):

[Chemical formula 2]

Formula (A)

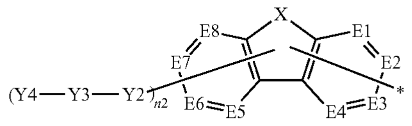

wherein X represents —N(R)—, —O—, —S—, or —Si(R)(R')—, E1 to E8 each independently represent —C(R1)= or —N═, R, R', and R1 each independently represent a hydrogen atom, a substituent, or a linking site to Y1, * represents a linking site to Y1, Y2 represents a simple bond or a divalent linking group, Y3 and Y4 each represent a group derived from a five- or six-membered aromatic ring, at least one of Y3 and Y4 represents a group derived from an aromatic heterocyclic ring containing a nitrogen atom as a ring-constituting atom, and n2 represents an integer of 1 to 4, when n1 is 2 or more, a plurality of occurrences of Ar1 may be the same or different, and the compound represented by formula (1) has, in its molecule, at least two condensed aromatic heterocyclic rings each formed by condensation of three or more rings.

8. The organic light-emitting device according to claim 2, wherein the underlying layer comprises a nitrogen atom-containing compound.

9. The organic light-emitting device according to claim 5, wherein the nitrogen atom-containing compound has a pyridine group.

10. The organic light-emitting device according to claim 5, wherein the nitrogen atom-containing compound is a compound represented by formula (1):

[Chemical formula 3]

(Ar1)*n*1-Y1 Formula (1)

wherein n1 represents an integer of 1 or more,

Y1 represents a substituent when n1 is 1 or Y1 represents a simple bond or a n1-valent linking group when n1 is 2 or more, Ar1 represents a group represented by formula (A):

[Chemical formula 4]

Formula (A)

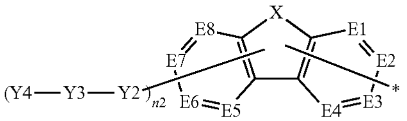

wherein X represents —N(R)—, —O—, —S—, or —Si(R)(R')—, E1 to E8 each independently represent —C(R1)= or —N═, R, R', and R1 each independently represent a hydrogen atom, a substituent, or a linking site to Y1, * represents a linking site to Y1, Y2 represents a simple bond or a divalent linking group, Y3 and Y4 each represent a group derived from a five- or six-membered aromatic ring, at least one of Y3 and Y4 represents a group derived from an aromatic heterocyclic ring containing a nitrogen atom as a ring-constituting atom, and n2 represents an integer of 1 to 4, when n1 is 2 or more, a plurality of occurrences of Ar1 may be the same or different, and the compound represented by formula (1) has, in its molecule, at least two condensed aromatic heterocyclic rings each formed by condensation of three or more rings.

11. The organic light-emitting device according to claim 3, wherein the underlying layer comprises a nitrogen atom-containing compound.

12. The organic light-emitting device according to claim 6, wherein the nitrogen atom-containing compound is a compound represented by formula (1):

[Chemical formula 5]

(Ar1)*n*1-Y1 Formula (1)

wherein n1 represents an integer of 1 or more,

Y1 represents a substituent when n1 is 1 or Y1 represents a simple bond or a n1-valent linking group when n1 is 2 or more, Ar1 represents a group represented by formula (A):

[Chemical formula 6]

Formula (A)

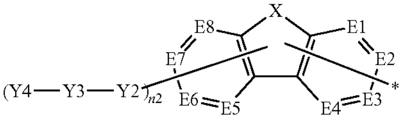

wherein X represents —N(R)—, —O—, —S—, or —Si(R)(R')—, E1 to E8 each independently represent —C(R1)= or —N═, R, R', and R1 each independently represent a hydrogen atom, a substituent, or a linking site to Y1, * represents a linking site to Y1, Y2 represents a simple bond or a divalent linking group, Y3 and Y4 each represent a group derived from a five- or six-membered aromatic ring, at least one of Y3 and Y4 represents a group derived from an aromatic heterocyclic ring containing a nitrogen atom as a ring-constituting atom, and n2 represents an integer of 1 to 4, when n1 is 2 or more, a plurality of occurrences of Ar1 may be the same or different, and the compound represented by formula (1) has, in its molecule, at least two condensed aromatic heterocyclic rings each formed by condensation of three or more rings.

* * * * *